(12) United States Patent
Zachar

(10) Patent No.: US 12,179,042 B2
(45) Date of Patent: Dec. 31, 2024

(54) TRANSCRANIAL ULTRASOUND FOCUSING

(71) Applicant: Oron Zachar, Tel Aviv (IL)

(72) Inventor: Oron Zachar, Tel Aviv (IL)

(73) Assignee: Oron Zachar, Tel Aviv (IL)

( * ) Notice: Subject to any disclaimer, the term of this patent is extended or adjusted under 35 U.S.C. 154(b) by 773 days.

(21) Appl. No.: 17/425,347

(22) PCT Filed: Jan. 31, 2019

(86) PCT No.: PCT/IB2019/000185
§ 371 (c)(1),
(2) Date: Jul. 23, 2021

(87) PCT Pub. No.: WO2020/157536
PCT Pub. Date: Aug. 6, 2020

(65) Prior Publication Data
US 2022/0126120 A1    Apr. 28, 2022

Related U.S. Application Data

(63) Continuation-in-part of application No. 15/902,361, filed on Feb. 22, 2018, now abandoned.
(Continued)

(51) Int. Cl.
*A61N 7/00* (2006.01)
*A61B 8/08* (2006.01)
*A61M 37/00* (2006.01)

(52) U.S. Cl.
CPC .............. *A61N 7/00* (2013.01); *A61B 8/0858* (2013.01); *A61B 8/5207* (2013.01);
(Continued)

(58) Field of Classification Search
CPC ....... A61M 37/0092; A61N 2007/0078; A61N 2007/0095; A61B 2017/00725
See application file for complete search history.

(56) References Cited

U.S. PATENT DOCUMENTS

| 3,239,801 A | 3/1966 | Mcgaughey |
| 3,927,557 A | 12/1975 | Viertl |
| (Continued) |

FOREIGN PATENT DOCUMENTS

| WO | 2014/118632 A1 | 8/2014 |
| WO | 2014/135987 A2 | 9/2014 |
| (Continued) |

OTHER PUBLICATIONS

"Investigation of a large-area phased array for focused ultrasound surgery through the skull" by Clement et al. Phys. Med. Biol. 45 1071 (Year: 2000).*
(Continued)

*Primary Examiner* — Jason M Ip
(74) *Attorney, Agent, or Firm* — Momentum IP; Marc Van Dyke

(57) ABSTRACT

Embodiments of the invention introduces a method and system for focusing ultrasonic energy through intervening skull tissue into a target site within a target brain tissue region under the skull, includes a transducer emitter array, a transducer receiver array, a processor receiving echo signals from the receiver to determine correction factors for the transducer elements to compensate for refraction occurring due to intervening tissue. The correction factors may include phase correction factors, and the phases of excitation signals provided to the transducer elements may be calibrated focusing based upon the phase correction factors to focus the ultrasonic energy to the tissue at the target site.

12 Claims, 56 Drawing Sheets

Related U.S. Application Data

(60) Provisional application No. 62/492,193, filed on Apr. 30, 2017, provisional application No. 62/474,715, filed on Mar. 22, 2017, provisional application No. 62/468,473, filed on Mar. 8, 2017, provisional application No. 62/462,398, filed on Feb. 23, 2017.

(52) U.S. Cl.
CPC .. *A61M 37/0092* (2013.01); *A61N 2007/0026* (2013.01); *A61N 2007/003* (2013.01); *A61N 2007/0078* (2013.01); *A61N 2007/0095* (2013.01)

(56) References Cited

U.S. PATENT DOCUMENTS

| | | |
|---|---|---|
| 4,630,607 A | 12/1986 | Duinker |
| 4,817,614 A | 4/1989 | Hassler |
| 4,869,239 A | 9/1989 | Krauss |
| 4,893,614 A | 1/1990 | Takayama |
| 4,936,303 A | 6/1990 | Detwiler |
| 4,962,752 A | 10/1990 | Reichenberger |
| 5,279,282 A | 1/1994 | Oppelt |
| 5,329,930 A | 7/1994 | Thomas |
| 5,984,881 A | 11/1999 | Ishibashi |
| 6,128,958 A | 10/2000 | Cain |
| 6,612,988 B2 | 9/2003 | Maor |
| 6,770,031 B2 | 8/2004 | Hynynen |
| 7,344,509 B2 | 3/2008 | Hynynen |
| 7,611,462 B2 | 11/2009 | Vortman |
| 8,088,067 B2 | 1/2012 | Vortman |
| 8,932,237 B2 | 1/2015 | Vitek |
| 2008/0177180 A1 | 7/2008 | Azhari |
| 2008/0262350 A1 | 10/2008 | Unger |
| 2013/0119984 A1 | 5/2013 | Levy |
| 2014/0112095 A1 | 4/2014 | Medan |
| 2015/0016682 A1 | 1/2015 | Levy |
| 2015/0359603 A1 | 12/2015 | Levy |
| 2016/0038770 A1 | 2/2016 | Tyler |
| 2016/0106395 A1 | 4/2016 | Hynynen |
| 2016/0184026 A1 | 6/2016 | Tlusty |
| 2016/0187473 A1 | 6/2016 | Maev |
| 2017/0103533 A1 | 4/2017 | Brokman |
| 2018/0177491 A1 | 6/2018 | Hynynen |
| 2018/0193675 A1 | 7/2018 | Vortman |
| 2018/0360420 A1 | 12/2018 | Vortman |
| 2019/0030375 A1 | 1/2019 | Zachar |
| 2019/0175954 A1 | 6/2019 | Levy |
| 2019/0307427 A1 | 10/2019 | Levy |

FOREIGN PATENT DOCUMENTS

| | | |
|---|---|---|
| WO | 2016/063117 A1 | 4/2016 |
| WO | 2016/092366 A2 | 6/2016 |
| WO | 2017/060865 A2 | 4/2017 |
| WO | 2017/212336 A1 | 12/2017 |
| WO | 2018/007868 A1 | 1/2018 |
| WO | 2018/011631 A2 | 1/2018 |
| WO | 2018/020315 A1 | 2/2018 |
| WO | 2018/130867 A1 | 7/2018 |
| WO | 2018/138576 A1 | 8/2018 |
| WO | 2019/058171 A1 | 3/2019 |
| WO | 2019/069135 A1 | 4/2019 |
| WO | 2019/116087 A1 | 6/2019 |
| WO | 2019/116094 A1 | 6/2019 |
| WO | 2019/116107 A1 | 6/2019 |
| WO | 2019/135160 A2 | 7/2019 |
| WO | 2019/220213 A1 | 11/2019 |
| WO | 2019/234497 A1 | 12/2019 |

OTHER PUBLICATIONS

Acoustical properties of the human skull F. J. Fry; J. E. Barger J. Acoust. Soc. Am. 63, 1576-1590 (1978).
Ding et al. ,Phys. Med. Biol. 60 (2015) 3975-3998.
Lindsey BD, Smith SW. Refraction Correction in 3D Transcranial Ultrasound Imaging. Ultrasonic imaging. 2014;36(1):35-54. doi:10.1177/0161734613510287).
Vibhor Krishna et al, JAMA Neurol. 2018; 75(2):246-254.
International Search Report for PCT/IB2019/000185 dated Jun. 25, 2019.
Written Opinion for PCT/IB2019/000185 dated Jun. 25, 2019.

* cited by examiner

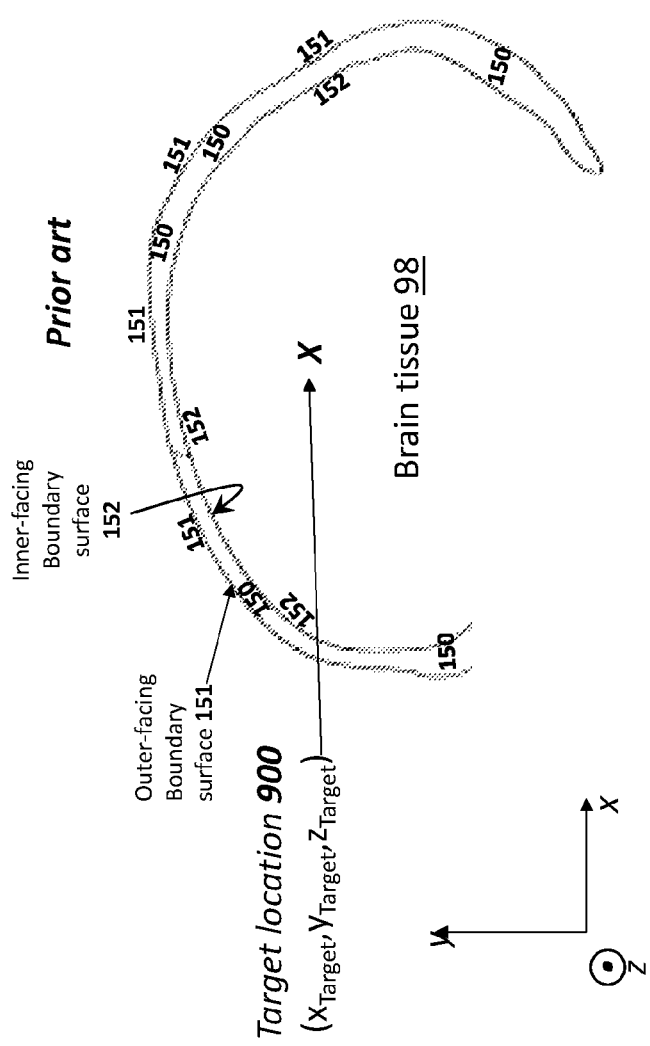
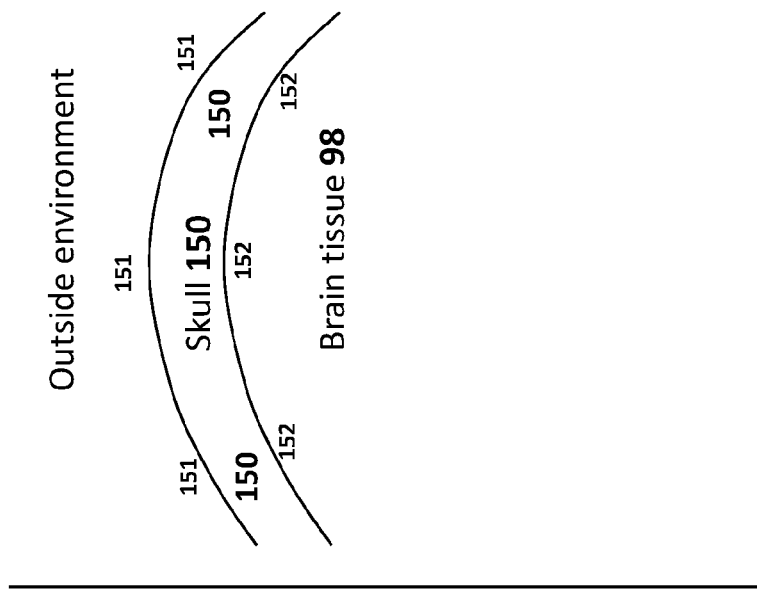
Fig. 1B
Fig. 1C

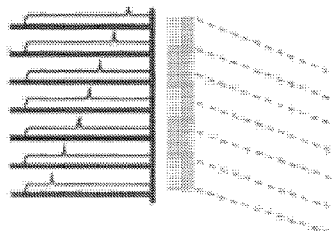
FIG. 3B (KNOWN ART)
Phased-array transducer
causing only steering
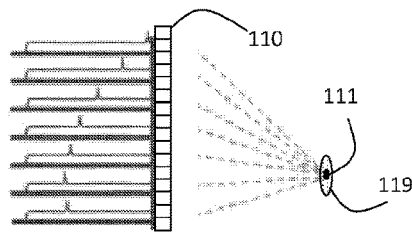
FIG. 3C (KNOWN ART)
Phased-array transducer causing
steering and focusing at same time
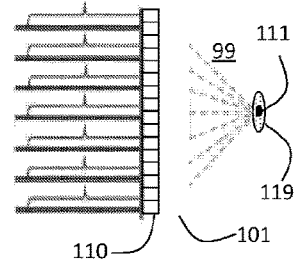
FIG. 3A (KNOWN ART)
Generic focusing module
representation

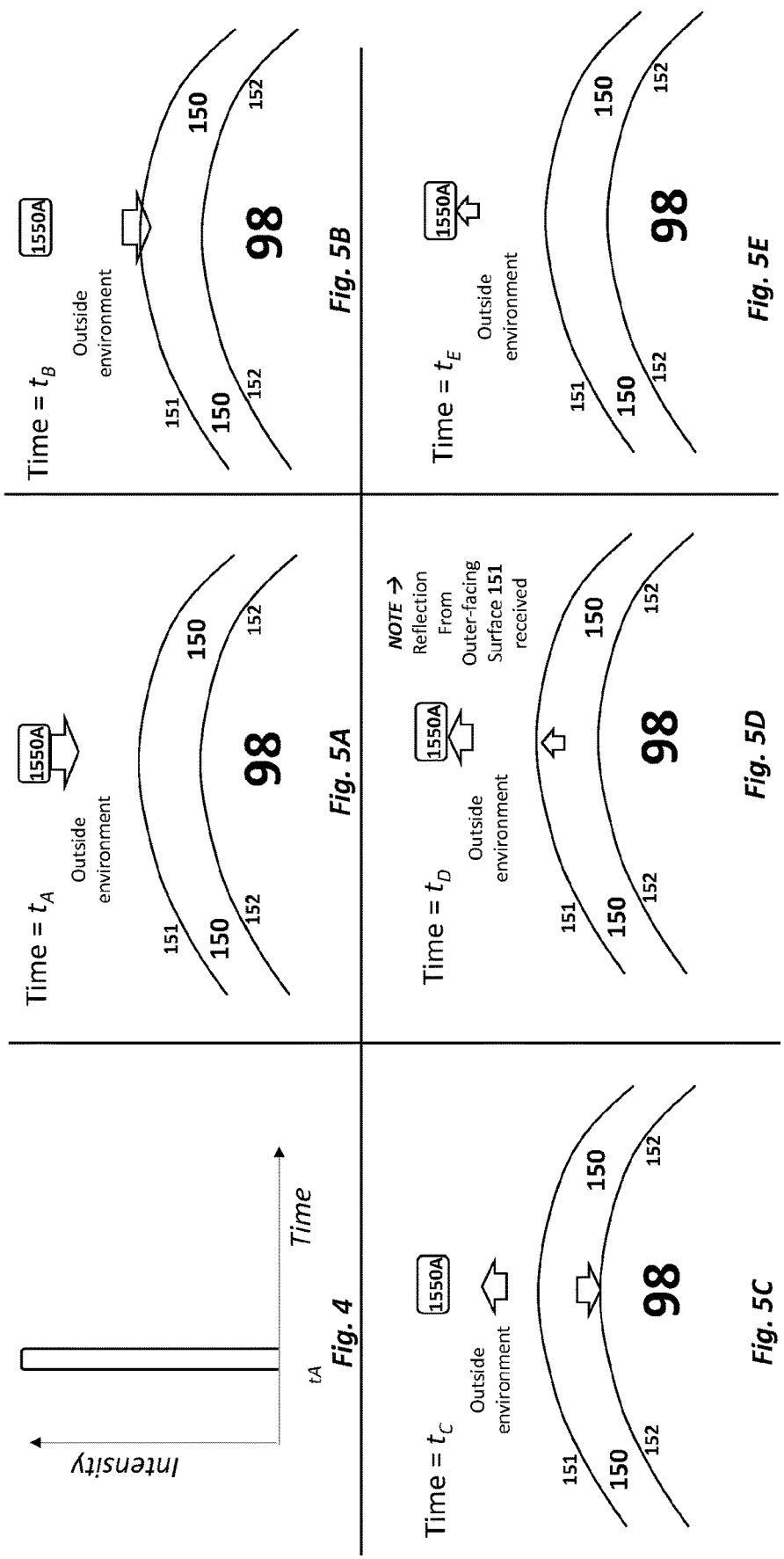

"Optical" path
For the first echo 151
150
152

1550A
First leg
Second leg

"Optical" path
For the second echo 151
150
152

1550A
First leg
Second leg

"Optical" path
For the First echo

"Optical" path
For the Second echo

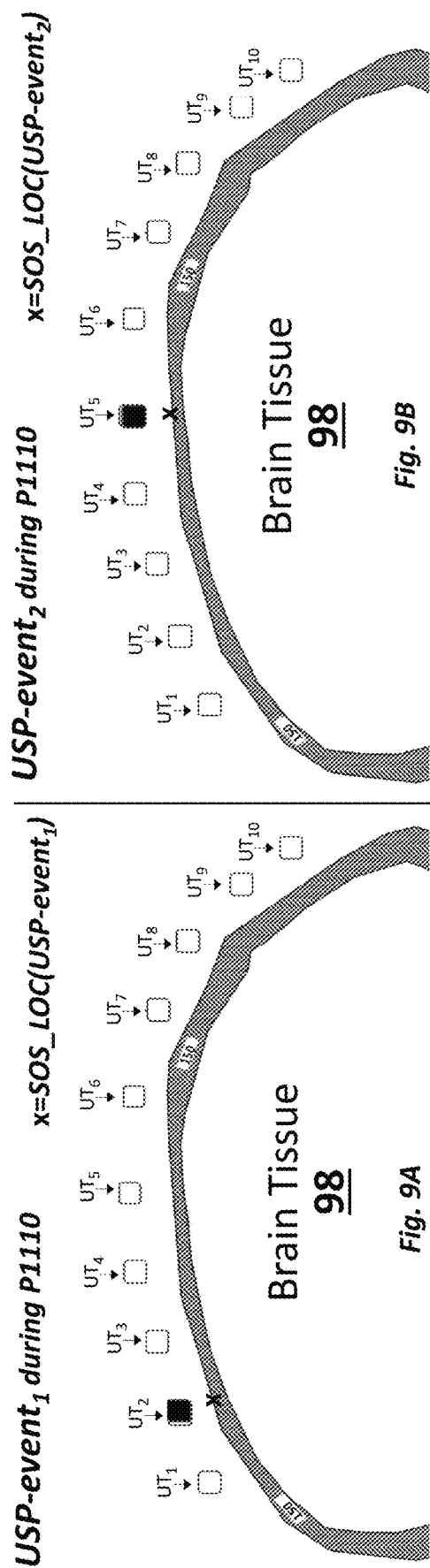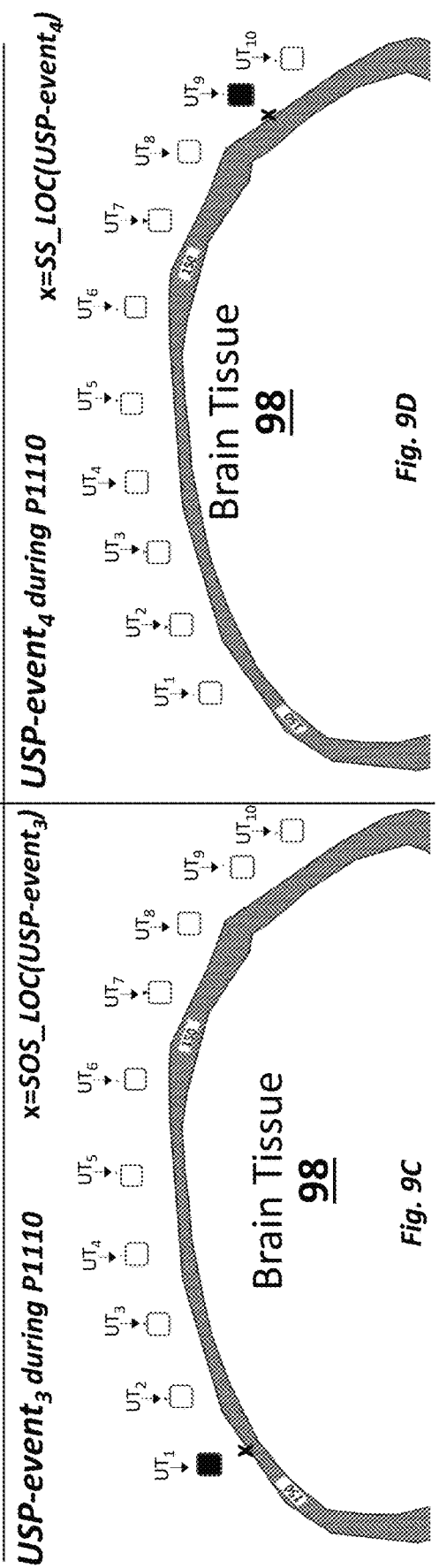

*For USP-event₄*

EFV = energy flux vector

*For USP-event₁*

EFV = energy flux vector

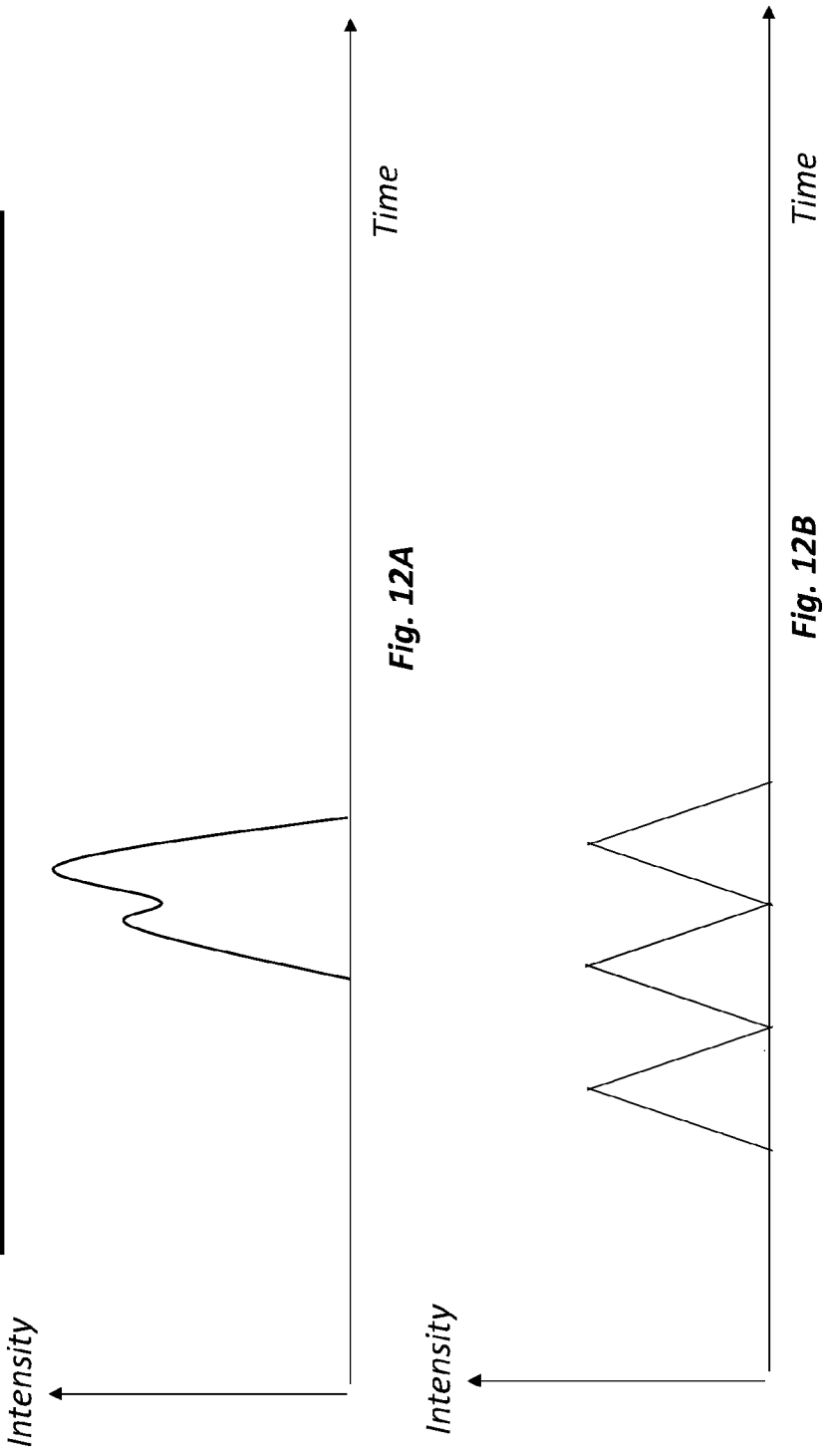

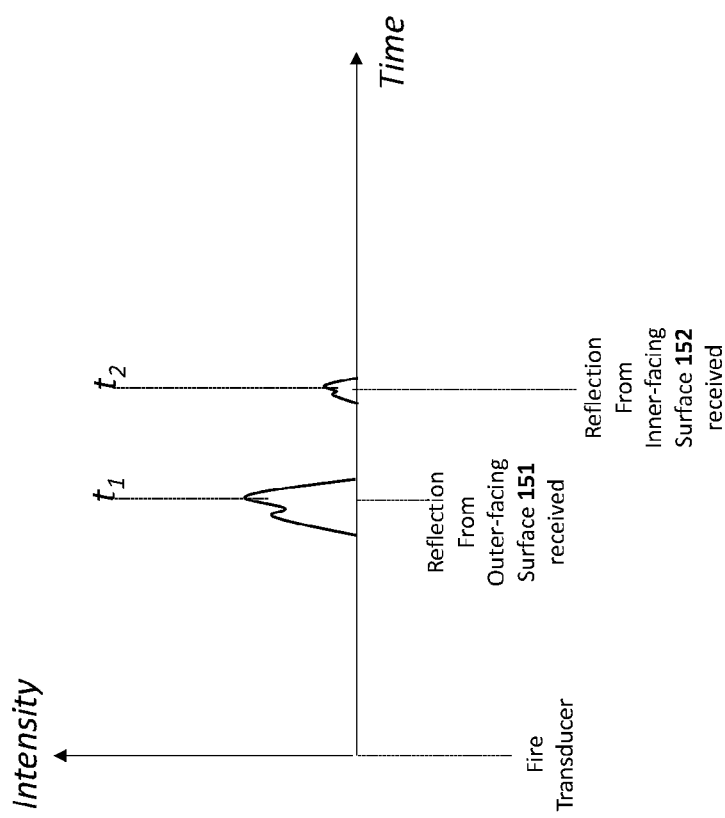

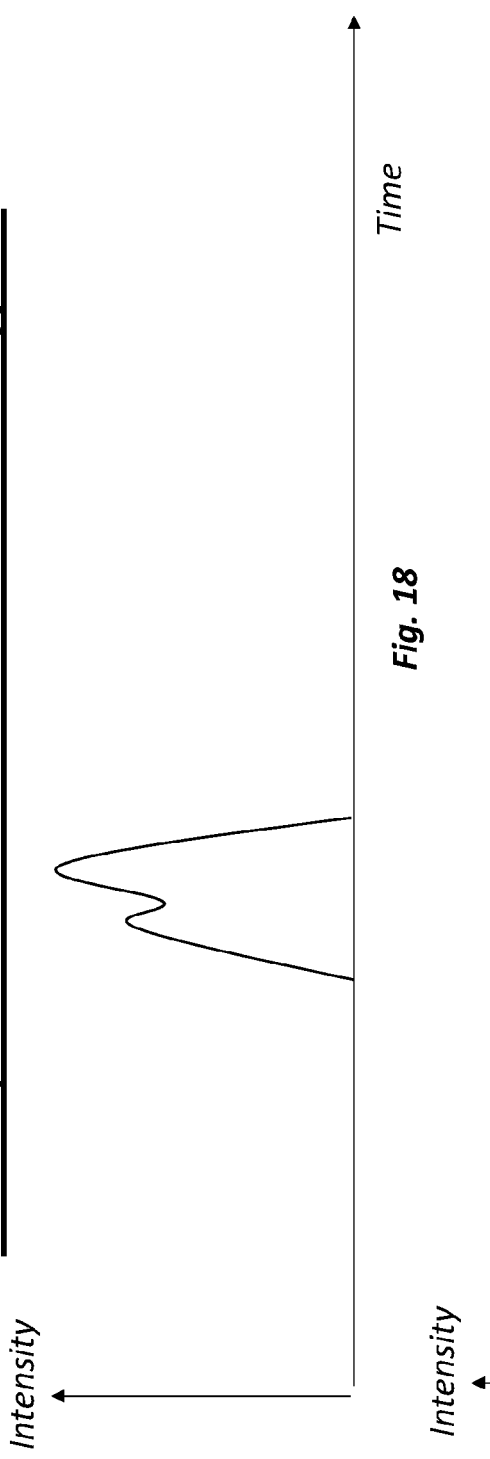
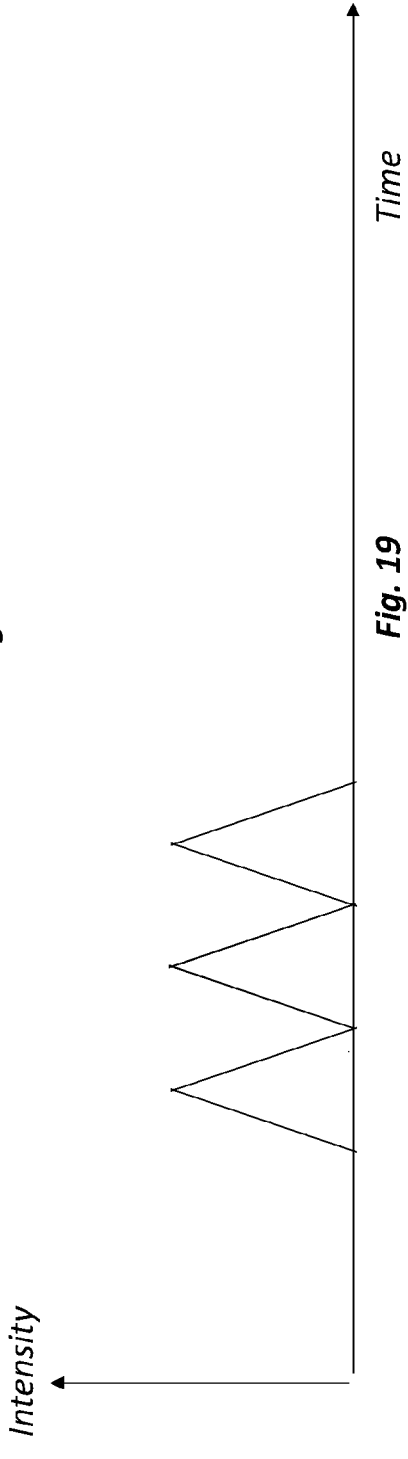

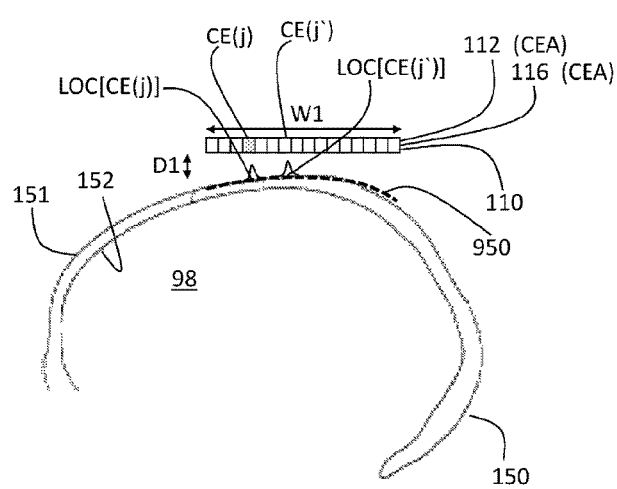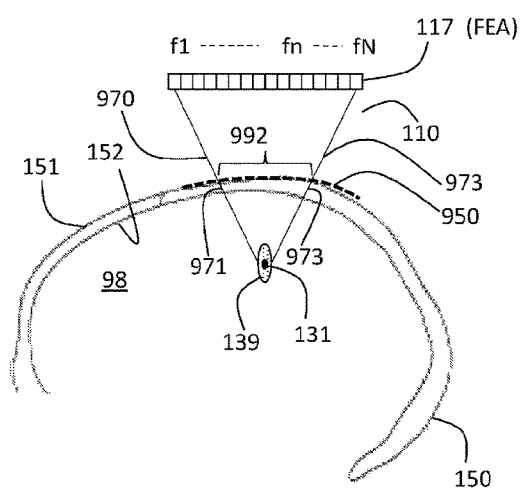
FIG. 21A
FIG. 21B

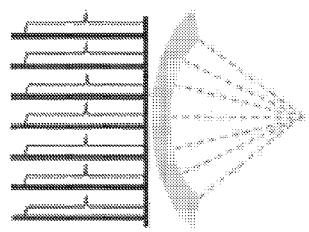
FIG. 22A (KNOWN ART)
Spherically-curved
transducer array
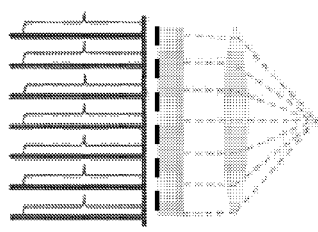
FIG. 22B (KNOWN ART)
Flat transducer array with
interchangeable lens
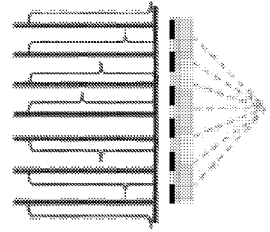
FIG. 22C (KNOWN ART)
Phased-array transducer
causing focusing
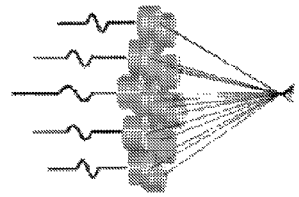
FIG. 22D (KNOWN ART)

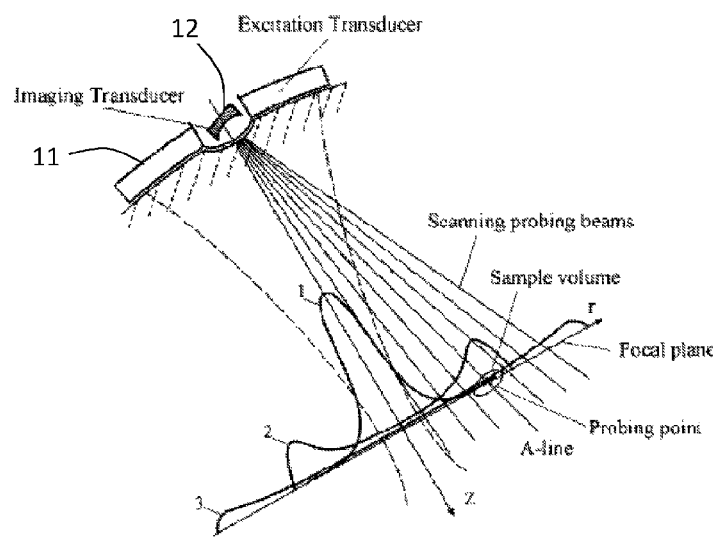
FIG.22E (KNOWN ART)

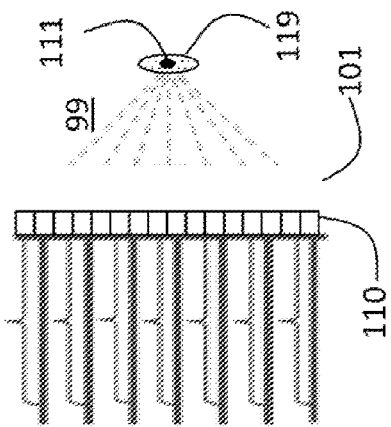
Fig. 23A (KNOWN ART)
Generic focusing module representation
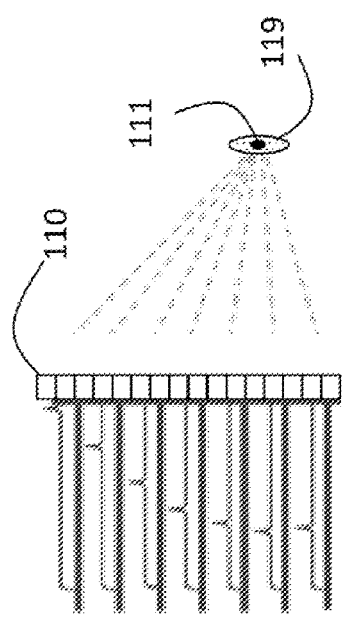
Fig. 23C (KNOWN ART)
Phased-array transducer causing steering and focusing at same time
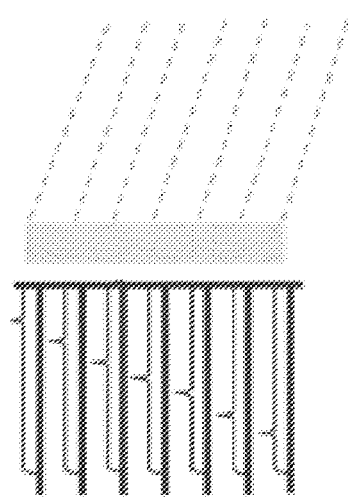
Fig. 23B (KNOWN ART)
Phased-array transducer causing only steering

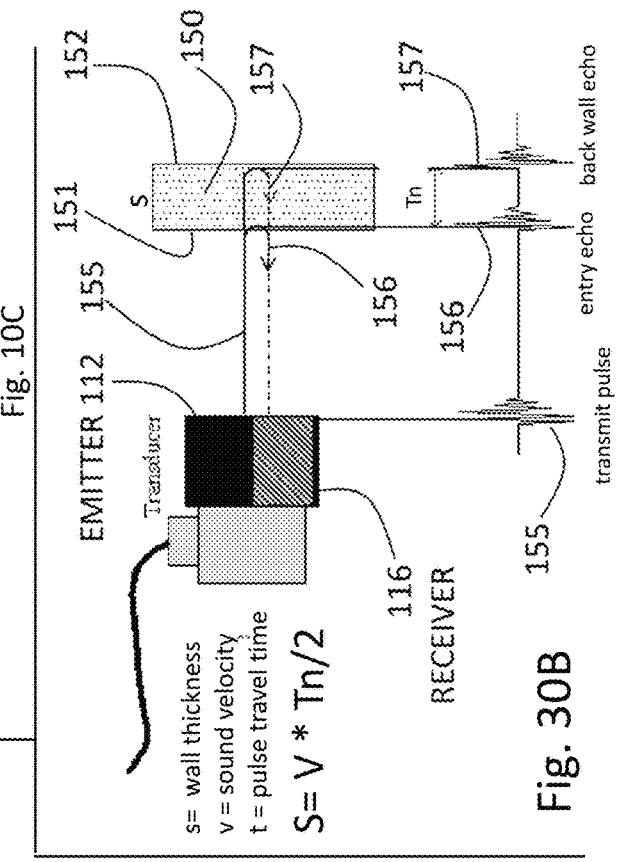
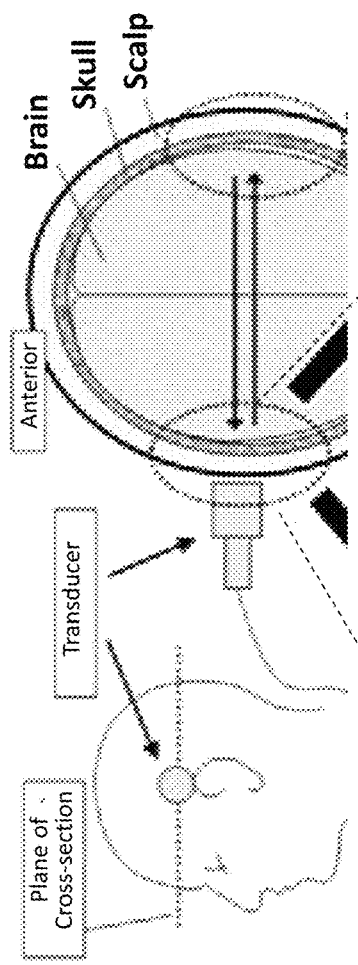
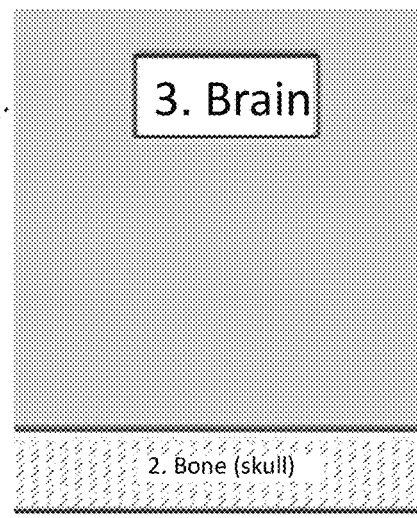
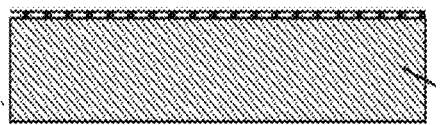

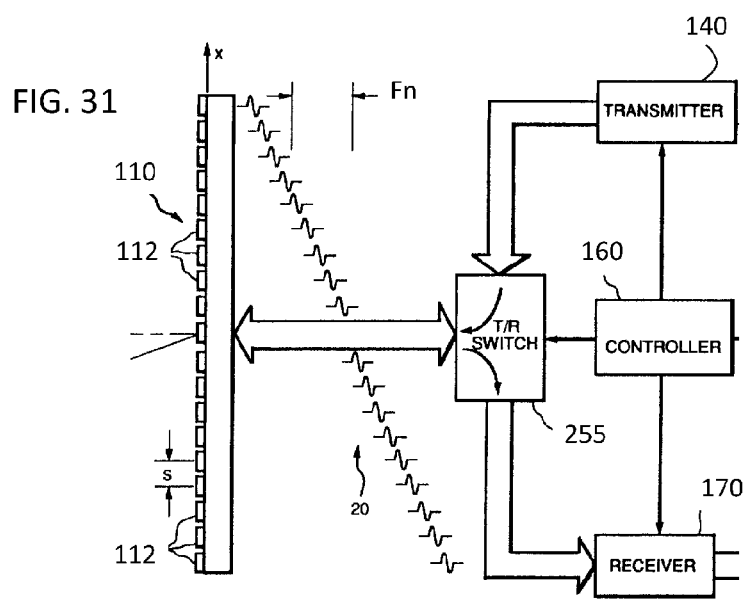

| En Excitation Element | Strongest FR Signal | Strongest BR Signal | TFRn Time of FR [s] | TBRn Time of BR [s] | Tn Time diff [s] | Tn/2 Half time diff [s] | dFn Time shift | Phase Shift |
|---|---|---|---|---|---|---|---|---|
| 1 | 1 | 1 | 1.268E-05 | 1.768E-05 | 5.000E-06 | 2.50E-06 | 4.15E-06 | 298.8 |
| 2 | 2 | 2 | 1.296E-05 | 1.796E-05 | 5.000E-06 | 2.50E-06 | 4.15E-06 | 298.8 |
| 3 | 3 | 3 | 1.320E-05 | 1.820E-05 | 5.000E-06 | 2.50E-06 | 4.15E-06 | 298.8 |
| 4 | 4 | 4 | 1.340E-05 | 1.840E-05 | 5.000E-06 | 2.50E-06 | 4.15E-06 | 298.8 |
| 5 | 5 | 5 | 1.356E-05 | 1.856E-05 | 5.000E-06 | 2.50E-06 | 4.15E-06 | 298.8 |
| 6 | 6 | 6 | 1.372E-05 | 1.872E-05 | 5.000E-06 | 2.50E-06 | 4.15E-06 | 298.8 |
| 7 | 7 | 7 | 1.384E-05 | 1.884E-05 | 5.000E-06 | 2.50E-06 | 4.15E-06 | 298.8 |
| 8 | 8 | 8 | 1.392E-05 | 1.892E-05 | 5.000E-06 | 2.50E-06 | 4.15E-06 | 298.8 |
| 9 | 9 | 8 | 1.396E-05 | 1.852E-05 | 4.560E-06 | 2.28E-06 | 3.78E-06 | 233.1 |
| 10 | 10 | 8 | 1.400E-05 | 1.792E-05 | 3.920E-06 | 1.96E-06 | 3.25E-06 | 137.4 |
| 11 | 11 | 9 | 1.400E-05 | 1.736E-05 | 3.360E-06 | 1.68E-06 | 2.79E-06 | 53.8 |
| 12 | 12 | 12 | 1.396E-05 | 1.700E-05 | 3.040E-06 | 1.52E-06 | 2.52E-06 | 6.0 |
| 13 | 13 | 13 | 1.392E-05 | 1.692E-05 | 3.000E-06 | 1.50E-06 | 2.49E-06 | 0.0 |
| 14 | 14 | 14 | 1.384E-05 | 1.684E-05 | 3.000E-06 | 1.50E-06 | 2.49E-06 | 0.0 |
| 15 | 15 | 15 | 1.372E-05 | 1.672E-05 | 3.000E-06 | 1.50E-06 | 2.49E-06 | 0.0 |
| 16 | 16 | 16 | 1.356E-05 | 1.656E-05 | 3.000E-06 | 1.50E-06 | 2.49E-06 | 0.0 |
| 17 | 17 | 17 | 1.340E-05 | 1.640E-05 | 3.000E-06 | 1.50E-06 | 2.49E-06 | 0.0 |
| 18 | 18 | 18 | 1.320E-05 | 1.620E-05 | 3.000E-06 | 1.50E-06 | 2.49E-06 | 0.0 |
| 19 | 19 | 19 | 1.296E-05 | 1.596E-05 | 3.000E-06 | 1.50E-06 | 2.49E-06 | 0.0 |
| 20 | 20 | 20 | 1.268E-05 | 1.568E-05 | 3.000E-06 | 1.50E-06 | 2.49E-06 | 0.0 |

FIG. 42

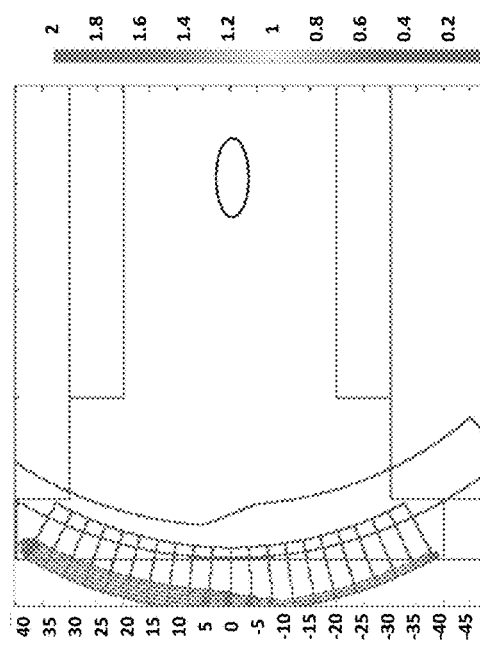
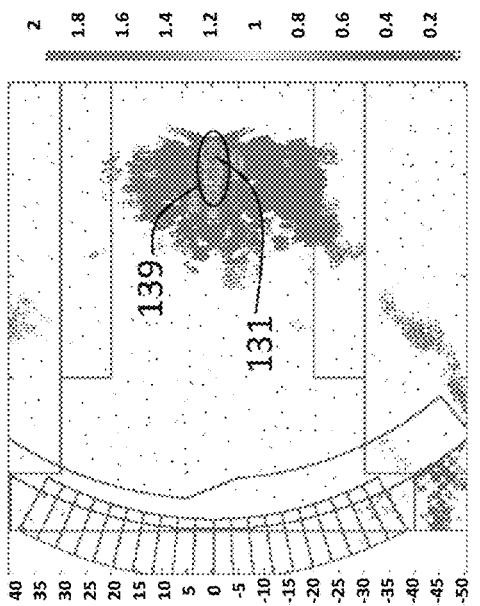
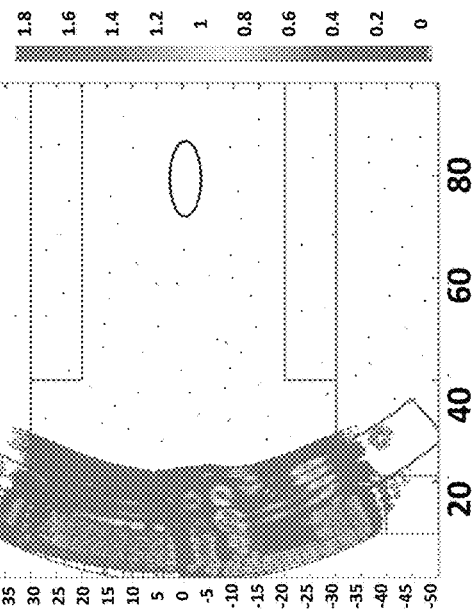

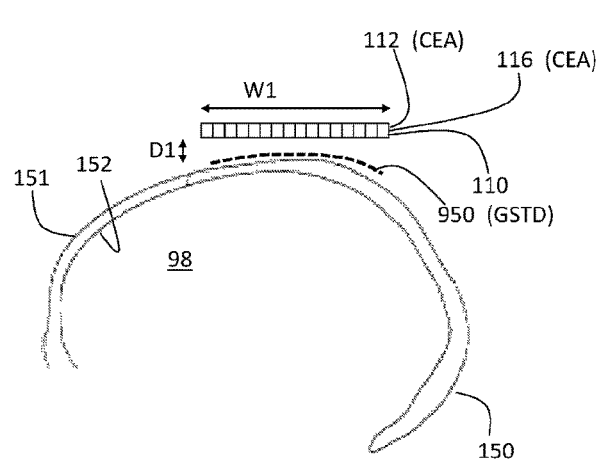
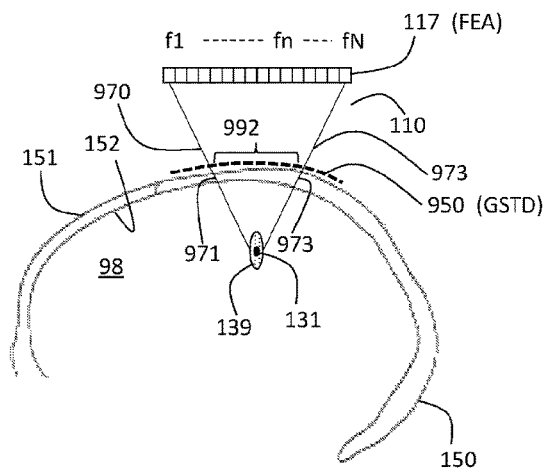
FIG. 45A                    FIG. 45B

TRANSCRANIAL ULTRASOUND FOCUSING

FIELD OF THE INVENTION

Embodiments of the present invention relate to systems and methods for ultrasound focusing. In particular, various embodiments are directed to efficient methods of focusing a phased array of ultrasound transducer elements, using preparatory measurements to adjust the relative phases of the transducer elements.

BACKGROUND OF THE INVENTION

Physics of Ultrasound Transmission: Ultrasounds are mechanical waves (with a frequency of more than 20 kHz) that travel with alternating compression and rarefaction, thereby transmitting energy by molecular movements. In contrast to diagnostic ultrasonography (with a frequency in the megahertz range), the frequencies used for the transcranial FUS are either mid-frequency (e.g., around 650 kHz) or low frequency (e.g., around 220 kHz). The speed of ultrasound transmission is medium dependent (eg, water and soft tissue are excellent conductors, but air and bone are not). Transmission necessitates a coupling medium (eg, degassed water) between the transducer and biological tissue. In addition, there is significant absorption and reflection of ultrasound while traveling through tissues with different "ultrasonic densities," such as layers of the skull (inner table, marrow, and outer table). The extent of ultrasound reflection is also dependent on the incident angle (eg, large (250 to 30°) incident angles result in higher reflection). Besides altering the velocity, heterogeneous tissues also alter the phase of ultrasound waves.

Biological Consequences of Focused Ultrasound

The biological consequences of FUS are dependent on the intensity, frequency, and duration of exposure. At low intensity, high-frequency (2 MHz) ultrasound can produce a reversible conduction block in peripheral nerves. This conduction block is associated with a mild increase in local temperature (41° C. to 45° C.) and is mediated by the inactivation of sodium channels. It can produce transient clinical results that may last for a few minutes and are particularly appealing for target localization in functional neurosurgery. Under certain conditions, FUS can also reversibly open the blood-brain barrier without ablation. Blood-brain barrier opening can be reliably achieved at subthreshold intensities with the use of microbubbles. A recent proof-of-concept study demonstrated localized bloodbrain barrier openings of approximately 1 cm3 with very low sonication power (5 W and 230 kHz transducer).

At high intensity, FUS creates tissue ablation, the mechanism of which is dependent on frequency. For example, the mid-frequency system (650 kHz) primarily produces thermal ablation, whereas the low-frequency system (220 kHz) achieves ablation via cavitation or histotripsy, in which ultrasound interacts with trapped gas bubbles within tissues that leads to the rapid oscillation and collapse of those bubbles. Therapeutic sonications (temperature greater than 55° C.) denature cellular protein and produce lesions with 3 separate zones on T2-weighted MRI: mixed-intensity core (zone 1 with necrotic center), hyperintense periphery (zone 2 with apoptosis), and surrounding vasogenic edema (zone 3). The histological consequences of FUS ablation are associated with the duration of exposure (thermal dose). The target tissue characteristics influence temperature elevation during sonication (eg, tissue perfusion may act as a heat sink, although this reaction is minimal for short-duration sonications).

Nonablative Applications:

As recently reviewed (Vibohr Krishna et al., *JAMA Neurol.* 2018; 75(2)246-254), the ability to transiently open blood-brain barrier in localized brain regions offers a promising route for targeted drug delivery (eg, chemotherapy for neuro-oncology; gene and neurotrophic factors for neurodegenerative diseases. Moreover, targeted drug delivery can be an attractive option for intravascular thrombolysis (eg, in distal intracranial thrombosis where endovascular therapy has met with challenges).

The nonthermal qualities of FUS are attractive for neuromodulation. Successful cortical stimulation using transcranial FUS has been reported in mice (at 650 kHz), patients with chronic pain (at 8 MHz), and healthy volunteers (at 500 kHz). Recently was reported the case of a comatose patient with brain injury who received FUS stimulation to the entire thalamus. The patient showed some clinical improvement without major adverse effects. Finally, subthreshold sonications can be a screening tool for target selection for therapeutic interventions, especially in situations where either conventional screening (eg, levodopa challenge) provides insufficient answers (eg, subthalamic nucleus vs VIM for patients with a dual diagnosis of PD and essential tremor) or the most efficacious target for neuromodulation is unclear (eg, subthalamic nucleus vs globus pallidus internus for patients with PD).

Thermal ablation, as may be accomplished using focused ultrasound, has particular appeal for treating tissue within the brain and other tissue regions deep within the body, because it generally does not disturb intervening or surrounding healthy tissue. Focused ultrasound may also be attractive, because acoustic energy generally penetrates well through soft tissues, and ultrasonic energy, in particular, may be focused towards focal zones having a cross-section of only a few millimeters due to relatively short wavelengths (e.g., as small as 1.5 millimeters (mm) in cross-section at one Megahertz (1 MHz)). Thus, ultrasonic energy may be focused at a region deep within the body, such as a cancerous tumor or other diseased tissue, to ablate the diseased tissue without significantly damaging surrounding healthy tissue.

To focus ultrasonic energy towards a desired target, a piezoelectric transducer may be used that includes a plurality of transducer elements. A controller may provide drive signals to each of the transducer elements, thereby causing the transducer elements to transmit acoustic energy such that constructive interference occurs at a "focal zone". The focal zone is typically defined as the region of intensity higher than half maximum, and is commonly characterized by a "peak width" in a given direction. The peak width may be anisotropic. In fact, most realized instrumental systems produce an elliptical shaped peak cross-section at half maximum. At the focal zone, sufficient acoustic energy may be delivered to generate the desired tissue activation (e.g., heating, necrosis, neural stimulation, etc. . . . ) within the focal zone and for a sufficient period until tissue affects occurs. Preferably, tissue along the path through which the acoustic energy passes ("the pass zone") outside the focal zone, is affected (e.g, heated) only minimally, if at all, thereby minimizing damaging tissue outside the focal zone.

Phased arrays of ultrasound transducers are well-known as a system for focusing ultrasound energy at target sites inside the body. Constructive and destructive interference of acoustic waves transmitted by multiple transducers can be used to deliver complex spatiotemporal patterns of acoustic waves. Generally, phased arrays use tens to hundreds or even thousands of ultrasound transducers distributed spatially on the surface of the body. For instance, a phased array placed on the head can be used to target an area deep in the brain. However, phased arrays have important limitations for delivering ultrasound transcranially for neuromodulation. Phased arrays use spatially distributed transducers, requiring a larger form factor. Moreover, large and generally unportable power and control components are required to manage the timing, intensity, phase, and other properties of the ultrasound waves transmitted by each of the transducers.

The known art of ultrasound focusing onto tissue in general and brain tissue in particular is exemplified in U.S. Pat. Nos. 8,932,237, 5,329,930, 4,817,614, 8,088,067, 6,128,958, 7,611,462, 5,984,881, and references therein, the entire disclosures of which are hereby incorporated by reference.

Focused ultrasound (i.e., acoustic waves having a frequency greater than about 20 kilohertz) can be used to image or therapeutically treat internal body tissues within a patient. For example, ultrasonic waves may be used to ablate tumors, eliminating the need for the patient to undergo invasive surgery. For this purpose, a piezo-ceramic transducer is placed externally to the patient, but in close proximity to the tissue to be ablated (the "target"). The transducer converts an electronic drive signal into mechanical vibrations, resulting in the emission of acoustic waves (a process hereinafter referred to as "sonication"). The transducer may be shaped so that the waves converge in a focal zone. Alternatively or additionally, the transducer may be formed of a plurality of individually driven transducer elements whose phases (and, optionally, amplitudes) can each be controlled independently from one another and, thus, can be set so as to result in constructive interference of the individual acoustic waves in the focal zone. Such a "phased-array" transducer facilitates steering the focal zone to different locations by adjusting the relative phases between the transducers, and generally provides the higher a focus quality and resolution, the greater the number of transducer elements. Magnetic resonance imaging (MRI) may be utilized to visualize the focus and target in order to guide the ultrasound beam.

While the transducer is located external to the patient, it must be in direct contact and tightly coupled with a media that efficiently transmits the high frequency ultrasound waves. For example, the transducer can be positioned in a liquid bath that is capable of efficient transmission of the ultrasound waves. The patient's body must also be wetted and tightly coupled to the transmission media in order to ensure an optimal acoustic wave transmission path from the transducer to the focal zone.

While system parameters are generally fixed for a given transducer array, tissue homogeneity may vary significantly from patient to patient, and even between different tissue regions within the same patient. Tissue inhomogeneity may decrease intensity of the acoustic energy at the focal zone and may even move the location of the focal zone within the patient's body. Specifically, because the speed of sound differs in different types of tissue, as portions of a beam of acoustic energy travel along different paths towards the focal zone, they may experience a relative phase shift or time delay, which may change the intensity at the focal zone and/or move the location of the focal zone.

For example, the speed of sound through fat is approximately 1460 meters per second (m/s), while the speed of sound through muscle is approximately 1600 meters per second (m/s). The speed of sound through bone tissue is much faster, for example, approximately 3000 meters per second (m/s) for skull bone tissue. The speed of sound also varies in different organs. For example, the speed of sound in brain tissue is approximately 1570 meters per second (m/s), approximately 1555 meters per second (m/s) in the liver, and approximately 1565 meters per second (m/s) in the kidney.

The relative phases (alternatively relative "time shift") at which the transducer elements need to be driven to result in a focus at the target location depend on the relative location and orientation of the transducer surface and the target, as well as on the dimensions and acoustic material properties (e.g., sound velocities) of the tissue or tissues between them (i.e., the "target tissue"). Thus, to the extent the geometry and acoustic material properties are known, the relative phases (and, optionally, amplitudes) can be calculated, as described, for example, in U.S. Pat. Nos. 6,612,988, 6,770,031, and 7,344,509, the entire disclosures of which are hereby incorporated by reference. In practice, however, knowledge of these parameters is often too incomplete or imprecise to enable high-quality focusing based on computations of the relative phases alone. For example, when ultrasound is focused into the brain to treat a tumor, the skull in the acoustic path may cause aberrations that are not readily ascertainable. In such situations, treatment is typically preceded by an auto-focusing procedure in which, iteratively, an ultrasound focus is generated at or near the target, the quality of the focus is measured (using, e.g., thermal imaging or acoustic radiation force imaging (ARFI)), and experimental feedback is used to adjust the phases of the transducer elements to achieve sufficient focus quality.

The auto-focusing procedure may thus take a substantial amount of time, which may render it impracticable or, at the least, inconvenient for a patient. While the effect of pretherapeutic sonications may be minimized by employing an imaging technique that requires only low acoustic intensity (e.g., ARFI), it is generally desirable to limit the number of sonications prior to treatment. Accordingly, there is a need for more efficient ways of focusing a phased array of transducer element to create a high-quality ultrasound focus.

Another common technique for focusing ultrasound is by using a shaped lens with an acoustic velocity (i.e. speed of sound) that differs from adjoining air, tissue, or material to bend acoustic waves. Most standard ultrasound focusing lenses employ a single concave lens. However, a single concave lens focusing system for ultrasound has limitations. Ultrasound lenses comprised of a single concave lens are limited with regard to the range of focal lengths that can be achieved with a lens of a particular cross-sectional area. Short focal lengths cannot be achieved with smaller cross-sectional areas appropriate for systems affixed to the head or skull. Neuromodulation of superficial brain regions with an appropriate transcranial ultrasound system would be advantageous due to the importance of such superficial brain regions (e.g. cerebral cortex) to sensory, motor, higher cognitive function, and other brain functions.

To affect brain function transcranial ultrasound neuromodulation requires appropriate ultrasound waveform parameters, including acoustic frequencies generally less than about 10 MHz, spatial-peak temporal-average intensity generally less than about 10 W/cm2 (e.g., between 0.5 and 10 W/cm2), and appropriate pulsing and other waveform characteristics to ensure that heating of a targeted brain region does not exceed about 2 degrees Celsius for more than about 5 seconds. Transcranial ultrasound neuromodulation induces neuromodulation primarily through vibrational or mechanical mechanisms. Noninvasive and nondestructive transcranial ultrasound neuromodulation is in contrast to other transcranial ultrasound based techniques that use a combination of parameters to disrupt, damage, destroy, or otherwise affect neuronal cell populations so that they do not function properly and/or cause heating to damage or ablate tissue.

As by in the article Lindsey (Lindsey B D, Smith S W. Refraction Correction in 3D Transcranial Ultrasound Imaging. *Ultrasonic imaging*. 2014; 36(1):35-54. doi:10.1177/0161734613510287), Image quality in transcranial ultrasound remains limited by the deleterious effects of the presence of the skull, including attenuation, aberration, refraction, and mode conversion. The effects of aberration is induced by spatially inhomogeneous layers having a different longitudinal wave velocity from that typically assumed by the ultrasound scanner (c=1540 m/s). An anatomical sources of aberration include layers of bone in the skull (c≈2800 m/s, commonly within 15% variation due to difference in bone porosity and thickness) or layers of fat (c≈1450).

As discussed in the journal article by Ding et. al., Phys. Med. Biol. 60 (2015) 3975-3998, ultrasound penetration through the skull is better, with less energy deposition within the skull bone itself, at around 0.5 MHz compared with higher frequencies.

A Discussion of FIGS. 1A-2B

FIG. 1A shows human anatomy. Shown in FIG. 1A is (i) a skull 150 having a non-uniform thickness; and (ii) brain tissue 98 therein. Skull 150 has two illustrated surfaces which face away from each other: (i) surface 151 of skull 150 is the outer-facing skull surface which faces away from the brain tissue 98 and towards the outside world; and (ii) surface 152 of skull 150 is the inner-facing skull surface which faces inwardly towards the brain tissue 98.

For the present disclosure, (i) the term outer-facing skull surface is used interchangeably with skull outer surface (or outer skull surface)—the abbreviation SOS may be used and (i) the term inner-facing skull surface is used interchangeably with skull inner surface (or inner skull surface—the abbreviation SIS may be used.

As shown in FIG. 1B, there are some applications where it is desired to deliver focused ultrasound energy to a target location 900 underneath the surface of skull 150 and within brain tissue 98. As illustrated in the figure, target location 900 is located in space at coordinates $(x_{Target}, y_{Target}, z_{Target})$.

Preferably, the delivered energy has as 'tight' of a focus as possible—e.g. most energy is focused at target location 900 within the peak area half-width half-maximum (HWHM).

FIG. 2A illustrates a hypothetical situation where ultrasound is delivered through a unifom medium. In this situation, a spherical array of infinitely small ultrasound transducers produces a perfectly coherent peak such that ultrasound waves emitted form different transducers interfere constructively, which results in a perfect focus at target location 900. In FIG. 2A there is no biological tissue—no skull 150, and no brain tissue 98. In this non-physical hypothetical situation, the focus is perfect.

Unfortunately, as shown in FIG. 2B, in reality it may be impossible to focus all the ultrasound energy at target location 900 within brain tissue 98 using the transducer array of FIG. 2B for a number of reasons including but not limited to the following reasons: (i) the speed of sound is different in the skull 150 than in the brain 98; (ii) the shape of skull 150 is irregular; (iii) the thickness of skull 150 is irregular; (iv) even within the skull 150 the speed of sound is not a constant. Consequently, the phase coherence between ultrasound waves emitted form different transducers is distorted, thereby the focus width may significantly and unpredictably broaden and/or satellite peaks appear which unpredictably reduce the energy within the intended focus peak.

SUMMARY OF EMBODIMENTS

PCT/IB2019/000185 filed on Jan. 31, 2019 is incorporated herein by reference. For example, any claim of PCT/IB2019/000185 remains a part of the present specification. Some embodiments of the invention relate to providing "feature A' and/or "feature B" and/or "feature C" and/or "feature D" and/or "feature E" and/or "feature F" and/or "feature G" and/or "feature H" and/or "feature I," described below in the present section.

Embodiments of the present invention relate to systems and methods for ultrasound focusing. In particular, various embodiments are directed to efficient methods of focusing a phased array of ultrasound transducer elements, using preparatory measurements to adjust the relative phases of the transducer elements.

For the present application, when material (e.g. the skull or brain) is 'irradiated' with ultrasound, this means that ultrasound is delivered to the material (e.g. the skull or brain).

Embodiments of the invention relate to apparatus and methods for generating an ultrasound intensity-peak within a human subject brain around a target peak location in the brain. In particular and not wishing to be bound by theory, embodiments of the present invention overcome any defocusing attributable to: (i) differences in the speed of sound between the skull and underlying brain tissue; (ii) the fact that the skull is of non-uniform thickness; and (iii) the fact that the speed of sound within the skull is not uniform.

Some embodiments are disclosed and claimed in terms of generating an ultrasound intensity-peak within a human subject brain. However, in general terms the presently disclosed teaching may be employed to produce an ultrasound intensity-peak within a generally round object (e.g. having a representative radius curvature of at (i) at least 7 cm or at least 10 cm and/or (ii) at most 50 cm or at most 40 cm or at most 25 cm)(of having: (i) an outer crust (e.g. including but not only skull/bone) having a lower liquid content (e.g. of non-uniform thickness) and (ii) underlying material (e.g. including brain but not only brain) having a greater liquid content. In this case, the ultrasound is delivery from transducers outside of the crust, through the crust, and into the underlying material so as to produce the ultrasound intensity-peak within the underlying material.

In order to counteract defocusing derived from the properties crust (e.g. skull) and/or the underlying material (e.g. brain), transducers disposed outside of the head (e.g. outside of the generally round object) are operated at phase-shifts that are computed by analyzing ultrasound measurement data acquired during a previously-performed calibration stage.

During this calibration stage, the skull (or any other crust) is subjected to plurality of ultrasound skull-probe events (USP) (or an ultrasound crust-probe UCP event for the more general case) where during each USP (or UCP) ultrasound of a respective ultrasound test signal (i.e. produced by ultrasound transducer(s) disposed over the skull or crust).

Instead of only probing a single location on the skull, in order to accurately compute phase-shift data it may be advantageous to probe the skull at a variety of locations on the skull (or other crust), and not just at a single location (Feature A). Furthermore, it is noted that the skull is not a flat plane—the skull is a generally round object, and the local surface orientation of the skull (i.e. the vector perpendicular to a local plane of any given location on the skull or other crust).

In some embodiments, not only is it desired to probe (i.e. with ultrasound of a calibration measurement) the skull (or other crust) at a variety of locations (Feature A) which may be distances from each other (Feature B), but this entails probing the skull or a variety of different local skull-surface orientations (or orientations of any other crust) (Feature C).

For non-binding theoretical reasons explained below, when probing the skull with an ultrasound test signal emitted by one or more of the transducers, it may be advantageous to do so such that an energy flux vector of the ultrasound test signal is substantially perpendicularly incident on the skull (Feature D).

Another feature provided by embodiments of the invention (Feature E) is that ultrasound transducers (i.e. those which participate in the calibration stage as calibration emitters) are held stable for the entirety of the calibration stage.

Thus, in some embodiments, in order to provide Feature D while also providing previous Features A-C and E, it may be useful to:
(I) deliver ultrasound for USP (or UCP event) of the calibration stage so that a majority of power of the respective ultrasound test signal is provided from transducers in a relatively small (e.g. a sphere having a radius at most 0.5 cm locale) locale (Feature F); and/or
(ii) arranged so that these locales are relatively close to the skull (Feature G)—e.g. a center of the 0.5-cm radius spherical locale in which the transducer(s) that provide at least 50% of power of the respective ultrasound signal for the given USP (or UCP) even is displaced from the skull 150 (or other crust) by at most 1.5 or at most 1 cm.

The ultrasound signal of each USP (or UCP event) is received by one or more ultrasound transducers. For each USP (or USP event), a difference in echo times (discussed below) is computed—for example, (i) a time where a signal reflected from the outer surface 151 of skull 150 may be the 'first echo time' and (ii) a time where a signal reflected from the inner surface 151 of skull 150 may be the 'second echo time.' The second echo time may be longer than the first echo time.

In some embodiments of the invention, when measuring the echo time-differences, it is possible to (Feature H) to "re-use" an ultrasound transducer (or a location thereof) which supplies the ultrasound test signal of an USP (or UCP event) by receiving reflected ultrasound back into the same ultrasound transducer or back into another ultrasound transducer displaced therefrom by no more than 0.5 cm. This may be carried out for at least one or at least some or at least a majority of the USP (or UCP events). In some examples, this may increase the accuracy and facilitate computation of face-differences that are useful for achieving a better focus.

In some embodiments of the invention, when producing the ultrasound-intensity peak within the brain beneath the skull (or other material beneath the crust), it may be possible to (Feature 1) to "re-use" an ultrasound transducer (or a location thereof) which supplies the ultrasound test signal of an USP (or UCP event) during calibration. Thus, when operating transducers according using the computed phase-shifts to produce this ultrasound-intensity peak, at least some of the transducers (or some of the locales) deliver may be same as those used to probe the skull during the USP (or UCP) event of calibration.

Thus, embodiments of the present invention relate to delivery of ultrasound (e.g. non-surgically—i.e. non-invasively).

A method for generating an ultrasound intensity-peak within a human subject brain around a target-peak-location, by delivering ultrasound through the skull, the method comprising:
a. providing an array of ultrasound transducers (AUT);
b. operating at least some transducers of the AUT in calibration mode to subject the skull to at least L ultrasound skull-probe (USP) events {USP-event$_1$, USP-event$_2$ ... USP-event$_L$} (L is a positive integer; L≥5) such that:
(i) during each USP-event$_i$, a respective ultrasound test signal UTS$_i$ emitted by one or more transducer(s) of the AUT probes the skull to produce a maximum intensity at a different respective event-specific skull-surface location max_intensity_SOS_LOC (USP-event$_i$) that is on the skull outer-facing surface and specific for the event USP-event$_i$;
(ii) each USP-event$_i$ is defined by a different respective dominant emission-locale DEL(USP-event) such that during each USP-event$_i$ at least 20% or at least 30% or at least 50% of power of the respective ultrasound test signal UTS$_i$ received at the respective skull-surface location max_intensity_SOS_LOC (USP-event$_i$) on the skull is supplied by transmitter(s) of the AUT whose center(s) is(are) disposed within the dominant emission-locale DEL (USP-event$_i$), the dominant emission-locale DEL (USP-event$_i$) being spherical in shape with a radius of at most 0.75 cm or at most 0.5 cm;
(iii) the dominant emission locales are distributed in space so that no two dominant emission locales (DEL(USP-event$_j$), DEL(USP-event$_k$)] (j≠k) (both j and k are positive integers equal to at most L) are displaced from each other to have a center-center distance of less than 2 cm (alternatively, for every pair of two dominant emission locales (DEL(USP-event$_j$), DEL(USP-event$_k$)](j≠k) (both j and k are positive integers equal to at most L, a center-center distance therebetween is at least 2 cm); and
c. for each USP-event$_i$ having its respective ultrasound test signal UTS$_i$ and its respective dominant emission-locale DEL(USP-event), respectively receiving ultrasound reflected from the skull during the USP-event$_i$ into a respective one or more of the transducer(s) of the AUT;
d. electronically processing output of the transducer(s) which receive the reflected ultrasound from each USP-event$_i$; and
e. operating at least some transducers of the AUT in relative phases determined from the results of the electronic processing of step (d) so as to generates the ultrasound intensity-peak within the human subject brain around the target-peak-location 900.

In some embodiments, the electronic processing comprises for each USP-event$_i$ having its respective ultrasound test signal UTS$_i$ and its respective dominant emission-locale DEL(USP-event$_i$), computing a respective measured echo time-difference ETD(USP-event$_i$) between:
(i) a first measured time T$_1$(USP-event$_i$) at which the respective ultrasound test signal UTS$_i$ received by one of the transducers of the array;

(ii) a second measured time $T_2(\text{USP-event}_i)$ at which the respective ultrasound test signal $UTS_i$ received by the same one or a different one of the transducers of the array.

A method for generating an ultrasound intensity-peak within a human subject brain around a target-peak-location 900, by delivering ultrasound through the skull, the method comprising:

a. providing an array of ultrasound transducers (AUT);

b. operating at least some transducers of the AUT in calibration mode to subject the skull to at least L ultrasound skull-probe (USP) events P120 {USP-event$_1$, USP-event$_2$ . . . USP-event$_L$} (L is a positive integer; L≥5) such that:

(i) during each USP-event$_i$, a respective ultrasound test signal $UTS_i$ emitted by one or more transducer(s) of the AUT probes the skull to produce a maximum intensity at a different respective event-specific skull-surface location max_intensity_SOS_LOC (USP-event$_i$) that is on the skull outer-facing surface on specific for USP-event$_i$;

(ii) each USP-event$_i$ is defined by a different respective dominant emission-locale DEL(USP-event$_i$) such that during each USP-event$_i$ at least 20% or at least 30% or at least 50% of power of the respective ultrasound test signal $UTS_i$ received at the respective skull-surface location max_intensity_SOS_LOC (USP-event$_i$) on the skull is supplied by transmitter(s) of the AUT whose center(s) is(are) disposed within the dominant emission-locale DEL (USP-event$_i$), the dominant emission-locale DEL (USP-event$_i$) being spherical in shape with a radius of at most 0.75 cm or at most 0.5 cm;

(iii) the dominant emission locales are distributed in space so that no two dominant emission locales (DEL(USP-event$_j$), DEL(USP-event$_k$)] (j≠k) (both j and k are positive integers equal to at most L) are displaced from each other to have a center-center distance of less than 2 cm (alternatively, for every pair of two dominant emission locales (DEL(USP-event$_j$), DEL(USP-event$_k$)] (j≠k) (both j and k are positive integers equal to at most L, a center-center distance therebetween is at least 2 cm);

c. for each USP-event$_i$ having its respective ultrasound test signal $UTS_i$ and its respective dominant emission-locale DEL(USP-event$_i$), measuring a respective echo time-difference ETD(USP-event$_i$) between:

(i) a first measured time $T_1(\text{USP-event}_i)$ at which the respective ultrasound test signal $UTS_i$ received into one of the transducers of the array;

(ii) a second measured time $T_2(\text{USP-event}_i)$ at which the respective ultrasound test signal $UTS_i$ received into the same one or a different one of the transducers of the array; and d. operating at least some transducers of the AUT in focus-around-target-peak-location (FATPL) mode to simultaneously irradiate the skull, wherein step (d) is performed such that:

A. the at least some transducers deliver ultrasound in at relative phases computed from the echo time-differences measured in step (c); and B. the delivering of ultrasound from the at least some transducers generates the ultrasound intensity-peak within the human subject brain around the target-peak-location 900.

In some embodiments, the respective skull-surface locations max_intensity_SOS_LOC(USP-event$_i$) on the skull outer-facing surface form a location set SOS_LOC_SET {max_intensity_SOS_LOC((USP-event$_1$), max_intensity_SOS_LOC((USP-event$_2$) . . . max_intensity_SOS_LOC ((USP-event$_L$)}, and wherein the skull-surface locations of the location set SOS_LOC_SET are distributed in space so that no two skull-surface locations (max_intensity_SOS_LOC(USP-event$_j$), max_intensity_SOS_LOC(USP-event$_j$)) on the skull outer-facing surface are displaced from each other by less than disp_numb cm, wherein disp_numb is a positive number whose value is at least 1 or at least 1.5 or at least 2.

In some embodiments, for each event USP-event$_i$ of the L events of {USP-event$_1$, USP-event$_2$ . . . USP-event$_L$}, a center of the respective dominant emission-locale DEL (USP-event$_i$) thereof is displaced from the skull by at most 2.5 cm.

In some embodiments, for each event USP-event$_i$ of the L events of {USP-event$_1$, USP-event$_2$ . . . USP-event$_L$}, a center of the respective dominant emission-locale DEL (USP-event$_i$) thereof is displaced from the skull by at most 2 cm or at most 1.5 cm.

In some embodiments, a nearest distance between (i) the target-peak-location 900 in brain tissue 98 beneath the skull and (ii) the skull is at least 2 cm or at least 4 cm or at least 5 cm.

In some embodiments, wherein each USP-event$_i$ is defined by a different respective dominant emission-locale DEL(USP-event$_i$) such that during each USP-event$_i$ the at least 50% of power of the respective ultrasound test signal $UTS_i$ received at the respective skull-surface location max_intensity_SOS_LOC(USP-event$_i$) on the skull is supplied by the transmitter(s) of the AUT (i) whose center(s) is(are) each disposed within a dominant emission-locale DEL(USP-event$_i$) that is spherical in shape with a radius of at most 0.5 cm; and (ii) which each have a width of at most ww cm, wherein 0≤ww≤1.

In some embodiments, wherein 0≤ww≤0.75.

In some embodiments, wherein 0≤ww≤0.5.

In some embodiments, wherein L≥7 or L≥8 or L≥10.

In some embodiments, wherein for each event USP-event$_i$ of the L events of {USP-event$_1$, USP-event$_2$ . . . USP-event$_L$}, the respective one of more transducer(s) which:

(i) receive the skull-reflected ultrasound and (ii) whose output is electronically processed to determine the relative phase used to generate the ultrasound intensity peak, are each disposed in the respective dominant emission-locale DEL(USP-event$_i$) for the event USP-event$_i$.

In some embodiments, wherein the dominant emission locales are distributed in space so that a center-center distance between a first DEL(USP-event$_j$) and a second DEL(USP-event$_k$) of the dominant emission locales (j≠k) (i.e. for two different events) is at least 4 cm or at least 5 cm.

In some embodiments, at least 30% of ultrasound power of the intensity peak are supplied by transducer(s) disposed with any of the dominant emission-locales {DEL(USP-event$_1$), DEL(USP-event$_2$) . . . DEL(USP-event$_L$)} defined by the at least L ultrasound skull-probe (USP) events {USP-event$_i$, USP-event$_2$ . . . USP-event$_L$}

In some embodiments, wherein at least 50% (or at least 75%) of ultrasound power of the intensity peak are supplied by transducer(s) disposed with any of the dominant emission-locales {DEL(USP-event$_1$), DEL(USP-event$_2$) . . . DEL(USP-event$_L$)} defined by the at least L ultrasound skull-probe (USP) events {USP-event$_1$, USP-event$_2$ . . . USP-event$_L$}

In some embodiments, the ultrasound intensity-peak produced by operating the at least some transducers in the relative phases produces the intensity-peak so that a FWHM full width half maximum thereof in a widest dimension (e.g. of an oval-shaped peak) is at most 5 cm or at most 4 cm.

In some embodiments, the ultrasound intensity-peak produced by operating the at least some transducers in the relative phases produces the intensity-peak so that a FWHM full width half maximum thereof in a most narrow dimension (e.g. of an oval-shaped peak) is at most 2.5 cm or at most 2 cm or at most 1.5 cm or at most 1 cm.

In some embodiments, at least a majority of or at least 75% of or all ultrasound transducers employed to transmit ultrasound during calibration mode remain stationary during a time period which begins upon commencement of the operation in the calibration mode and concludes upon generation of the ultrasound intensity-peak.

In some embodiments, at least a majority of or at least 75% of or all ultrasound transducers operated according to the relative phases to form the intensity-peak remain stationary during a time period which begins upon commencement of the operation in the calibration mode and concludes upon generation of the ultrasound intensity-peak.

A system for generating an ultrasound intensity-peak within a human subject brain around a target-peak-location, by delivering ultrasound through the skull, the method comprises:
a. an array of ultrasound transducers (AUT);
b. a mechanical arrangement for holding transducers in fixed locations and/or orientations relative to each other according to a defined geometry;
c. a data processing unit for processing output generated by transducer(s) of the AUT in response to ultrasound; and
d. control circuitry responsive to output of the data processing unit and configured to control operation of the AUT when the transducers thereof are in proximity of the skull and held relative to each other by the mechanical arrangement at their defined geometry so as to operate the AUT either in calibration-mode or in sub-surface energy-focus (SSEF) mode, wherein:
A. when the AUT is in calibration-mode, the control circuitry causes at least some transducers of the AUT to subject the skull to at least L ultrasound skull-probe (USP) events {USP-event$_1$, USP-event$_2$ ... USP-event$_L$} (L is a positive integer; L≥5) such that:
(i) during each USP-event$_i$, a respective ultrasound test signal UTS$_i$ is emitted by one or more transducer(s) so as to probes the skull to produce a maximum intensity at a different respective skull-surface location max_intensity_SOS_LOC(USP-event$_i$) on the skull outer-facing surface;
(ii) each USP-event$_i$ is defined by a different respective dominant emission-locale DEL(USP-event$_i$) such that during each USP-event$_i$ at least 20% or at least 30% or at least 50% of power of the respective ultrasound test signal UTS$_i$ received at the respective skull-surface location max_intensity_SOS_LOC (USP-event) on the skull is supplied by transmitter(s) of the AUT whose center(s) is(are) disposed within the dominant emission-locale DEL(USP-event$_i$), the dominant emission-locale DEL(USP-event$_i$) being spherical in shape with a radius of at most 0.75 cm or at most 0.5 cm;
(iii) the dominant emission locales are distributed in space so that no two dominant emission locales (DEL(USP-event$_j$), DEL(USP-event$_k$)] (j≠k) (both j and k are positive integers equal to at most L) are displaced from each other to have a center-center distance of less than 2 cm (alternatively, for every pair of two dominant emission locales (DEL (USP-event$_j$), DEL(USP-event$_k$)] (j≠k) (both j and k are positive integers equal to at most L, a center-center distance therebetween is at least 2 cm);
(iv) for each USP-event$_i$, ultrasound reflected from the skull is received by a respective one or more of the transducers of the AUT to generate electrical output therefrom;
B. the data processing unit processes the electrical output to computed therefrom relative phases between different ultrasound transducers;
C. when the AUT is in SSEF mode, the control circuitry causes at least some of the transducers of the AUT to emit simultaneously emit ultrasound according to the relative phases that were computed by the data processing unit so as to generate the ultrasound intensity-peak within a human subject brain around the target-peak-location 900.

A system for generating an ultrasound intensity-peak within a human subject brain around a target-peak-location, by delivering ultrasound through the skull, the method comprises:
a. an array of ultrasound transducers (AUT);
b. a data processing unit for processing output generated by transducer(s) of the AUT in response to ultrasound; and
c. control circuitry responsive to output of the data processing unit and configured to control operation of the AUT when the transducers thereof are in proximity of the skull so as to operate the AUT either in calibration-mode or in sub-surface energy-focus (SSEF) mode, wherein:
A. when the AUT is in calibration-mode, the control circuitry causes at least some transducers of the AUT to subject the skull to at least L ultrasound skull-probe (USP) events {USP-event$_1$, USP-event$_2$ ... USP-event$_L$} (L is a positive integer; L≥5) such that:
(i) during each USP-event$_i$, a respective ultrasound test signal UTS$_i$ is emitted by one or more transducer(s) so as to probes the skull to produce a maximum intensity at a different respective skull-surface location max_intensity_SOS_LOC(USP-event$_i$) on the skull outer-facing surface;
(ii) each USP-event$_i$ is defined by a different respective dominant emission-locale DEL(USP-event$_i$) such that during each USP-event$_i$ at least 20% or at least 30% or at least 50% of power of the respective ultrasound test signal UTS$_i$ received at the respective skull-surface location max_intensity_SOS_LOC (USP-event$_i$) on the skull is supplied by transmitter(s) of the AUT whose center(s) are disposed within a dominant emission-locale DEL(USP-event) that is spherical in shape with a radius of at most 0.5 cm;
(iii) the dominant emission locales are distributed in space so that no two dominant emission locales (DEL(USP-event$_j$), DEL(USP-event$_k$)] (j≠k) (both j and k are positive integers equal to at most L) are displaced from each other to have a center-center distance of less than 2 cm;

(iv) for each USP-event$_i$, ultrasound reflected from the skull is received by a respective one or more of the transducers of the AUT to generate electrical output therefrom;

B. the data processing unit processes the electrical output to computed therefrom relative phases between different ultrasound transducers;

C. when the AUT is in SSEF mode, the control circuitry causes at least some of the transducers of the AUT to emit simultaneously emit ultrasound according to the relative phases that were computed by the data processing unit so as to generate the ultrasound intensity-peak within a human subject brain around the target-peak-location 900.

In some embodiments, each USP-event$_i$ respectively defines an event-specific direction of an energy flux vector EFV(USP-event$_i$) describing the directional energy flux of the USP signal incident upon the skull outer surface to thereby defined an EVF set {EVF(USP-event$_1$), EVF(USP-event$_2$) ... EVF(USP-event$_L$)} such that all EVF vectors of a sub-set of the EVC set are rotated from each other by at least 15 degrees, a cardinality of the sub-set being at least two.

42. The method or system of claim 41 wherein the cardinality is at least 3 or at least 5.

43. The method or system of any of claims 41-42 wherein each of {EVF(USP-event$_1$), EVF(USP-event$_2$) ... EVF(USP-event$_L$)} is substantially aligned with a local orientation of max_intensity_SOS_LOC(USP-event$_i$) within at most 10 degrees or at most 5 degrees.

For the present disclosure, any "circuitry" or "module" or ""unit" may be implemented using any combination of hardware (e.g. a general purpose CPU or any other analog or digital hardware) and/or software and/or firmware.

A mechanical arrangement may include, for example, a device housing or other components that the skilled artisan would employ after reading the present disclosure.

BRIEF DESCRIPTION OF THE DRAWINGS

A presently preferred embodiment of the invention will be described in detail, in conjunction with the accompanying drawings, in which:

FIGS. 3-20 illustrate various embodiments of the invention.

FIG. 21 illustrates an embodiment of the invention system.

FIGS. FIG. 22A, 22B, 22C illustrate schematic embodiments of focusing transducer arrays.

FIG. 22E illustrates a known art system of focusing array.

FIG. 22D illustrate a two-dimensional transducer array.

FIGS. 23A and 23B illustrate steering option of transducer array.

FIG. 23C illustrates schematic embodiments of focusing transducer arrays.

FIGS. 30A and 30B illustrate aspects of the echo detection mechanism used in the present invention.

FIG. 31 highlights the switching control module.

FIGS. 40 to 43 present the planning and data of a numerical simulation realization example of the present invention.

FIGS. 45A, 45B and 45C illustrate an embodiment where the calibration emitters array and the focusing emitters array are situated at different location with respect to the skull.

DETAILED DESCRIPTION OF EMBODIMENTS

The invention is herein described, by way of example only, with reference to the accompanying drawings. With specific reference now to the drawings in detail, it is stressed that the particulars shown are by way of example and for purposes of illustrative discussion of the embodiments of the exemplary system only and are presented in the cause of providing what is believed to be a useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how several forms of the invention may be embodied in practice and how to make and use the embodiments.

Figure 3:
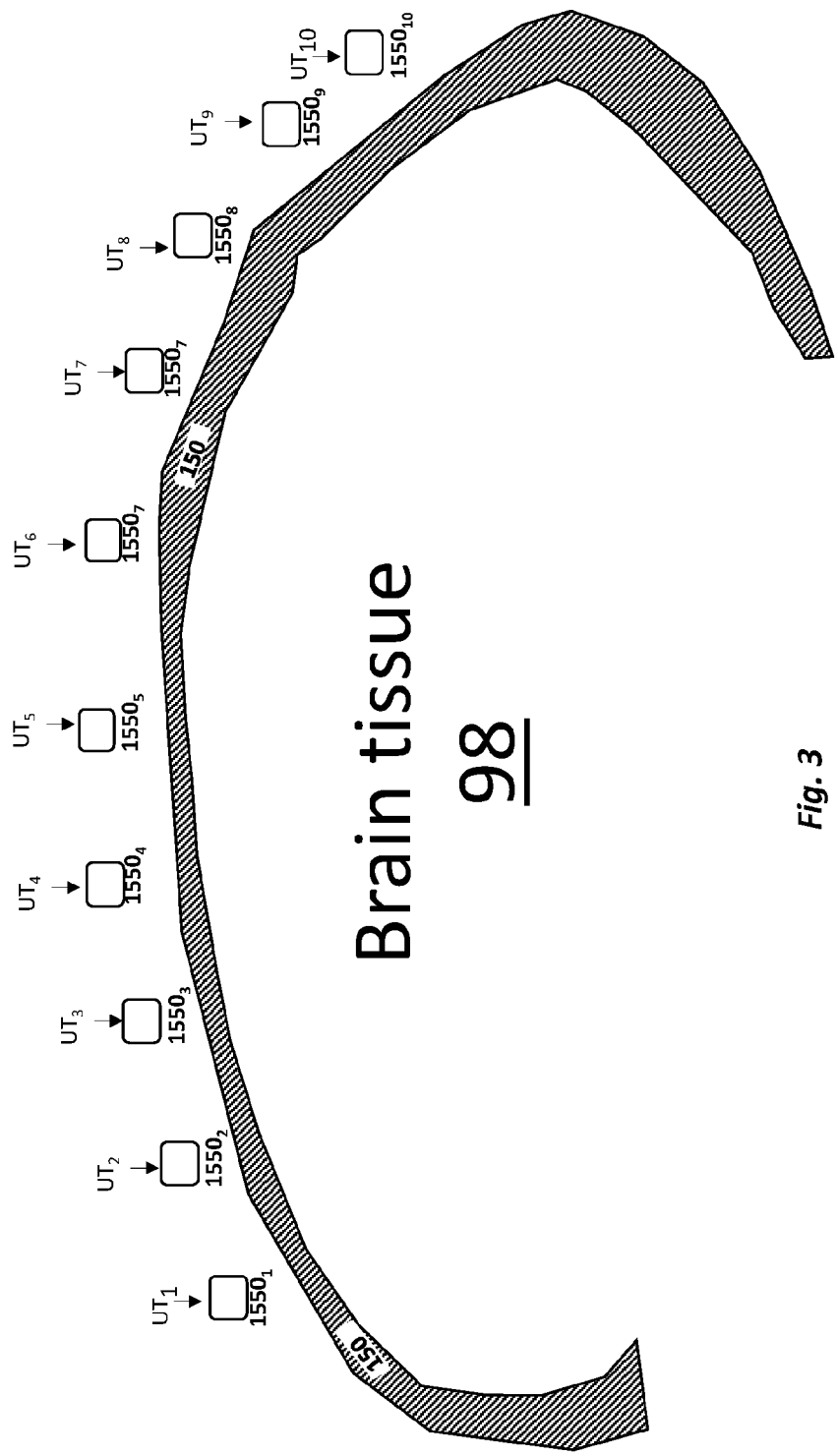

FIG. 3 illustrates an array of ultrasound transducers (AUT) comprising 10 ultrasound transducers $UT_1$-$UT_{10}$. The skilled artisan can appreciate that the in different embodiments, more or or fewer ultrasound transducers (AUT) may be provided. The ultrasound transducers are labelled both as $UT_1$-$UT_{10}$ and as $1550_1$-$1550_{10}$.

It is possible to emit an ultrasound signal in vicinity of the skull 150 using one or more transducers 1550. For example, the transducer 1550 emits an ultrasound test signal which propagates in space, reaches skull 150, and echoes from the skull. The echoed ultrasound may be subsequently detected by the same transducer or by a different transducer.

Not shown in FIG. 3 are optional and impedance matching material.

A Discussion of FIGS. 4-7D

FIG. 4 illustrates one simple example of an ultrasound test signal and FIGS. 5A-5E illustrate reflecting the ultrasound test signal from the skull 150. At time $t_A$, transducer 1550A emits the ultrasound test signal, which propogates in space and is incident upon outer surface 151 of skull at time $t_B$ (see FIG. 5B). At this time $t_B$, a first portion of ultrasound energy of the ultrasound test signal reflects back towards transducer 1550A, and a second portion of ultrasound energy of the ultrasound test signal continues through skull 150 towards brain tissue 98. Once this second portion of ultrasound energy reaches the inner surface 152 of skull 150 at time $t_C$ (see FIG. 5C), at least some energy of this second portion reflects back towards transducer 1550A.

Figure 6:
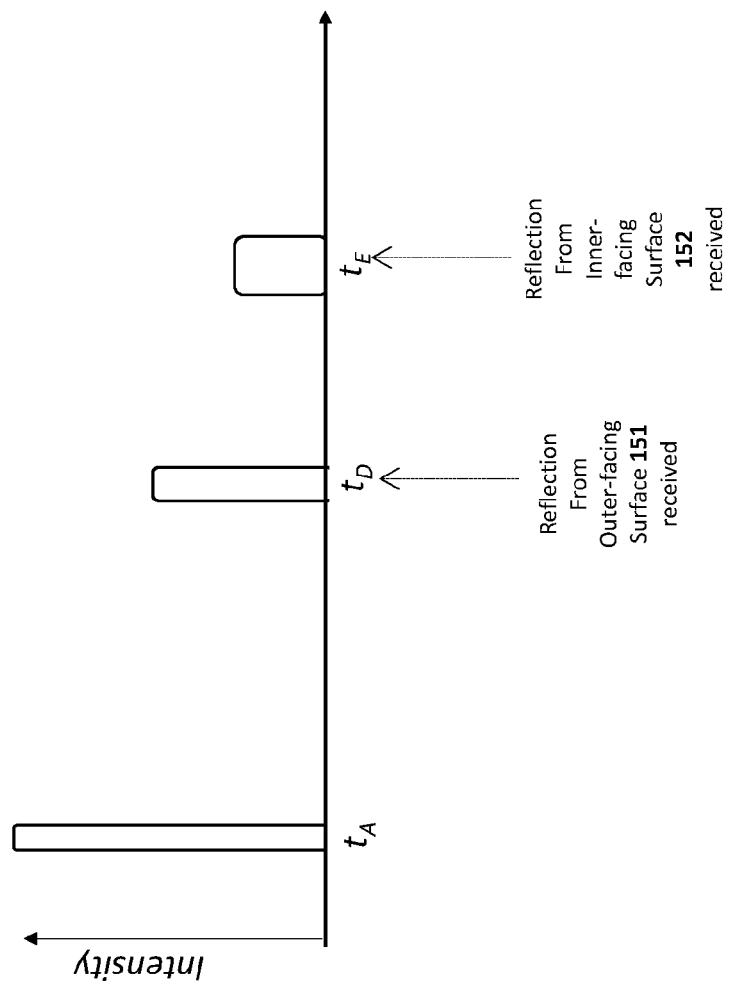

As shown in FIGS. 5D-5E and 6:
(i) At time $t_D$, ultrasound energy which was reflected from the outer surface 151 of skull (i.e. at time $t_B$) is received by transducer 1550A-thus, a first echo of the ultrasound test signal of FIG. 4 is detected at transducer 1550A at a time-delay of $(t_D-t_A)$ after the ultrasound test signal is initially emitted by transducer at $t_A$. This corresponds to the time required for ultrasound to traverse the 'optical path' having first and second legs illustrated in FIG. 7A;
(ii) At time $t_E$, ultrasound energy which was reflected from the inner surface 152 of skull (i.e. at time $t_C$) is received by transducer 1550A—thus, a second echo of the ultrasound test signal of FIG. 4 is detected at transducer 1550A at a time-delay of $(t_E-t_A)$ after the ultrasound test signal is emitted by initially emitted by transducer at $t_A$. This corresponds to the time required for ultrasound to traverse the 'optical path' having first and second legs illustrated in FIG. 7B.

The time delay $(t_E-t_D)$ (i.e. the delay between receiving of reflected ultrasound in FIG. 5D a first echo and the receiving of ultrasound in FIG. 5E a second echo) is indicative of a combination of (i) the speed of sound within skull 150; and (ii) the thickness thereof at the location where ultrasound of the ultrasound test signal (i.e. created at time by $t_A$ transducer 1550A). In some embodiments, this may be related to an angle between:
(i) a normal vector of surface 151 where ultrasound is incident thereon at time $t_B$;
(ii) a directional energy flux vector (analogous to a Poynting vector from electricity and magnetism) of the ultrasound test signal when is incident thereon at time $t_B$.

In the example of FIGS. 5A-5E, 7A-7B, these two vectors are aligned with each other. This is in contrast to the example of FIGS. 7C-7D using transducer 1550B, where it may be more difficult to accurately measure the thickness of skull 150 (though a measurement still can be acquired).

A Multi-Stage Method for Generating an Ultrasound Intensity-Peak: Preliminary Discussion of FIG. 8

Figure 8:
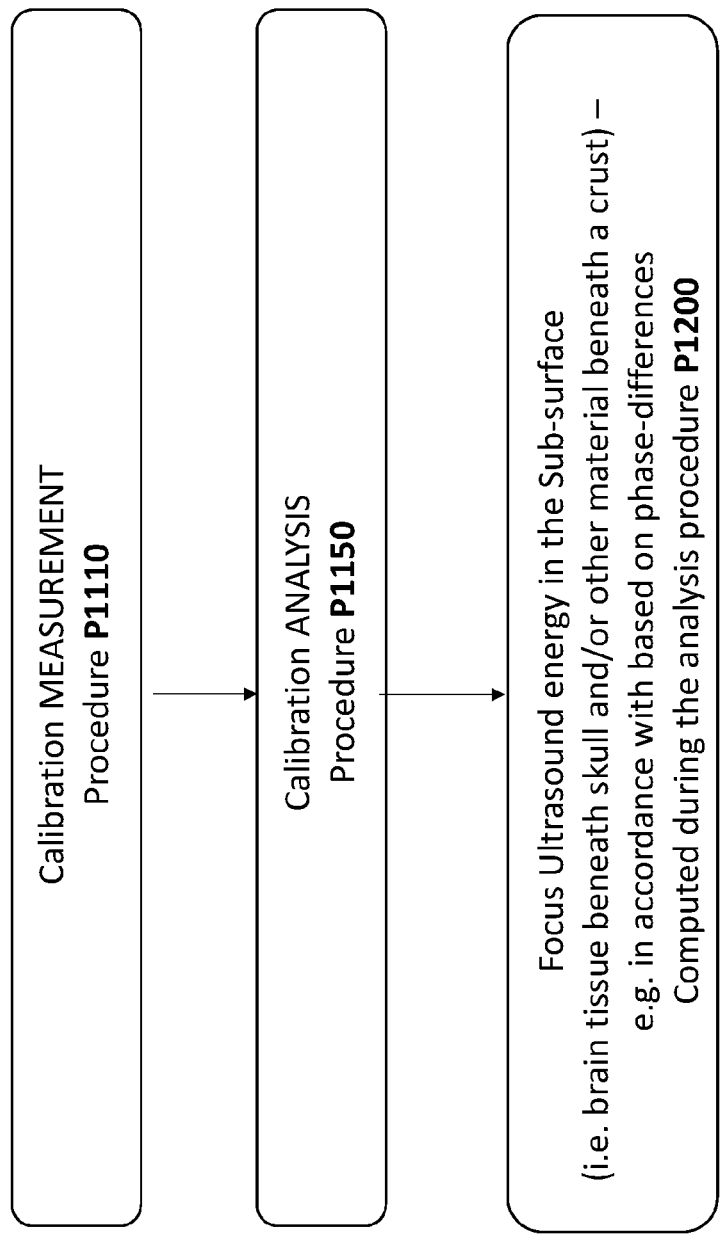

Reference is made to FIG. 8 which is a method for generating an ultrasound intensity-peak within a human subject brain around a target-peak-location 900, by delivering ultrasound through the skull 150. This is shown in the last step of FIG. 8 (i.e. step P1200) where a plurality of ultrasound transducers are operated using computed relative phase differences that are computed in earlier steps (e.g. in accordance with the speed of sound in skull tissue and/or brain tissue and/or in accordance with relationship (e.g. ratio) therebetween).

Specifically, in order to compute the phase-differences, a calibration measurement procedure P1110 and a calibration analysis procedure P1150 are first performed.

Embodiments of the invention relate to features of the calibration measurement procedure P1110. In particular, in some embodiments, the measurement procedure is performed using (i) ultrasound transducers (i.e. of an ultrasound array) where the transducers are each very "close" to the surface of skull outer surface 151; and/or (ii) employed to produce a plurality of ultrasound-probe events (discussed below), where for each ultrasound-probe event In some embodiments, the term 'very close' to the skull (or another generally round object) may be relative to one or more of (i) the size/width of the array used in the calibration measurement procedure P1110 and/or (ii) the radius of curvature (or variations thereof) of the skull and/or of a target portion thereof.

For example, each ultrasound skull-probe (USP) event (described below) may be performed by delivering ultrasound primarily (i.e. on a per-event basis) from transducer(s) whose respective centers are:
(A) located within 3 cm or within 2 cm of the outer skull-surface;
(B) localized within a very small locale (referred to as a dominant emission locale and discussed below—e.g. each locale may be defined by a sphere having a radius of at most 1 cm or at most 0.5 cm.

Not wishing to be bound by theory, providing one or both of these features may be useful for delivering ultrasound such that (i) a normal vector at a location of surface 151 where the ultrasound test signal is incident is substantially aligned with (ii) a directional energy flux vector (analogous to a Poynting vector from electricity and magnetism) of the ultrasound test signal used to generate ultrasound skull-probe (USP) event (described below). This may be useful, in some examples, for achieving a situation similar to that of FIGS. 7A-7B.

A Discussion of Steps P1110, P1150 and P1200 of FIG. 8

In the non-limiting example illustrated in FIG. 8, the method comprises three steps (each of which is discussed below in greater details):

A. a calibration MEASUREMENT procedure P1110. For example (and without limitation), this procedure P1110 (e.g. together with at least some analysis P1120) may measure an indication of a (i) a thickness of skull 150 as a function of location on the skull and/or (ii) a speed of sound within the skull 150. The physical data acquired during the measurement procedure P1110 is subsequently processed in the calibration ANALYSIS procedure P1150 to compute relative phases used in step P1200 (e.g. for overcoming inhomogeneities in skull thickness and/or in acoustic properties of the skull and/or brain).

As will be discussed below, the calibration MEASUREMENT procedure P1110 may be described with reference to ultrasound skull-probe (USP) events, discussed below. For each USP event, a respective ultrasound test-signal (e.g. see FIG. 4; other examples are in FIG. 12A-12B or 18-20) is emitted.

B. a calibration ANALYSIS procedure P1150—for example, measurement data may be used to determine an echo-time difference. The echo time-difference may be related to the time delay $(t_E-t_D)$ discussed above with reference to FIGS. 4-6. Without limitation, this echo time-difference may describe a combination of (i) the speed of sound within skull 150 or particular portion(s) thereof; and (ii) the thickness thereof at the location at particular location(s).

The analysis procedure may also comprise computation of relative phases used in step P1200 (e.g. for overcoming inhomogeneities in skull thickness and/or in acoustic properties of the skull and/or brain).

C. a sub-surface focus procedure P1200. Once the relative phases are computed in P1150, they are employed in the focus procedure P1200 where a plurality of ultrasound transducers (i.e. either the same transducers used in P1110 or different transducers) emit ultrasound according to the computed relative phases. In embodiments of the invention, P1200 may be performed such that:

(i) ultrasound transducers operated in P1200 deliver ultrasound in at relative phases computed from the echo time-differences measured in P1150; and/or (ii). the delivering of ultrasound from the at least some transducers generates the ultrasound intensity-peak within the human subject brain around the target-peak-location 900.

USP Events

In embodiments of the invention, during P1110 a plurality of Ultrasound probe (USP) events {USP-event$_1$, USP-event$_2$ ... USP-event$_L$} are performed. In some embodiments, L≥5. In some embodiments, L≥7. In some embodiments, L≥8. In some embodiments, L≥10.

Each USP event USP-event$_i$ (1≤i≤L) is characterized by:

(i) ultrasound test signal—an ultrasound test signal transmitted to the skull by one or more transmitter(s). As discussed below, the ultrasound test signals may be the same for some or all events or they may be event-specific.

(ii) maximum intensity location max_intensity_SOS_LOC(USP-event$_i$) on the skull outer surface specific for the USP event USP-event$_i$—SOS is an abbreviation for skull outer surface 151. The maximum intensity location max_intensity_SOS_LOC(USP-event$_i$) is a location on the skull outer surface 151 where the intensity of the ultrasound test signal (i.e. when received at the skull) is greater than the intensity at any other location on the skull outer surface 151. This location is the 'maximum intensity' location on the skull outer surface. NOTE—this 'maximum intensity' location is not necessarily the maximum compared to all locations of space. Rather, the 'maximum intensity' is compared to only to other locations on the outer surface 151 of the skull 150.

This 'maximum intensity location' is event specific—a different one for each USP event. Thus, the set of Ultrasound probe (USP) events {USP-event$_1$, USP-event$_2$ ... USP-event$_L$} defined as set of maximum intensity locations {max_intensity_SOS_LOC(USP-event$_i$), max_intensity_SOS_LOC(USP-event$_2$), ... max_intensity(USP-event$_L$)}. More features of the max_intensity_SOS_LOC(USP-event$_i$) are discussed below.

(iii) dominant emission locale specific for the USP event DEL(USP-event$_i$)—once a maximum intensity on the skull outer surface 151 for a particular event max_intensity_SOS_LOC(USP-event$_i$) (i is a positive integer less than or equal to L) is characterized, this will define a dominant emission locale DEL(USP-event$_i$) which is the region of space responsible (i.e. centers of one or more ultrasound transducer(s)) for at least 50% of the power of the ultrasound test signal at the maximum intensity location max_intensity_SOS_LOC (USP-event$_i$). One salient feature provided by embodiments of the invention is that this locale is small—i.e. spherical in shape with radius of at most 1 cm or at most 0.75 cm or at most 0.6 cm or at most 0.5 cm. This radius may be considered 'small' relative to the radius of curvature of the skull and/or the width of the array of transmitters used to emit ultrasound for P1110.

Ultrasound TestSignals—Each Ultrasound probe (USP) event is associated with a respective ultrasound test signal—i.e. the ultrasound signal emitted by one or more of the transducers which is propagates to the skull (e.g. and is reflected therefrom). USP-event$_i$ is associated with Ultrasound_test_signal(USP-event$_1$), USP-event$_2$ is associated with Ultrasound_test_signal(USP-event$_2$), and so on. In one example, some or all ultrasound test signals are the same—e.g. Ultrasound_test_signal(USP-event$_1$)=Ultrasound_test_signal(USP-event$_2$)=Ultrasound_test_signal(USP-event$_L$). However, this is not a requirement. In another example, each Ultrasound probe (USP) event is associated with a different ultrasound test signal.

In embodiments of the invention, the events {USP-event$_1$, USP-event$_2$ ... USP-event$_L$} are performed serially.

A Discussion of FIGS. 9A-9D, 10A-10B, 11A-11B, 12A-12B and 13-14

FIGS. 9A-9D illustrate four example USP events USP-events-USP-event$_4$. In this example, the events are performed serially—i.e. one after another.

In FIG. 9A corresponding to USP-event$_1$, an ultrasound test signal is only provided by a single ultrasound transmitter UT$_2$ while all other ultrasound transmitters UT$_1$, UT$_3$-UT$_{10}$ are 'OFF.' Thus, for USP-event$_1$ of FIG. 9A: (i) DEL(USP-event$_1$) is at the center of UT$_2$; and (ii) max_intensity_SOS_Locale(USP-events) is indicated by the 'X' in FIG. 9A.

In FIG. 9B corresponding to USP-event$_2$, an ultrasound test signal is only provided by a single ultrasound transmitter UT$_5$ while all other ultrasound transmitters, UT$_1$-UT$_4$, UT$_6$-UT$_{10}$ are 'OFF.' Thus, for USP-event$_2$ of FIG. 9B: (i) DEL(USP-event$_2$) is at the center of UT$_5$; and (ii) max_intensity_SOS_Locale(USP-event$_2$) is indicated by the 'X' in FIG. 9B.

In FIG. 9C corresponding to USP-event$_3$, an ultrasound test signal is only provided by a single ultrasound transmitter UT$_1$ while all other ultrasound transmitters, UT$_2$-UT$_{10}$ are 'OFF.' Thus, for USP-event$_3$ of FIG. 9C: (i) DEL(USP-events) is at the center of UT$_1$; and (ii) max_intensity_SOS_Locale(USP-events) is indicated by the 'X' in FIG. 9C.

In FIG. 9D corresponding to USP-event$_4$, an ultrasound test signal is only provided by a single ultrasound transmitter UT$_9$ while all other ultrasound transmitters, UT$_1$-UT$_8$, UT$_{10}$ are 'OFF.' Thus, for USP-event$_4$ of FIG. 9D: (i) DEL(USP-event$_4$) is at the center of UT$_9$; and (ii) max_intensity_SOS_Locale(USP-event$_4$) is indicated by the 'X' in FIG. 9D.

Figure 10B:
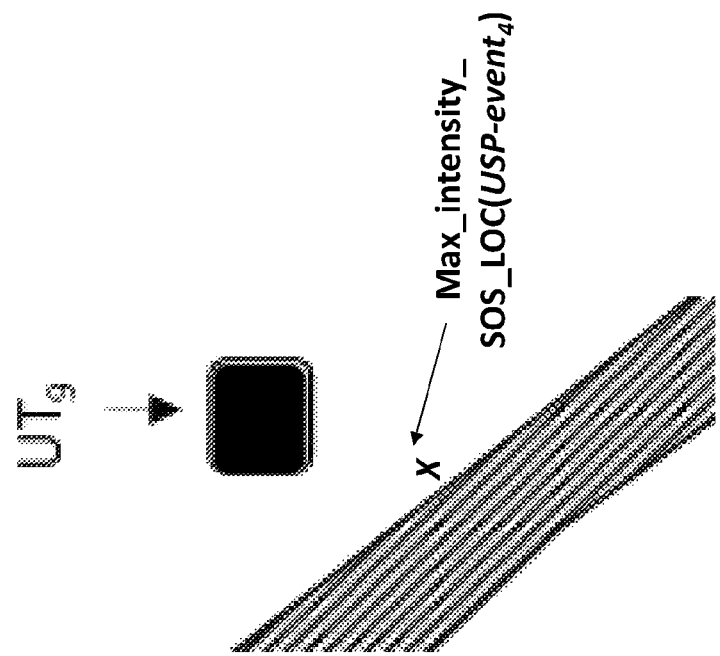
Figure 10A:
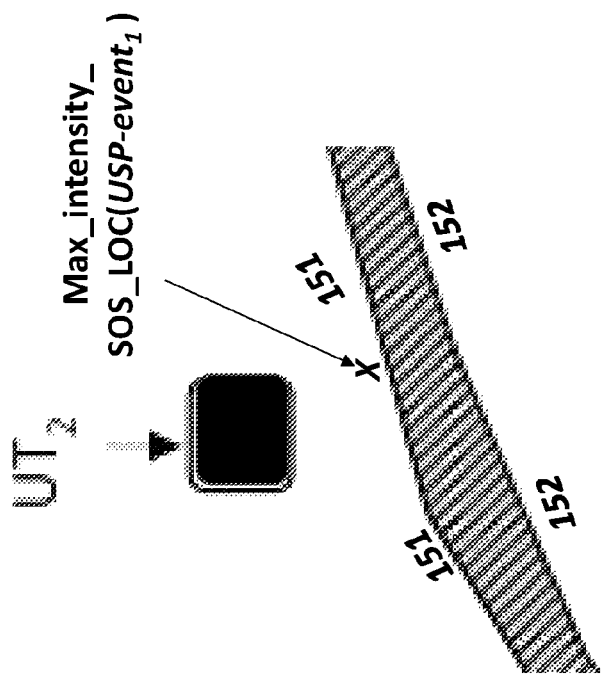

FIGS. 10A-10B are a close up respectively of USP-events of FIG. 9A and USP-event$_4$ of FIG. 9D. For this simple non-limiting example where one transducer at a time emits ultrasound energy for P1110, the location max_intensity_SOS_Locale(USP-events) (marked by the 'X' in FIGS. 9A and 10A) is simply the location on SOS 151 that is closest to UT$_2$. For this simple non-limiting example where one transducer at a time emits ultrasound energy for P1110, the location max_intensity_SOS_Locale(USP-event$_4$) (marked by the 'X' in FIGS. 9D and 10B) is simply the location on SOS 151 that is closest to UT$_9$.

Figure 11B:
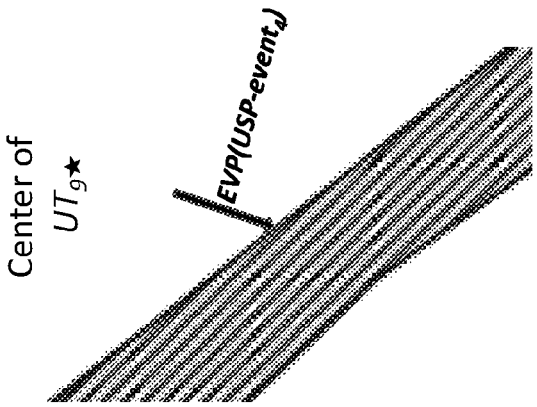
Figure 11A:
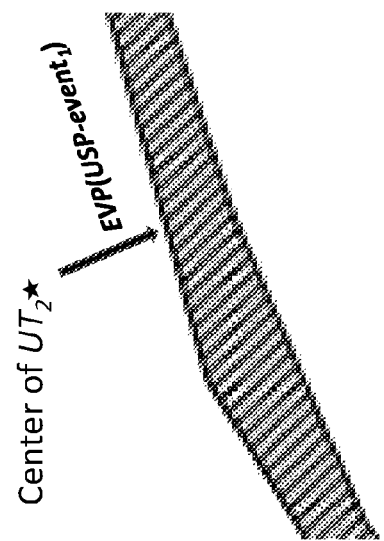

FIGS. 11A-11B shows the EFV(USP-events) and EFV(USP-event$_4$) for USP-event$_1$ and USP-event$_4$ where EFV is the directional energy flux vector or simply energy flux vector—analogous to a Poynting vector from electricity and magnetism) FIG. 4 showed one example of an ultrasound test signal—other examples are shown in FIGS. 12A-12B. FIG. 13 shows the echo signals (e.g. received after reflection from the skull) of the example test signal of FIG. 12A.

Figure 14:
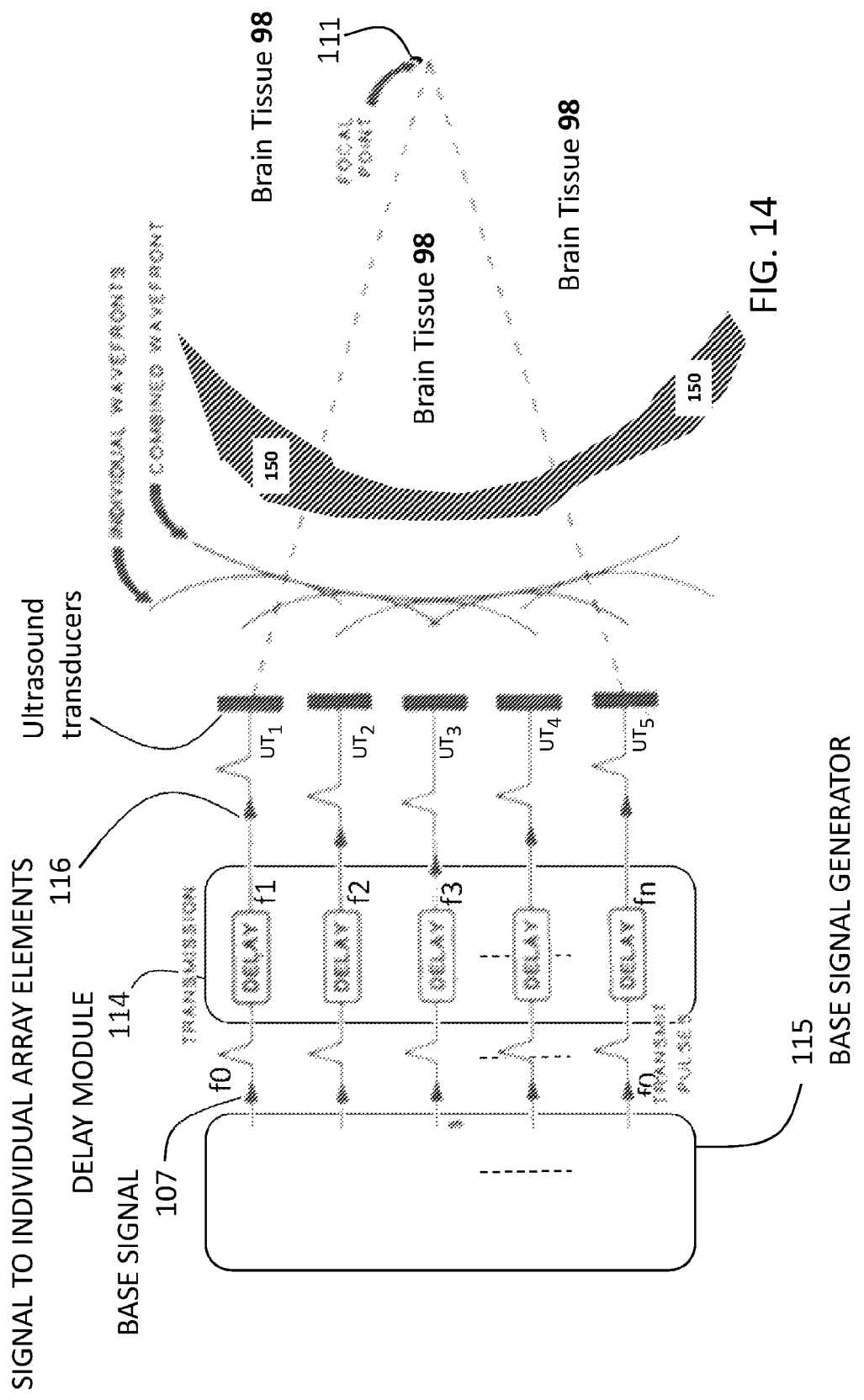

FIG. 14 shows a system for performed any method disclosed herein.

Figure 15:
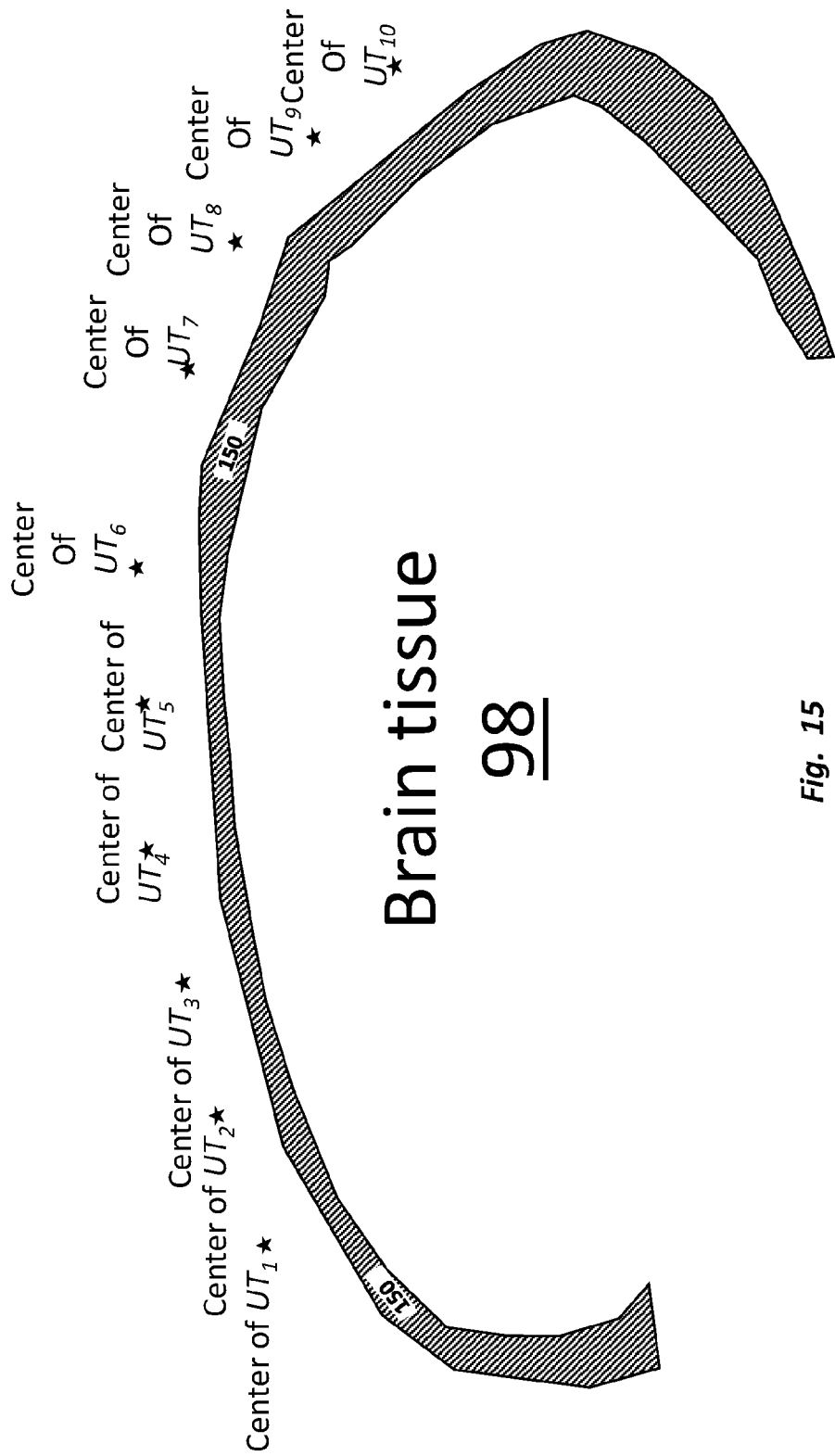
Figure 16:
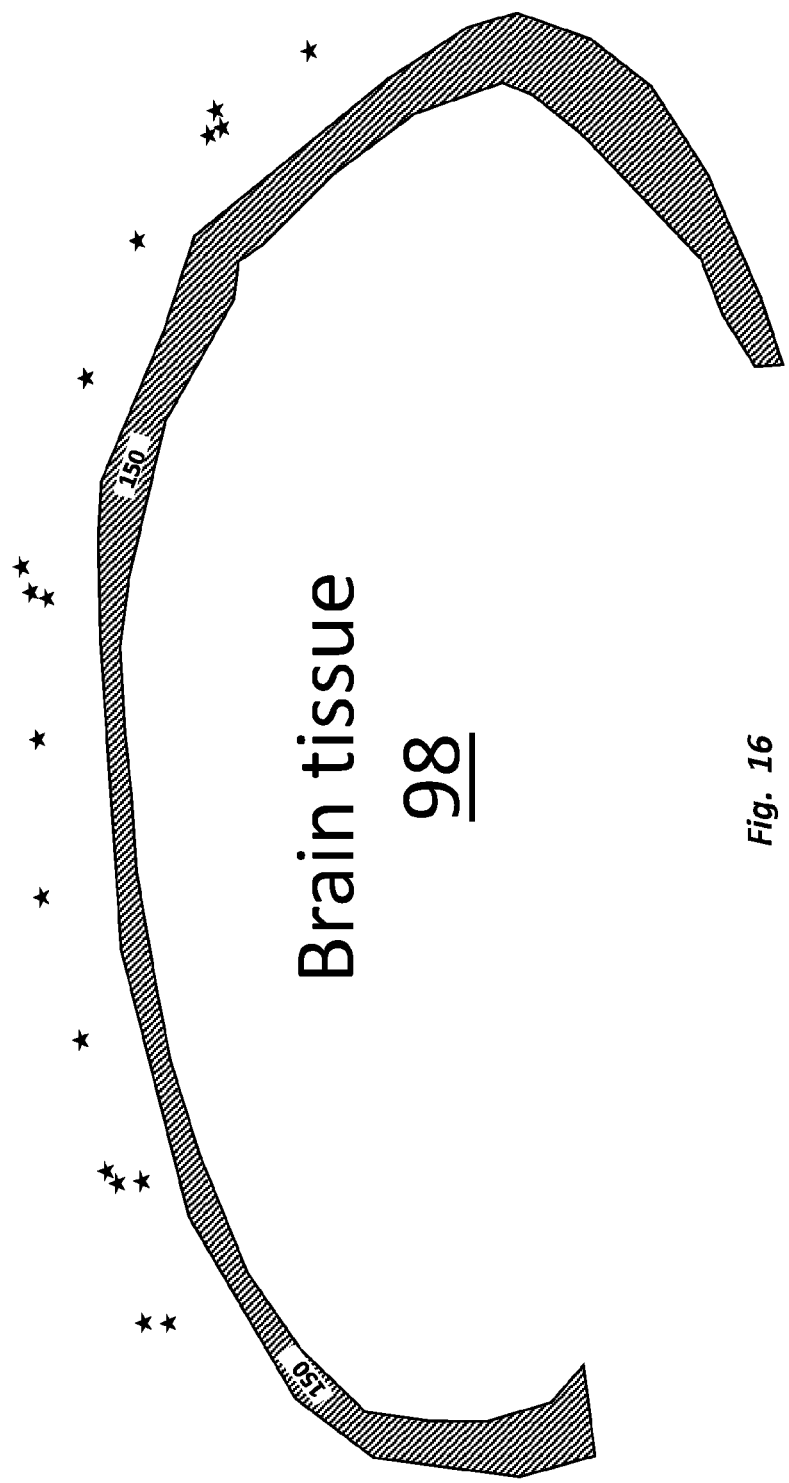
Figure 17:
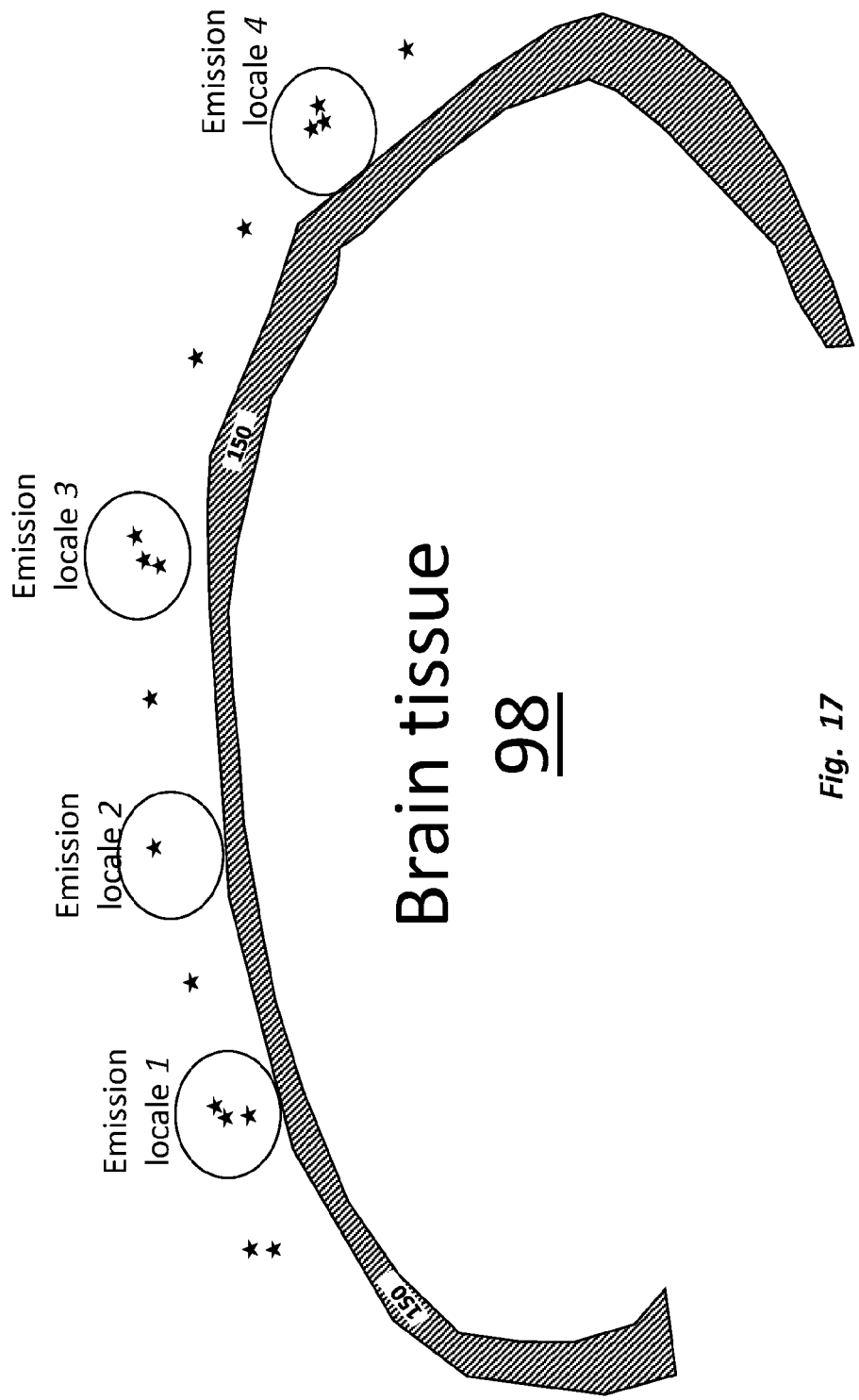

FIG. 15 shows the centers of the ultrasound transducers $UT_2$-$UT_{10}$ (also indicated as $1550_1$-$1550_{10}$) of FIG. 3—these centers are marked by 5-sided stars. In FIG. 16, it is possible to 'split' some of the ultrasound transducers into multiple transducers, centers of which are each marked by 5-sided start. The arrangement of FIG. 16 may produce effects (i.e. when emitting the ultrasound test signals in P1110) close to the arrangement of FIG. 15. In FIG. 16, $UT_1$ is split into two transducers, $UT_2$ is split into three transducers, $UT_2$ is not split, and so on. FIG. 17 shows some (but not all) transducer centers of FIG. 16 as disposed within distinct four emission locales that are each spherical in shape.

Figure 20:
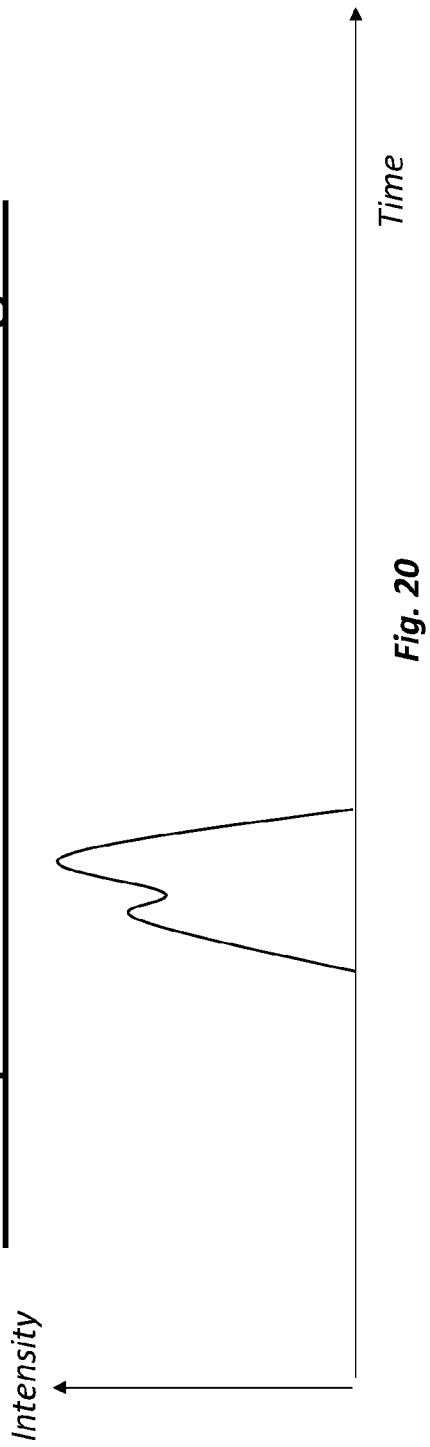

FIGS. 18-20 show additional examples of ultrasound test signals.

A discussion of FIGS. 21-45

For ease of reference the following numbers in the figures are meant to refer to as follows

- 100—focusing system.
- 110—focusing transducer.
- 111—focus peak, also is the focal center of the focusing transducer in uniform medium 99.
- 112—array 116 of calibration emitters {CE(m)}.
- 113—focusing transducer surface.
- 114—delay module, creating and outputting the time delay set {F(n)} associated with focus array elements {FE(n)}.
- 115—base-signal generator.
- 116—calibration receivers array {CR(p)}.
- 117—focus emitters array {FE(n)}
- 118—coupling medium.
- 119—focal zone area boundary, preferably defined at half maximum peak intensity.
- 121—uncalibrated focusing focus peak location in the presence an intervening skull-tissue intermediate-layer.
- 123—a first example path of ultrasound in the presence an intervening skull-tissue intermediate-layer.
- 124—a second example path of ultrasound in the presence an intervening skull-tissue intermediate-layer.
- 129—uncalibrated focusing focal zone area boundary in the presence an intervening skull-tissue intermediate-layer, preferably defined at half maximum peak intensity.
- 131—calibrated focusing focus peak location in the presence an intervening skull-tissue intermediate-layer.
- 139—calibrated focusing focal zone area boundary in the presence an intervening skull-tissue intermediate-layer, preferably defined at half maximum peak intensity.
- 140—signal generator module.
- 141*m* as calibration emitter CE(m)—representative emitter element.
- 145—emitter mux.
- 146—base signal.
- 150—intermediate-layer of intervening skull-tissue (e.g., skull bone layer).
- 151—first boundary surfaces of intermediate skull layer 150.
- 152—second boundary surfaces of intermediate skull layer 150.
- 155—incident test signal.
- 156—reflected signal from boundary surface 151.
- 157—reflected signal from boundary surface 152.
- 160—control and computation module.
- 161*p* as paired calibration receiver CR(p)—representative receiver sensor.
- 165—positioning module.
- 170—receiver control and signal analysis module.
- 172—time shift determiner module.
- 175—receiver mux.
- 212—representative 2D array
- 255—emitter/receiver switching controller.
- 310—central axis of the emitter transducer traversing the focus peak 111 in uniform medium
- 311—normal to the outer surface of the intermediate skull layer (e.g., skull bone) at the crossing point of ray 370.
- 341*m* or 141*m* as calibration emitter CE(m)—a representative emitter.
- 342*m*—a representative emitter on the other side of the central axis 310 of the transducer.
- 361*p* or 161*p* as paired calibration receiver CR(p)—receiver to which reflected ray 371 arrives.
- 361*px*—receiver sensor near to the left of emitter.
- 362*p*—receiver to which reflected ray arrives from emitter 342*m*.
- 370—ultrasound propagation "ray" from emitter 341*m* as would be in selected uniform medium 99 traversing the focus peak 111.
- 371—ultrasound propagation "ray" reflected from outer surface 151 of the intermediate skull layer (e.g., skull bone) of incident ultrasound ray 370.
- 372—ultrasound propagation "ray" reflected from inner surface 151 of the intermediate skull layer (e.g., skull bone) of incident ultrasound ray 370.
- 375—ultrasound propagation "ray" from emitter 342*m* as would be in selected uniform medium 99 traversing the focus peak 111.
- 450*a*—a first orientation of skull bone layer 150
- 450*b*—a second orientation of skull bone layer 150
- 461*p*—receiver to which reflected ray arrives when emitted from emitter 341*m* and reflected from an alternative tilt of skull bone layer.
- 561*p*—receiver to which reflected ray 571 arrives at peak intensity.
- 562*p*—receiver to which reflected ray 572 arrives at peak intensity.
- 563—intensity distribution of reflected ray 371 at the receiver array.
- 564—intensity distribution of reflected ray 372 at the receiver array.
- 571—ultrasound propagation "ray" reflected from outer surface of the intermediate skull layer (e.g., skull bone) of incident ultrasound ray 370 according to Snell law.
- 572—ultrasound propagation "ray" reflected from inner surface of the intermediate skull layer (e.g., skull bone) of incident ultrasound ray 370 according to Snell law.
- 99—matching medium between the emitter module 110 and the cranial skin surface.
- 98—intracranial brain tissue medium.

There is a need for more efficient ways of focusing a phased array of transducer element to create a high-quality ultrasound focus without recourse to an imaging model of the brain by MRI or Ultrasound. The key concept to keep in mind is that an array of emitters forms a focus peak intensity by coherent interference of the ultrasound wave-fronts from the different emitters at the peak location. The peak is deformed or destroyed by dephasing of wave-fronts at the intended peak location. Therefore, to improve or restore a sub-optimal focus peak, phase shift corrections need to be found such that coherent interference of the ultrasound wave-fronts from the different emitters at the peak location is improved. In particular, it is well known in the art of ultrasound arrays how to produce an ultrasound peak at a desired location in a uniform medium. Yet, in order to produce a focus peak within a human skull when ultrasound is produced by an array of emitters outside of the skull, there is a need to overcome the dephasing effect of the non-uniform and unknown geometry of skull bone layer.

The goal of the present invention is to provide a method and apparatus for obtaining phase shift corrections to improve the focus peak within a human skull when ultrasound is produced by an array of emitters outside of the skull.

In the following discussion, we present a general scheme of the procedures and apparatus, elaborate on several preferred embodiments, and present a numerical simulation of a realization example of an embodiment according to the invention.

Figures 26A, 26B, 26C:
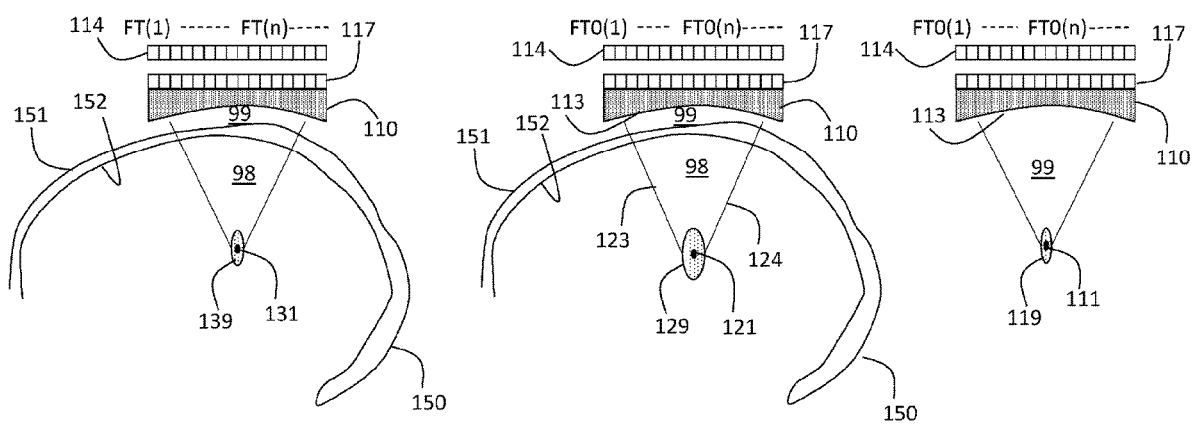
FIG. 26A illustrates the invention system when operated in a uniform medium.
FIG. 26B illustrates an embodiment of embodiment of the invention system for intra-cranial focusing with skull aberration calibration.
FIG. 26C illustrates the invention system when operated for intra-cranial focusing after aberration calibration.

As illustrated in FIG. 26A, for a given placement of an ultrasound array 117 of focus emitters {FE(n)}, assuming a specific uniform medium characterized by a specific speed of sound, there is a well-defined path traversal time of the sound from each focus-emitter FE(n) to the target focus center 111. For example, consider focusing within a uniform medium with speed of sound of 1540 meters per second (m/s), similar to body tissue. It is well known to predict the ultrasound travel time from the known geometric distance from each emitter to the target focus center 111. Thereby it is known to determine the required set of uniform medium relative time delays {FT0(n)}={FT0(1), FT0(2) ... FT0(N)} that needs to be provided by the associated signal drivers array 114 to obtain constructive ultrasound interference at the target focus center 111. Hence, which each individual emitter FE(n) of the focus emitters array {FE(n)} produces ultrasound radiation which is unfocussed (in the sense that it is not focused peak maximum on the target focus area), the array as a whole creates a focused peak maximum at the target focus area. In such uniform medium setting, the ultrasound focus is obtained with focal zone 119 having characteristics zone cross-section geometry and cross section area. Indeed, we posit that the non-uniformity of brain tissue speed of sound is small enough that its effect on the focal zone is negligible for most practical purposes.

Yet, as illustrated in FIG. 26B, when ultrasound is focused into the brain, if using a uniform medium set {FT0(n)}, with the skull intervening bone-tissue intermediate-layer 150 in the acoustic path, there may be aberrations that enlarge the focal zone 129 in comparison with the focal zone 119 width created in fully uniform medium setting, and/or shift the focus peak and/or create satellite peaks. The present disclosure provides a method and apparatus for improving (i.e., reducing the size of) the focal zone in such a situation.

The beam of acoustic energy emitted from the focus-emitters array 117 has a relatively wide aperture where it enters the body. Therefore, different parts of the acoustic energy, such as 123 and 124, may pass through different intervening tissue layer thickness between, which may shift the effective relative time delay of acoustic energy transmitted from respective transducer elements upon arrival to the focal zone. This phase shifting may decrease the constructive interference of the acoustic energy at the focal zone, or may even move the focal zone in an unpredictable manner. For example, an intervening skull bone layer thickness difference of 1.5 mm may introduce a phase shift of 180° at an ultrasonic frequency of one Megahertz (1 MHz), which would change desired constructive interference at the focal zone into destructive interference.

In some embodiments, ultrasound frequency lower than 1 MHz, such as between 100 KHz and 500 KHz, is used in order to reduce the aberration effect of non-bone tissue inhomogeneity in the brain.

As illustrated in FIG. 26C, when the emitter array is activated for focusing, the goal is to create a focus peak using an array 117 of focus-emitters {FE(n)}={FE(1), FE(2) ... FE(N)}. This is achieved with the emitter array activated with a set of relative time delays (alternatively delineated "phase shifts") of the signals delivered to the corresponding transducer array of focus-emitter elements {FE(n)}.

Thus, a principal goal, according to embodiments, is to determine a calibration delay set {CT(n)} alternatively "correction phase shifts" from which a calibrated focusing delay set {FPS(n)} can be computed such as {FPS(n)}={FT0(n)+CT(n)}. Thereby, the ultrasound wave paths pass through an intervening skull-tissue intermediate-layer bounded by first (outer) and second (inner) boundary surfaces within otherwise same uniform medium 99 in the path from the transducer surface to the resulting focus peak location 131 with resulting focal zone area 139, such that the focal zone area 139 is smaller than the focal zone 129 created when the focusing transducer array 110 is driven with an uncalibrated signal delay set {FT0(n)}. Hence the focus is improved. The resulting focus peak location 131 is very close to the planned target focus peak location 111 in the sense that the planned target focus peak location is within the resulting focal zone area 139.

The key problem is how to determine the calibration set {CT(n)}. The present disclosure provides methods and systems for determining the calibration set {CT(n)} and thereby creating an improved focus when the focused ultrasound waves path pass through an intervening skull-tissue intermediate-layer 150 bounded by first boundary surface 151 and second boundary surface 152 within otherwise approximately uniform out-of-skull medium 99, and/or similar approximately uniform medium of under-skull brain tissue 98, in the path from the transducer surface to the focus peak.

We conceptualize the method procedure as composed of two major stages: (i) scanning measurements and analysis procedure "PROC-1", and (ii) calibrated focusing irradiation application procedure "PROC-2".

The scanning procedure PROC-1 can be sub-divided into two prominent sub-tasks: (a) physical measurement procedure "MEASURE", and (b) computational analysis "ANALYSIS" from which the key outcome is the determination of the calibration set {CT(n)}.

In the known art, the measurement procedure is an imaging scan followed by an analysis procedure which involves constructing a geometrical 3D image of the skull and assigning phase shift properties to the constructed 3D geometry. In contrast, in the present disclosure the measurement procedure comprises non-imaging non-focusing MEASURE measurements and the calibrated phase shift set elements are computed directly from the MEASURE measurements without going through the construction of a geometrical image of the skull.

The calibrated focusing irradiation application procedure "PROC-2" can be sub-divided into two prominent sub-tasks: (a) Input parameters set-up, and (b) irradiation application process.

The calibrated focusing irradiation application procedure "PROC-2" is similar to known art. Given the calibration set {CT(n)} from PROC-1, the system is activating the focusing emitters array {FE(n)} with the corrected set {FPS(n)} of input parameter phases. Various other irradiation application process characteristics (intensity, duration, etc. ... ) are determined by clinical goals (e.g., nerve stimulation, tissue ablation, etc. ... ).

The innovation is primarily contained in the preparatory measurement MEASURE process in PROC-1 method and apparatus and from it the computation method ANALYSIS from which the core outcome is the values of the calibration set {CT(n)} of input parameters that is used to define the corrected set {FPS(n)} of phases.

In order to facilitate the presentation, we define several semantic functional sets. "semantic" meaning is distinguished from "physical", in the sense that, for example, physically the same component can be operated as a transceiver which is capable of both emitter functionality and receiver functionality.

These sets comprising:

{FE(n)} array 117 of focus-emitters (FEA), {FE(n)}={FE (1), FE(2) . . . FE(N)};

{CE(m)} array 112 of calibration-emitters array (CEA), {CE(m)}={CE(1), CE(2) . . . CE(M)};

{CR(p)} array 116 of ultrasound calibration-receivers array (CRA), {CR(p)}={CR(1), CR(2) . . . CR(P)};

{USP(i)} set of unfocused ultrasound skull-probe (USP) events {$USP_1$, $USP_2$ . . . $USP_L$} (1≤i≤L);

{[CE(j),CR(k1),CR(k2)]} set of calibration-emitter:calibration-receiver triplets (CECRP); for measuring echo differences; METD(j,k1,k2) between an outer-skull-surface reflection-time received at receiver CR(k1) and an inner-skull-surface reflection-time received at receiver CR(k2) of an ultrasound test signal that is emitted from the calibration emitter CE(j).

{METD(j,k1,k2)} set of measured echo time differences; METD(j,k1,k2) between an outer-skull-surface reflection-time received at receiver CR(k1) and an inner-skull-surface reflection-time received at receiver CR(k2) of an ultrasound test signal that is emitted from the calibration emitter CE(j) of the triplet [CE(j),CR(k1),CR(k2)];

{FT0(n)} set of uncalibrated signal delay—for focusing ultrasound with the array of focus-emitters {FE(n)} in a uniform medium;

{FPS(n)} set of correction phase-shifts (FPS), {FPS(n)}={FPS(1) . . . . FPS(N)}; computed as a function of the time delay set {TD(m)} and uncalibrated signal delay set {FT0(n)};

{TD(j)} time delay set, computed from measured echo time differences set {METD(j,k1,k2)};

The method and apparatus, according to embodiments, comprise using arrays (alternately and interchangeably referred to as "sets") of ultrasound elements comprising:

a. an array 117 of ultrasound focus-emitters {FE(n)}={FE(1), FE(2) . . . FE(N)} activated simultaneously to generate through the skull an ultrasound intensity-peak within a patient's brain under the skull;

b. an array 112 of ultrasound calibration-emitters {CE(m)}={CE(1), CE(2) . . . CE(M)} configures such that each element can generate a test signal directed towards the skull; the calibration-emitters {CE(m)} are activated primarily non-simultaneously and non-focused onto the skull during a MEASURE procedure;

c. an array 116 of ultrasound calibration-receivers {CR(p)}={CR(1), CR(2) . . . CR(P)} configured to detect ultrasound signals reflected from the skull.

As illustrated in FIG. 21A, in some embodiments, the array 112 of ultrasound calibration-emitters {CE(m)} and the array 116 of ultrasound calibration-receivers {CR(p)} may physically consist of the same transducer elements, since ultrasound transducers are known in the art to be possible to switch between emitter and receiver functionality.

Figure 1A:
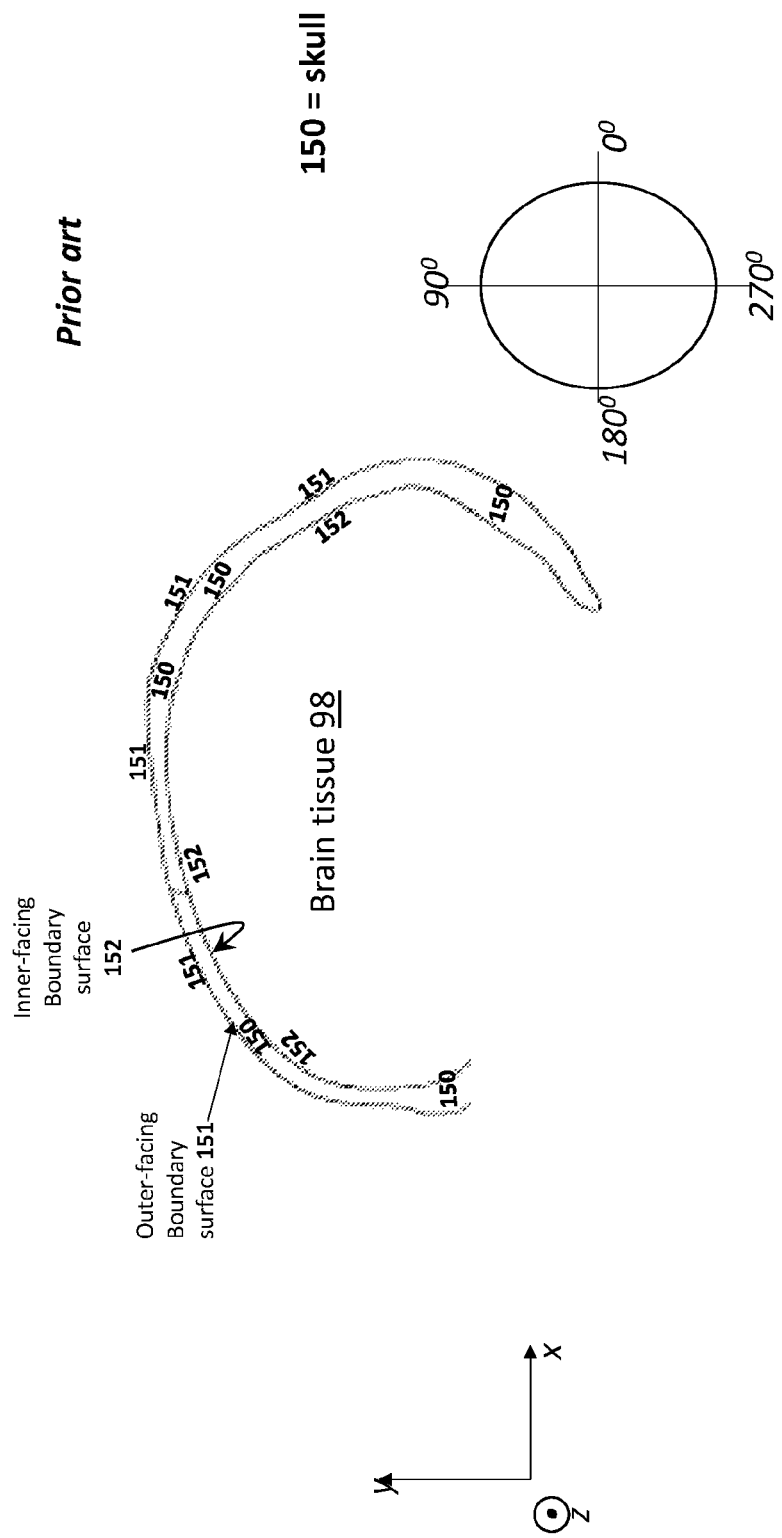
FIGS. 1-2 relate to prior art.

The measurement MEASURE procedure, according to some embodiments, as for example illustrated in FIG. 21A and FIG. 21B, comprises:

a. positioning the calibration-emitters array (CEA) 112 in proximity of the skull, such that the distance D1 of the CEA to the skull is smaller than 50% of the width W1 of the CEA, and positioning the array 116 of and calibration-receivers array {CR(p)} relative to calibration-emitters array (CEA) 112;

b. performing a calibration measurement procedure P110 of subjecting the skull to at least 10 local ultrasound skull-probe (USP) events P120 {$USP\text{-}event_1$, $USP\text{-}event_2$ . . . $USP\text{-}event_L$}(L≥10) such that:

i. each USP event is dominated by a different calibration emitter CE(j) to probes a different associated outer surface skull local area LOC[CE(j)] with an ultrasound test signal;

ii. during each $USP\text{-}event_j$ P120, the test signal emitted from calibration emitter CE(j) has peak intensity within the associated skull local area;

iii. the test signal emitted from any other calibration emitters CE(j'≠j) which dominate any other of the USP events, is having less than 50% of the intensity of the test signal originating from the dominant calibration emitter CE(j) at the skull local area LOC[CE(j)];

For example, in some preferred embodiments, during each $USP\text{-}event_j$ an individual calibration emitter CE(j) is activated to emit a test signal while all other calibration emitters CE(j'≠j) are kept dormant, thereby each USP event is dominated by a different calibration emitter CE(j). Since the calibration-emitters array (CEA) 112 is positioned in proximity of the skull, as illustrated in FIG. 1A, a test signal emitted from calibration emitter CE(j) has peak intensity within the associated limited skull local area close to the emitter CE(j), even when the signal emitted from an individual calibration emitter CE(j) is in itself unfocused in general and unfocused on the skull in particular. Hence, in some preferred embodiments we refer to the test signal as "unfocused ultrasound".

Yet in some other embodiments it is possible to activate some calibration emitters CE(j) in parallel while still maintaining the conditions of the invention method and apparatus. As illustrated in FIG. 1A, for emitters which are CE(j') which are sufficiently distanced from emitter CE(j), a signal from CE(j') will not have a significant intensity in the location of skull local area LOC[CE(j)] associated with calibration emitters CE(j) during the $USP\text{-}event_j$ in which the test signal is emitted from CE(j).

Figure 24A:
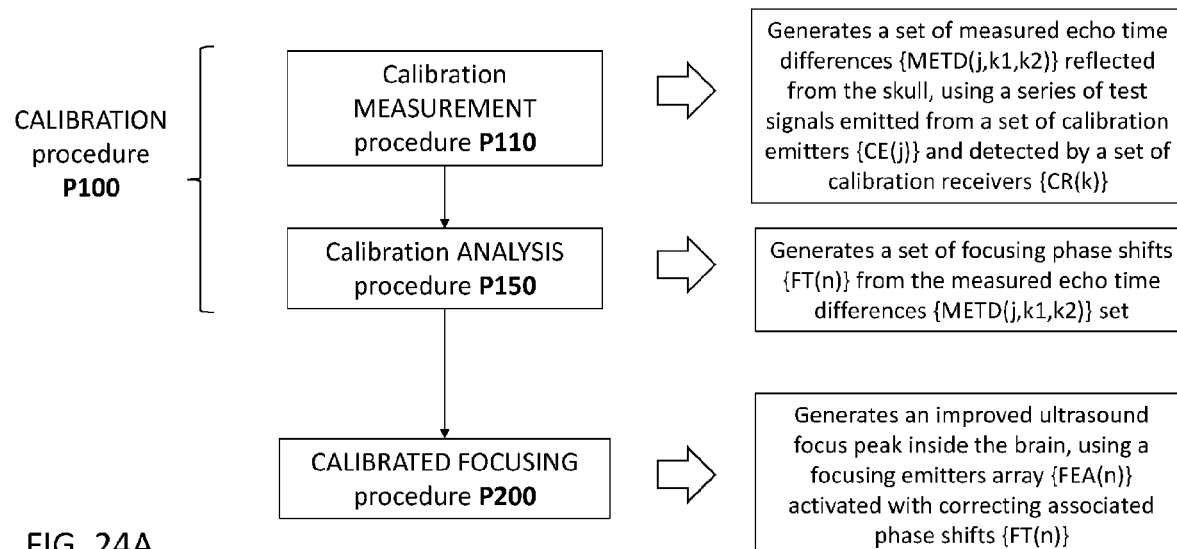
FIGS. 24A to 24F illustrates flow charts of an embodiment of the invention.
Figure 24B:
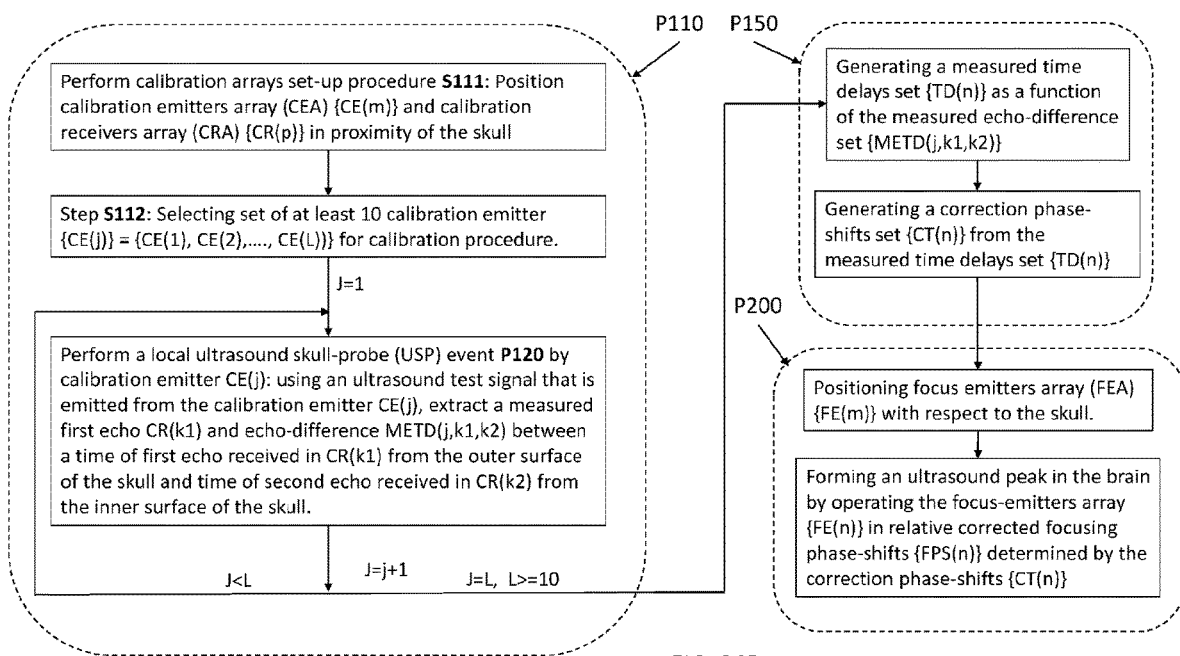
Figures 24C, 24D:
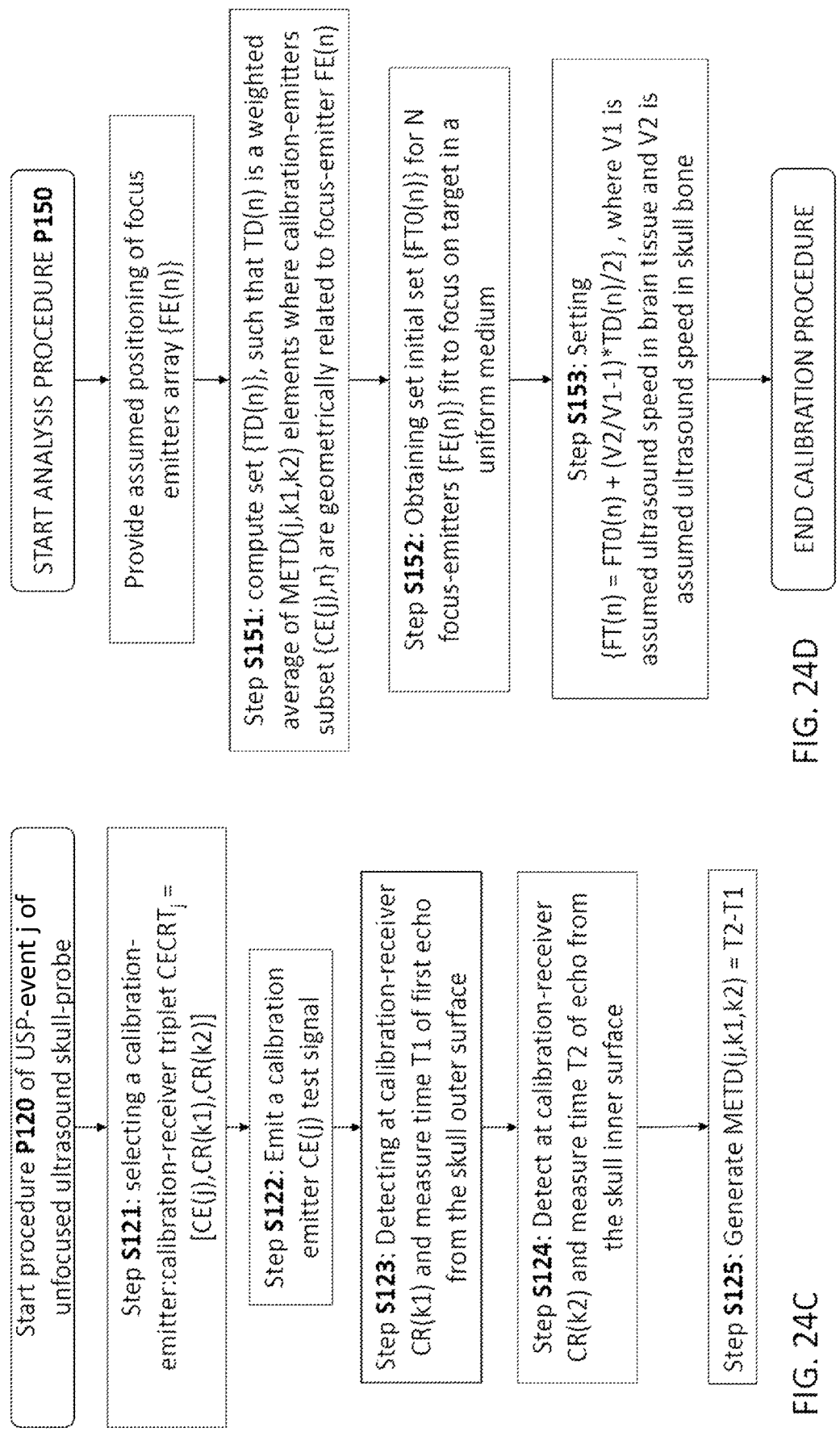
Figure 24E:
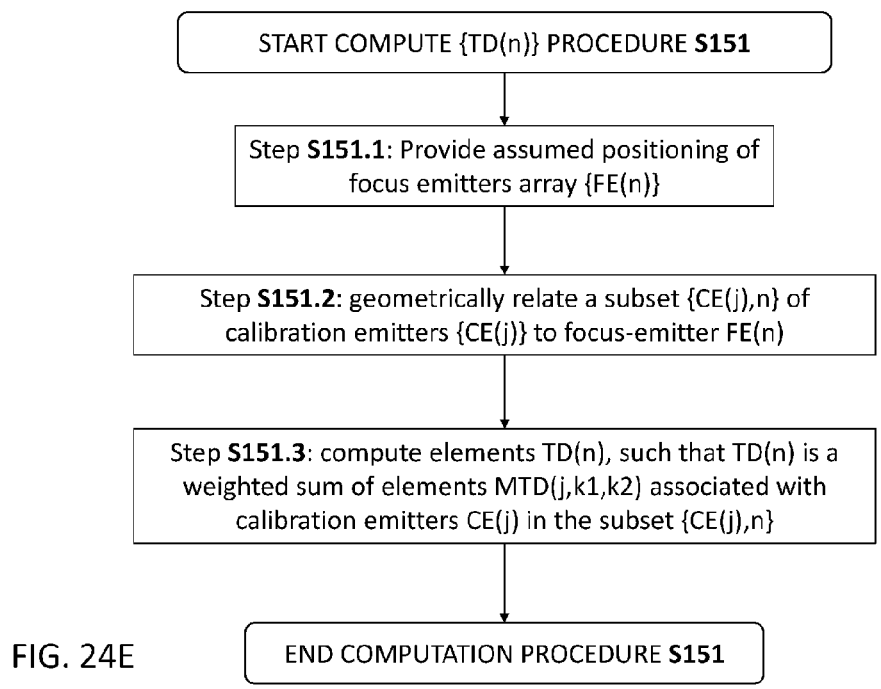
Figure 24F:
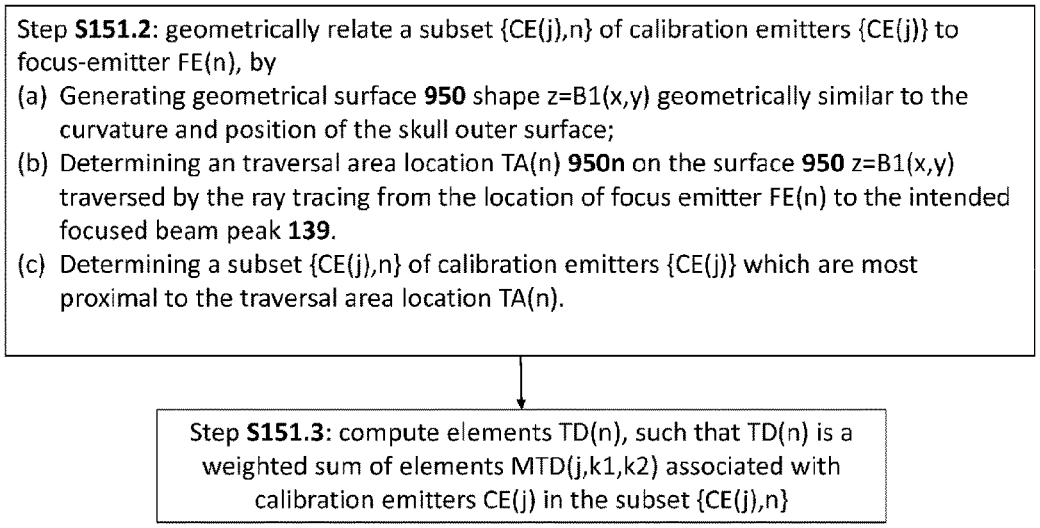

Continuing with the elaboration of the steps of performing a calibration measurement procedure:

iv. for each $USP\text{-}event_j$, selecting S121 a triplet $CECRT_j$=[CE(j),CR(k1),CR(k2)], associating the calibration receivers CR(k1),CR(k2), selected from CRA {CR(p)}, with the calibration emitter CE(j);

v. measuring, for each $CECRT_j$ [CE(j),CR(k1),CR(k2)], a measured echo time difference S125 METD(j,k1,k2)=T2-T1, between (A) a measured time T1 at which receiver CR(k1) detects S123 a first echo and (B) a measured time T2 at which receiver CR(k2) detects S124 a second echo; where each of the first and second echoes being echoes of an ultrasound test signal that is emitted S122 from the calibration emitter CE(j);

The analysis ANALYSIS procedure comprises:

c. a calibration analysis procedure P150 wherein a plurality of corrected focusing phase-shifts {FPS(n)}={FPS(1) . . . . FPS(N)} are computed for the associated focus-emitters array {FE(n)}, one focusing phase-shift FPS(n) per focusing-emitter FE(n), electronically computing S153 {FPS(n)} as a function of the measured echo time difference set { METD(j,k1, k2)};

In particular, in some embodiment, as indicated by the flow chart of FIG. 24B, the calibration analysis comprises
  i. Generating a measured time delays set {TD(n)} as a function of the measured echo-difference set {METD (j,k1,k2)}; and
  ii. Generating a correction phase-shifts set {CT(n)} from the measured time delays set {TD(n)}

It is known in the art how to focus a focusing array in a uniform medium with a signal delay set {FT0(n)} for focusing ultrasound with the array of focus-emitters {FE(n)} in the uniform medium. Thus, in the non-uniform medium comprising the skull, the correction phase-shifts set {CT(n)} are used to adjust the relative phase shifts focusing ultrasound with the array of focus-emitters {FE(n)} to the plurality of corrected phase-shifts {FPS(n)}={FPS(1), ..., FPS(N)} as a function of the correction phase-shifts set {CT(n)} and uncalibrated signal delay set {FT0(n)}. Hence, in some embodiments, the analysis procedure is further comprising of
  iii. having a pre-determined uncalibrated signal delay set {FT0(n)} for focusing ultrasound with the array of focus-emitters {FE(n)} in a uniform medium;
  iv. electronically computing the plurality of correction phase-shifts {FPS(n)}={FPS(1), ..., FPS(N)} as a function of the time delay set {TD(m)} and uncalibrated signal delay set {FT0(n)};

Preferred embodiments of specific computation formulas are elaborated in the text below.

The echo time difference METD(j,k1,k2) is measured between an outer-skull-surface reflection-time and an inner-skull-surface reflection-time of ultrasound test signal that is emitted from the calibration emitter CE(j) of the pair [CE(j), CR(k)], thereby creating a time delay set {TD(n)}, the set {TD(n)} is computed such that TD(n) is a weighted sum or average of METD(j,k1,k2) elements where CE(j) are geometrically related to calibration-emitters to focus-emitter FE(n).

The emitter CE(j) is conceptualized as an ultrasound source of limited extent in space of less 22 Cm area, whether made of one or more transducers. In most cost effective embodiments, the emitter CE(j) is consisting of a single transducer. Thereby, for each given calibration-emitter:calibration-receiver triplet [CE(j),CR(k1),CR(k2)] of {[CE(j), CR(k1),CR(k2)]} triplets, measuring is performed without generating a geometrical imaging of the skull.

The number of calibration emitters in the set {CE(m)} and the number of focus emitters in the set {FE(n)} may be different, and hence also the number of measured echo time difference METD(j,k1,k2) elements in the set {METD(j,k1,k2)} may be different than the number of focus emitters in the set {FE(n)}. Therefore, in computing the may incorporate weighted averages of several measured echo time difference METD(j,k1,k2) elements within a given neighborhood of a local on the skull.

The measurement MEASURE procedure, according to some embodiments, comprises:
  a. positioning the array 116 of calibration emitters {CE (m)} and calibration-receivers array {CR(p)} relative to a target focus location 111;
  b. defining, dependently or independently of the target peak location 111, a plurality of distinct calibration-emitter:calibration-receiver triplets {[CE(j),CR(k1),CR (k2)]};
  c. for each given calibration-emitter:calibration-receiver triplet [CE(j),CR(k1),CR(k2)] of {[CE(j),CR(k1),CR (k2)]} triplets, measuring without ultrasound imaging and without focusing ultrasound a measured echo time difference METD(j,k1,k2) between an outer-skull-surface reflection-time and an inner-skull-surface reflection-time of ultrasound test signal that is emitted from the calibration emitter CE(j) of the pair [CE(j), CR(k)], thereby creating a time delay set {TD(n)}, the set {TD(n)} is computed such that TD(n) is a weighted sum of METD(j,k1,k2) elements where CE(j) are geometrically related to calibration-emitters to focus-emitter FE(n)

The analysis ANALYSIS procedure comprises:
  v. having a pre-determined uncalibrated signal delay set {FT0(n)} for focusing ultrasound with the array of focus-emitters {FE(n)} in a uniform medium;
  vi. electronically computing the plurality of correction phase-shifts {FPS(n)}={FPS(1), ..., FPS(N)} as a function of the time delay set { TD(m)} and uncalibrated signal delay set {FT0(n)};

The total set of emitters {E(q)}={E(1), E(2) ... E(Q)} comprises of the union of {FE(n)} and {CE(m)}. The arrays {FE(n)} and {CE(m)} may overlap spatially. The sets {FE (n)} and {CE(m)} may intersect (i.e., share elements). In fact, from cost, performance and simplicity considerations, an embodiment is one in which the arrays {FE(n)} and {CE(m)} are physically the same elements. i.e., the array 112 and array 117 are one and the same), or one is a subset of the other (e.g., {CE(m)} is a subset of {FE(m)}, such that only a portion of the emitters are used for the calibration process. Therefore, some of the figures and embodiment examples are drawn as such. i.e, there is one array (112,117) of physical ultrasound emitters that serves both for the purpose of MEASURE procedure (in PROC-1) and for focusing (in PROC-2). Yet this should not be understood as limiting.

For a given MEASURE procedure, defining a plurality of distinct calibration-emitter:calibration-receiver triplets {[CE (j),CR(k1),CR(k2)]}. for measuring echo differences; METD(j,k1,k2) between an outer-skull-surface reflection-time received at receiver CR(k1) and an inner-skull-surface reflection-time received at receiver CR(k2) of an ultrasound test signal that is emitted from the calibration emitter CE(j).

The triplet [CE(j),CR(k1),CR(k2)] may be regarded as composed of two calibration-emitter:calibration-receiver pairs: the pair [CE(j),CR(k1)] for measuring the outer-skull-surface reflection-time received at receiver CR(k1) of an ultrasound test signal that is emitted from the calibration emitter CE(j); and the pair [CE(j),CR(k2)] for measuring the inner-skull-surface reflection-time received at receiver CR(k2) of an ultrasound test signal that is emitted from the same calibration emitter CE(j).

As known in known art, there are multiple methods of determining the calibration set {CT(n)} if there is a given geometry of the intermediate skull layer (e.g., skull bone layer). The problem is how to determine the skull properties and geometry non-invasively. For concreteness we define the intermediate skull layer geometry by knowledge of first boundary surface 151 shape function Z1(x,y) and the second layer 152 shape function Z2(x,y).

In known art, for skull bone, the skull bone layer geometry is determined from MRI or CT imaging. Thus, in known art the MEASURE sub-task measurement procedure PROC-1 is an imaging procedure done by MRI or CT scanning, from which various skull parameters are determined by supplemental external information. e.g., from multiple slices of MRI images a full 3D skull bone section shape is reconstructed. In addition, external information concerning speed of sound in the bone is supplemented to predict and determine the supposed time shifts created by the skull bone on ultrasound. i.e., the MRI or CT scanning is NOT by itself directly measuring ultrasound phase shift or time shift due to passage through the skull layer.

In known art ANALYSIS sub-task, each phase shift correction CT(n) to be applied to individual emitter En is determined by going through a geometrical reconstruction of the intermediate skull layer shape and considering the particular path of the ultrasound from the emitter En to the intended focus location.

In contrast, the present invention: (i) uses ultrasound emitters array not only for the irradiation PROC-2 procedure, but also for the measurement PROC-1 procedure, thereby eliminating completely the need for non-ultrasound MRI or CT at any step of the full procedure (PROC-1 and PROC-2) method and apparatus; (ii) what is measured is not geometrical imaging of the skull shape, but the direct ultrasonic shift effects of the skull. It is conjectured that the measurement is somehow capturing a measure that is proportional to the real focusing path without actually being the focusing path or focused at all; and (iii) the ultrasound MEASURE procedure method in the present invention is different from what is commonly understood as "ultrasound scanning" in known art of medical ultrasound imaging. In particular, known art medical ultrasound scanning is an imaging procedure using focused ultrasound, thereby, skull scanning and/or imaging is done by focusing ultrasound array onto the skull. In contrast, in the present invention, only individual calibration-emitter elements CE(m) are activated, without focusing on the skull or any brain tissue, during the MEASURE process of PROC-1. Preferably individual, or at most a small fraction of the calibration-emitters array elements {CE(m)}, e.g., less than 20%, are activated simultaneously. The focusing emitters array elements {FE(q)} are activated simultaneously only during the irradiation-focusing PROC-2 procedure, and not on skull tissue. Moreover, in some embodiments, the calibration-emitters are not producing a focused beam in general and specifically not focused on the skull surface.

In known art, scanning with ultrasound phase arrays, what is conventionally understood to be ultrasound scanning: (i) all of the array elements are operated to radiate simultaneously, (ii) a focused beam is used, and (iii) target area scanning is performed by steering the beam focus by way of modifying the relative phase shifts between simultaneously activated array elements. In order to find and trace the skull outer surface, known art phased array scan is moving the focus over a volume within which the skull is assumed to be residing somewhere. In contrast, none of the above is conducted in the present invention ultrasound MEASURE procedure.

The present invention MEASURE sub-task, in some embodiments, is characterized by that: (i) the array ultrasound elements are operated serially in time, such that individual array element (or small groups of elements the majority of which consisting of less than 10% of the number array elements) are operated on after the other, and preferably after the previous element signal reflection have been measured; (ii) the ultrasound beam is not focused; (iii) target area Measurement is performed by NOT by steering a beam focus, but instead by way of each individual array element (or small group of elements) measuring the small section of the intermediate skull layer (e.g., skull bone) closest to it.

In addition, in embodiments of the present invention ANALYSIS sub-task, each phase shift correction CT(n) to be applied to individual emitter En is determined directly from the associated individual emitter En MEASURE step, without going through a geometrical reconstruction of the intermediate skull layer shape and without considering the particular path of the ultrasound from the emitter to the intended focus.

In embodiments, $$CT(n)=(V2/V1-1)*TD(n)/2$$

i.e., $$FPS(n)=FT0(n)+(V2/V1-1)*TD(n)/2,$$

where V1 is an assumed pre-determined average speed of sound in the interior brain tissue (preferably within 10% accuracy), and V2 is an assumed pre-determined average speed of sound in the intermediate skull layer (e.g., skull bone), preferably within 20% accuracy (and more preferably within 10% accuracy). The time TD(n) is determined from the time difference between the reflected signals 171 from the intermediate skull layer first surface 151 and the reflected signals 172 from the intermediate skull layer second surface 152.

In other embodiments, ANALYSIS sub-task is more conventionally performed, such that each phase shift correction CT(n) to be applied to individual emitter En is computed by going through a geometrical reconstruction of the intermediate skull layer shape and considering the particular path of the ultrasound from the emitter En to the intended focus location. Yet, in the present invention the geometrical reconstruction of the intermediate skull layer shape and thickness are determined in a novel way.

Figure 27:
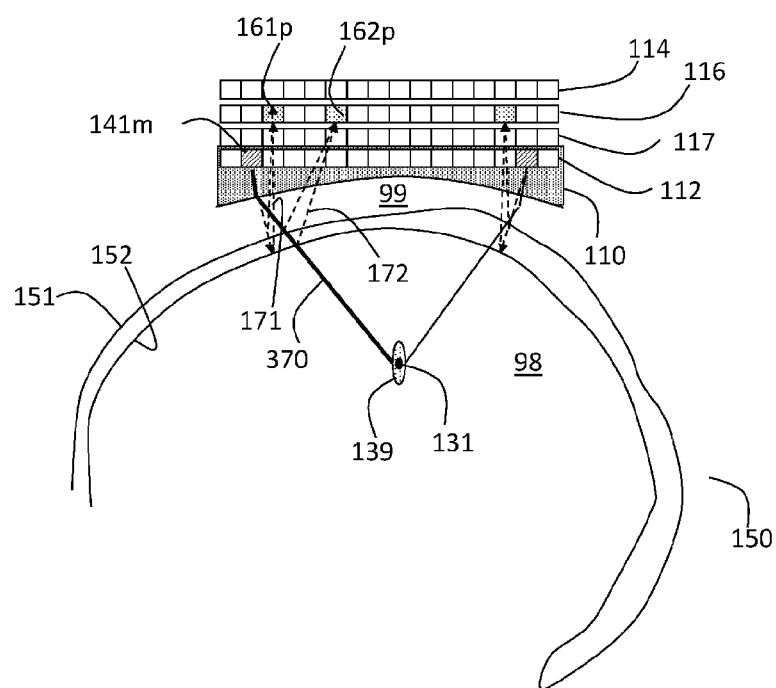
FIG. 27 illustrates an embodiment of embodiment of the invention system for intra-cranial focusing with skull aberration calibration.
Figure 28:
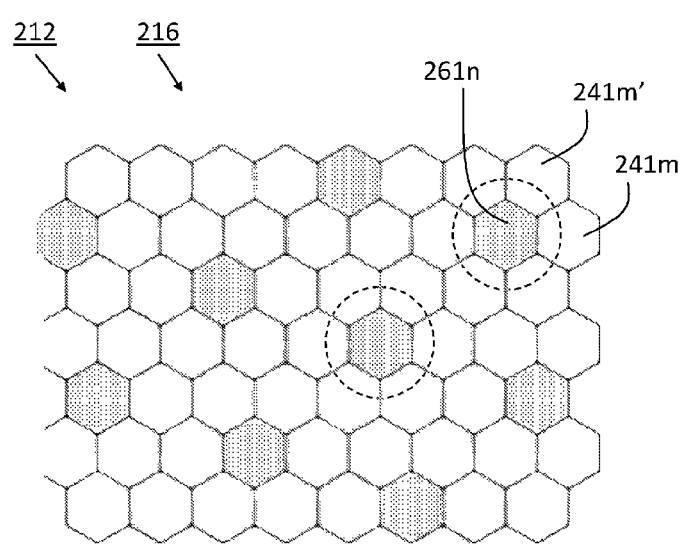
FIG. 28 illustrates an embodiment of embodiment of the invention system two-dimensional array of emitter elements and receiver elements.

For example, as illustrated in FIG. 27, in a MEASURE step, individual emitter 141m as calibration emitter CE(m) is emitting a signal while all other emitters (or at least nearby emitters) are not activated. The reflected echo signal 171 from the intermediate skull layer first surface 151 and the reflected echo signal 172 from the intermediate skull layer second surface 152 are each detected at the same receiver sensor 161p as paired calibration receiver CR(p) (in practice the physical receiver sensor 161p as paired calibration receiver CR(p) can be the same as the emitter source 141m as calibration emitter CE(m)), and the time difference TD(n) between them is determined (e.g., the time difference between the maximum peaks of the received echo signals). Similarly, such MEASURE steps are serially performed in time on other emitters (preferably most of the emitters, or all of the emitters), thus generating the echo time difference set {TD(n)}.

We interpret and associate each measured TD(n) as an estimation of the local time difference of ultrasound to so twice across the local skull bone thickness nearest to the emitter element En.

In embodiments, the calibration elements CT(n) forming the calibration set {CT(n)} are each a function of TD(n), V1 and V2. Preferably, as noted before, $$CT(n)=(V2/V1-1)*TD(n)/2.$$

In addition to the phase corrections, amplitude corrections can be determined from the reflected test signals from individual emitters.

In addition, to maximize the transmitted intensity, a step of frequency-test scan is added to be performed prior to treatment application PROC-2, or prior to the MEASURE procedure. In the frequency-test scan, the goal is to find the frequency of maximum transmission through the intermediate skull layer in order to minimize loss of intensity at the focus (due to reflection from the intermediate bone layer) and in order to minimize heat deposition within the intermediate bone layer. In a frequency-scan, for a local region the reflected signal intensity is measured while changing the emitter activation frequency range around a central work frequency, e.g., within 10% deviation from the central work frequency. For example, if the work frequency is chosen to be 500 KHz, a scan of frequency range between 450 KHz and 550 KHz is performed. Minimum local of reflected signal intensity indicates maximum local transmission at the associated frequency.

In embodiments, the frequency scan is performed for the array activation as a whole (rather than for local regions).

It should be noted that, in contrast to conventional focused-beam scanning used in ultrasound imaging, the amplitude of reflected beams received by receiver array is not used in the procedures disclosed herein except for (a) using the timing of peak amplitudes in reflected signals in order to acquire the time delays to be used for phase corrections (or phase shifts) for each emitter, and (b) as described in the preceding paragraphs, for optimizing the measurement frequency in order to maximize the transmitted intensity of the focused ultrasound radiation during the subsequent PROC-2 procedure. In conventional focused-beam scanning used in ultrasound imaging, on the other hand the amplitude of reflected beams is an important element of producing images or digital representations of the scanned tissues.

Thus, as illustrated in FIG. 27, we introduce method for generating an ultrasound intensity-peak within a patient's brain around a geometric target-peak-location 131, through intervening skull-tissue intermediate-layer 150 bounded by first boundary surface 151 and second boundary surface 152, where correction phase-shifts are acquired without imaging and without focusing ultrasound onto the skull, the method comprising:

a. operating an array 112 of ultrasound calibration-emitters {CE(m)}={CE(1), CE(2) . . . CE(M)}, an array 117 of ultrasound focus-emitters {FE(n)}={FE(1), FE(2) . . . FE(N)}, and an array 116 of ultrasound calibration-receivers {CR(p)}={$CR_1$, $CR_2$ . . . $CR_P$} disposed around the patient's skull 150 with respect to the target-peak-location 131;

b. determining in a measurement procedure, without imaging and without focusing ultrasound, a plurality of corrected focusing phase-shifts {FPS(n)}= {FPS(1) . . . . FPS(N)} for the ultrasound focus-emitters {FE(n)} array 117, one focusing phase-shift FPS(n) per focusing-emitter FE(n), by:

i. defining, or having a pre-defined, plurality of distinct calibration-emitter:calibration-receiver triplets {[CE(j),CR(k1),CR(k2)]};

ii. performing a measurement procedure, for selected calibration-emitter:calibration-receiver triplets [CE(j),CR(k1),CR(k2)] of {[CE(m),CR(p)]}, of measuring, without ultrasound imaging and without focusing ultrasound, a measured echo time difference METD(j,k1,k2) between an outer-skull-surface reflection-time and an inner-skull-surface reflection-time of ultrasound test signal that is emitted from the calibration emitter CE(m) of the pair [CE(j),CR(k1),CR(k2)], iii. generating a measured time delays set {TD(n)} as a function of the measured echo time difference set {METD(j,k1,k2)};

iv. electronically computing, as a function of the measured time delays set {TD(n)}, the plurality of corrected focusing phase-shifts {FPS(n)}= {FPS(1), . . . , FPS(N)};

c. focusing ultrasound around the geometric target-peak-location within the patient's brain by simultaneously irradiating the brain using the array 117 of ultrasound focus-emitters {FE(n)} in relative phases determined by the corrected focusing phase-shifts {FPS(n)};

wherein step (a) is performed so that for the total set of ultrasound emitters TSUE that is the union {CE(m)} ∪ {FE(n)} of the sets of ultrasound calibration-emitters and ultrasound focus-emitters, the measuring is performed so that each calibration-emitter $CE_i$, of the given calibration-emitter:calibration-receiver triplet ($CE_i$, $CR_j$), is operated when it's nearest 20 neighbors in the TSUE are substantially dormant.

In preferred embodiments, each individual emitter of the focus-emitters array produces ultrasound radiation which is unfocussed, in the sense that it is does not generate on its own a focused peak maximum on the skull bone layer.

Stated alternatively, the invention introduces a method for generating an ultrasound intensity-peak within a human subject brain around target-peak-location 131, by delivering ultrasound through the skull 150, the skull having an outer surface 151 and inner-facing second boundary surface 152, the method comprising first performing an ultrasound-based calibration procedure and subsequently forming an ultrasound peak around the target-peak location 131 using phase-shift data acquired during the calibration procedure, wherein:

a. the calibration procedure comprises subjecting the skull to a series of unfocused ultrasound skull-probe (USP) events such that:

i. during each one of at least 10 different USP events, a different respective subset of an array 112 of ultrasound calibration-emitters {CE(m)}={CE(1), CE(2) . . . CE(M)} is active and a different respective majority-subset of the complete set of ultrasound emitters (CSUE) is dormant;

ii. each of the at least 10 different USP events probes the skull with unfocused ultrasound at a different maximum-intensity location;

iii. during each of the at least 10 different USP events, reflected ultrasound is received by one or more ultrasound receivers of an array 116 of ultrasound calibration-receivers {CR(p)}={CR(1), CR(2) . . . CR(P)};

b. the ultrasound peak is formed by an array 117 of ultrasound focus-emitters {FE(n)}={FE(1), FE(2) . . . FE(N)};

c. before the forming of the ultrasound peak, a plurality of corrected focusing phase-shifts {FPS(n)}= {FPS(1) . . . . FPS(N)} are computed for the ultrasound focus-emitters {FE(n)} array 117, one focusing phase-shift FPS(n) per focusing-emitter FE(n), by:

i. defining, or having a pre-defined, plurality of distinct calibration-emitter:calibration-receiver triplets {[CE(j),CR(k1),CR(k2)]};

ii. performing a measurement procedure, for selected calibration-emitter:calibration-receiver triplets [CE (j),CR(k1),CR(k2)] of {[CE(m),CR(p)]}, of measuring, with unfocused ultrasound, a measured echo time difference METD(j,k1,k2) between a time of first echo from an outer-skull-surface reflection and time of second echo from an inner-skull-surface reflection of an ultrasound test signal that is emitted from the calibration emitter CE(m) of the pair [CE(j),CR(k1),CR(k2)];
iii. generating a measured time delays set {TD(n)} as a function of the measured echo time difference set {METD(j,k1,k2)}; and
iv. electronically computing, as a function of the measured time delays set {TD(n)}, the plurality of corrected focusing phase-shifts {FPS(n)}={FPS(1), . . . , FPS(N)};
d. forming the ultrasound peak in the brain by operating the array 117 of ultrasound focus-emitters {FE(n)} in relative phases determined by the c corrected focusing phase-shifts {FPS(n)}.

In some embodiments, the measurement procedure, for selected calibration-emitter:calibration-receiver triplets [CE(j), CR(k)] of {[CE(m),CR(p)]}, of measuring, without imaging and without focusing ultrasound, a measured echo time difference METD(j,k1,k2) between an outer-skull-surface reflection-time and an inner-skull-surface reflection-time of ultrasound test signal that is emitted from the calibration emitter CE(m) of the pair [CE(j), CR(k)] comprises:
i. Emitting a test-signal from calibration emitter CE(m);
ii. Detecting reflected test-signal in calibration-receiver sensor CR(p);
iii. Extracting reflection measured echo time difference METD(j,k1,k2) between the test signal reflection from the intermediate-layer first and second boundary surfaces In some embodiments, TD(n) as a function of the measured echo time difference set {METD(j,k1,k2)} is such that, for the majority of n, TD(n)=METD(j,k1,k2) where CE(m) is the nearest calibration-emitter to the focus-emitter FE(n). In particular, there are embodiments where the array of calibration-emitters is the same physical elements as the focusing-emitters, i.e., {CE(m)}={FE(n)}.

In some embodiments, the ultrasound calibration-emitters are transceivers which can be operated also as receivers. Therefore, in some embodiments the array of calibration-emitters is comprising the same physical elements as the calibration-receivers. Hence these elements activation is switched between emitter and receiver functionality.

In some embodiments, TD(n) as a function of the measured echo time difference set {METD(j,k1,k2)} is such that, for the majority of n, TD(n) is a weighted average of the subset {METD(j,k1,k2)} including the calibration-emitters CE(m) nearest and next-nearest to the focus-emitter FE(n). For example, TD(n) may be equal to the average of selected METD(j,k1,k2) associated with nearest neighbors CE(m) calibration emitters.

The time delay set {TD(n)} is computed such that TD(n) is a weighted sum of METD(j,k1,k2) elements associated with the subset of calibration-emitters {CE(j),n} which are geometrically related to focus-emitter FE(n).

The simplest case is where the focus-emitter array {FE(n)} is positioned at the same location or in great proximity to the location of the calibration-emitters {CE(j)}. For example, where the focus emitters and calibration emitters are physically the same transducer element and the transducer array is not moved much or at all between the calibration and focusing procedures. In such a case, the geometrical association is essentially an identity. Yet, in more complex situations, where the focus-emitters array {FE(n)} is positioned at a different location from the calibration-emitters {CE(j)}, the geometrical association is more involved, as discussed below with respect to FIGS. 45A,45B,45C.

In some embodiments, the value of TD(n) is a function of the measured echo-difference set {METD(j,k1,k2)} such that contributions from METD(j,k1,k2)} values are weighed higher where CE(j) is a nearer calibration-emitter to the location to the focus-emitter FE(n).

In some embodiments, the value of TD(n) is a function of the measured echo-difference set {METD(j,k1,k2)} such that contributions from METD(j,k1,k2)} is weighed highest where CE(j) is a nearest calibration-emitter to the location to the focus-emitter FE(n). For example, the value of TD(n) is set equal to METD(j,k1,k2)}, where CE(j) is a nearest calibration-emitter to the location to the focus-emitter FE(n).

In some embodiments, the value of TD(n) is a weighted sum of the elements of the measured echo-difference set {METD(j,k1,k2)} such that contributions from METD(j,k1,k2)} is weighed highest where CE(j) is a nearest calibration-emitter to the location to the focus-emitter FE(n). For example, the value of TD(n) is set equal to the weighted average of two METD(j,k1,k2)} associated with the two nearest calibration-emitters to the location to the focus-emitter FE(n), with the weight proportional to their distance from the focus-emitter FE(n).

In some embodiments, FPS(n)=(FT0(n)+CT(n)), where CT(n) is a function of TD(n)/2 and where {FT0(n)} is a delay set used for a uniform-space focusing of said ultrasound array.

In some embodiments, the complete set of ultrasound emitters (CSUE) is the sum of ultrasound calibration-emitters {CE(m)} and the set of ultrasound focus-emitters {FE(n)}.

In some embodiments, a dormant emitter is considered to be an emitter whose simultaneous intensity is less than 80% of the intensity of the highest intensity active emitter.

In some embodiments, a dormant emitter is considered to be an emitter whose simultaneous intensity is less than 50% of the intensity of the highest intensity active emitter.

In some embodiments, a dormant emitter is considered to be an emitter whose simultaneous intensity is less than 20% of the intensity of the highest intensity active emitter.

In some embodiments, a dormant emitter is considered to be an emitter whose simultaneous intensity is less than 10% of the intensity of the highest intensity active emitter.

In some embodiments, the position of the array 117 of focus-emitters {FE(n)} and array 112 of calibration-emitters {CE(n)} during the focusing is the same as during the measurement procedure.

In some embodiments, the position of the array 112 of calibration-emitters {CE(n)} remains the same throughout the measurement procedure.

Figure 29:
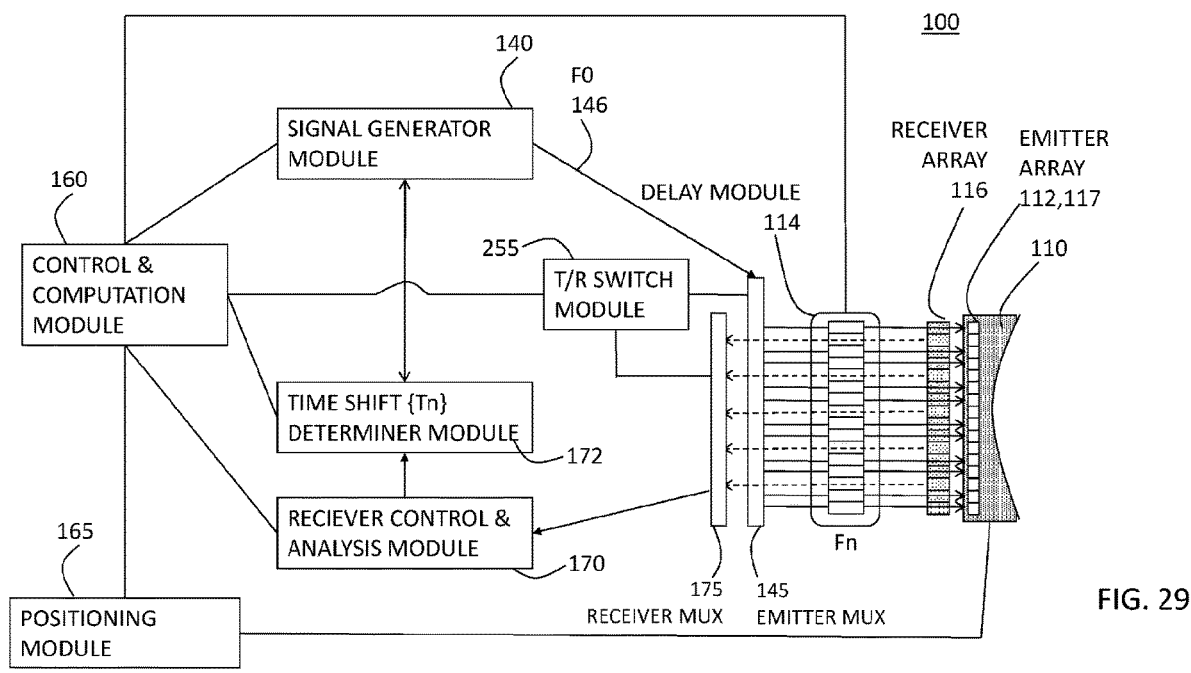
FIG. 29 illustrates an embodiment of embodiment of the invention system schematic architecture for intra-cranial focusing with skull aberration calibration.

As illustrated in FIG. 29, the invention introduces a system for focusing ultrasound into a target brain tissue when having an intervening skull-tissue 150 intermediate-layer bounded by first 151 and second 152 boundary surfaces, using unfocused ultrasound sensing, the system comprising:
a. an array 117 of focus-emitters {FE(n)} of ultrasound transducer elements for generating an ultrasound focus in the target tissue;
b. a delay module 114 for creating a delay set {F(n)}, and a control facility 160 configured to set relative phases of the signal between the focus-emitters {FE(n)} transducer elements according to delay set {F(n)}; the delay module capable of producing a base-delay set {FT0(n)} used for a uniform-space focusing of said ultrasound array on a target location in hypothetical uniform target tissue;

c. an array 112 of calibration-emitters {CE(m)} of ultrasound transducer elements for generating ultrasound test signals;

d. an array 116 of ultrasound calibration-receiver elements {CR(p)} associated with the calibration-emitters {CE(n)};

e. the control system 160 further capable for selectively activating sub-sets of calibration-emitters {CE(m)};

f. a detection module 170, in communication with the calibration-emitters {CE(m)} and the calibration-receiver elements {CR(p)} and in communication with the control module 160;

i. the detection module 170, enabling receiver control and analysis, for identifying and processing ultrasound echo test signals reflected by said intermediate-layer first 151 and second 152 boundary surfaces—using a selectively activated calibration-emitter element CE(m) and a paired selected associated calibration-receiver element CR(p);

ii. the detection module 170 further comprising a computation module configured to: (A) receive data associated with the echo signal associated with the activated calibration-emitter element CE(n), based at least in part on the data; (B) compute the reflection time difference TD(n) between the test signal reflection from the intermediate-layer first and second boundary surfaces; and (C) compute a corrected-delay FPS(n) proportional to half the reflection time difference TD(n), such that FPS(n)=(FT0(n)+CT(n)) where CT(n) is a function of TD(n)/2;

iii. the detection module 170 serially performing a measurement of such echo signals from a plurality of selected array calibration-emitters elements (e.g., majority of array calibration-emitter elements), thereby generating a corrected delay set {FPS(n)};

g. the control system 160 and delay module 114 capable of driving the transducer array 117 of focus-emitter elements {FE(n)} at the corrected delay set {FPS(n)}, so as to generate an improved the ultrasound focus compared with the case where the relative phases where {FT0(n)}.

h. wherein the control module 160 is configured for a series of unfocused ultrasound skull-probe (USP) events such that:

i. during each one of at least 10 different USP events, a different respective subset of an array of ultrasound calibration-emitters {CE(m)}={CE(1), CE(2) . . . CE(M)} is active and a different respective majority-subset of the complete set of ultrasound emitters (CSUE) is dormant;

ii. each of the at least 10 different USP events probes the skull with unfocused ultrasound at a different maximum-intensity location;

iii. during each of the at least 10 different USP events, reflected ultrasound is received by one or more ultrasound receivers of an array of ultrasound calibration-receivers {CR(p)}={CR(1), CR(2) . . . CR(P)};

In some embodiments, the system is such wherein the function CT(n)=(V2/V1−1)*TD(n)/2, where V2 is an estimated average speed of sound in the intermediate-layer within at least 20% accuracy and V1 is an average speed of sound in the target tissue within at least 10% accuracy.

In some embodiments, the system is such wherein the control module for selectively activating sub-sets of calibration-emitters {CE(m)} is selectively activating individual array elements CE(m)) while maintaining other array elements in a dormant state.

In some embodiments, the system is such wherein the detection system serially performing a measurement of such echo signals from a plurality of selected array calibration-emitters elements, is serially performing the measurement on a majority of array calibration-emitter elements, In some embodiments, the system is further comprising a positioning module capable of maintaining the position of the emitter phased array with respect to the target tissue.

In some embodiments, the system is such wherein a transducer emitter element E(n) can physically serve also as a receiver element R(m), associated with same emitter n (m=n) and/or associated with a different emitter element n' (m=n').

In some embodiments, the system is having at least two modes of activation, (i) a focusing beam mode at which the majority of the emitter array elements are simultaneously emitting ultrasound to create a focus peak, and (ii) an calibration mode at which only a minority of emitter elements are simultaneously activated and at least one receiver element is sensing the reflected signals and transmitting them for analysis to the computation module. In some embodiments, the minority of emitter array elements is less than 10% of the array elements, or less than 1% of the array elements. In some embodiments, the minority of emitter array elements is an individual single element.

It helps to highlight from the outset certain distinguishing feature of the present invention embodiments in comparison with known art. FIG. 22E illustrates a known art embodiment where the focusing emitter module 11 is complemented by a receiver module 12 which is significantly distanced in space from large portion of the emitter module. It will be argued that such geometric combination of emitter and receiver modules are ineffective for realization of the present invention. In contrast, as will be further elaborated below, embodiments of the present invention comprise a distributed array of receiver array elements which is roughly paralleling in space the distribution of emitter array element, as exemplified in FIG. 8.

It is well known in the art that a proper coupling medium 118 needs to fill the gap between the transducer surface 113 and skin surface, in order to reduce ultrasound reflection from the entry interface into the subject body. In embodiments, the coupling medium is deformable, such as a liquid or gel, in order to be able to conform to the skin contour. In embodiments, the coupling medium has speed of sound similar to the skin tissue.

FIGS. 22A, 22B, 22C illustrate schematic embodiments of focusing transducer emitter arrays {E(n)}, representing alternative embodiments realizations of the basic transducer array as is known in the professional literature to achieve focusing of ultrasound. It is not meant to be limiting, but to the contrary to exemplify the variety of technical possibilities and combinations for the basic transducer array arrangement which is not core to the inventive step of the present invention.

Figure 2A:
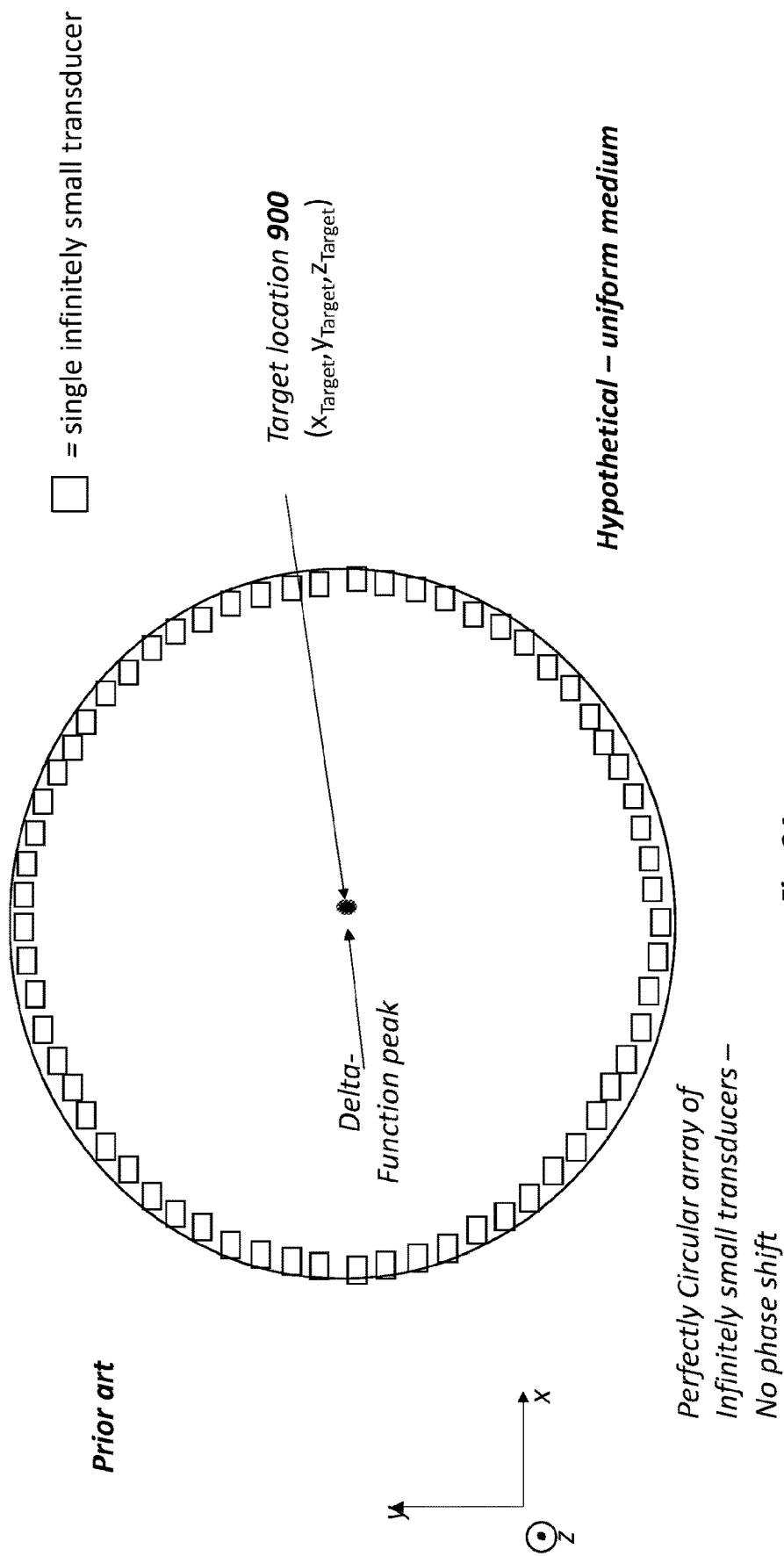
Figure 2B:
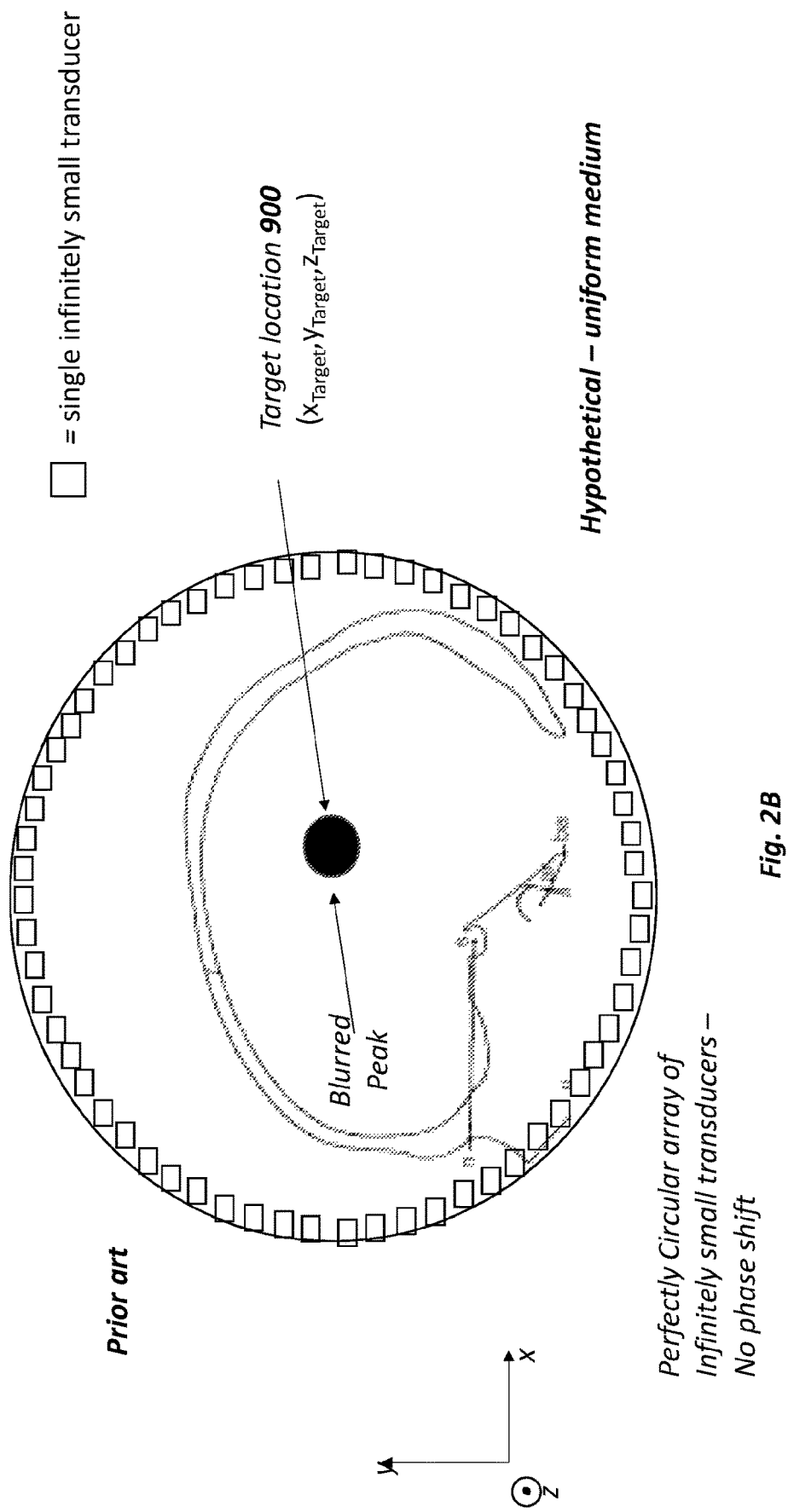

FIG. 2 FIG. 22A illustrates a spherical arrangement of the emitter array {E(n)}, where in a uniform medium the focal peak is generated at the sphere center if all the emitter element are activated in uniform phase delay, i.e., {f(n)=f0} where f0 is a constant.

FIG. 222B illustrates a flat transducer emitter array {E(n)} complemented by an acoustic lens. Thereby, in a uniform medium focal peak is generated at the focus center determined by the acoustic lens if all the emitter elements are activated in uniform phase delay, i.e., {f(n)=f0} where f0 is a constant.

FIG. 222C illustrates a flat transducer emitter array {E(n)} with variable relative phase delay between the array element. Thereby, in a uniform medium focal peak is generated at the focus center determined by the set of time delays {f(n)} selected such that the signals emitted from each associated emitter E(n) is a arriving in-phase to to desired focal point to create a constructive interference.

Since any of the above and also combination of the above transducer array models can be used to realize the present invention, we use a generic representation, illustrated in FIG. 23A, to signify the focusing transducer 110. Also highlighted in FIG. 23A are certain related aspects of the focusing transducer 110, such as the focus peak location 111 which is also the focal center of the focusing transducer in uniform medium 99, the emitter array 112 component of the focusing transducer, focusing transducer surface 113, and the focal zone 119 area boundary, preferably defined at half maximum peak intensity.

FIG. 22D illustrates schematically a two-dimensional (2D) array of emitter elements. This is meant to highlight the fact that the illustrations in other figures herein, although look graphically like lines, stand to represent 2D and/or 3D arrangements of ultrasound transducer arrays. Hence the simplified graphical representation of other figures is only for the purpose of visual simplicity and not meant to be limiting.

FIGS. 23B and 23C illustrate the ability to steer the focus peak location to more than one location in space using appropriate time delay set for the transducer array, as is well known in the art of ultrasound transducer arrays.

Figure 25:
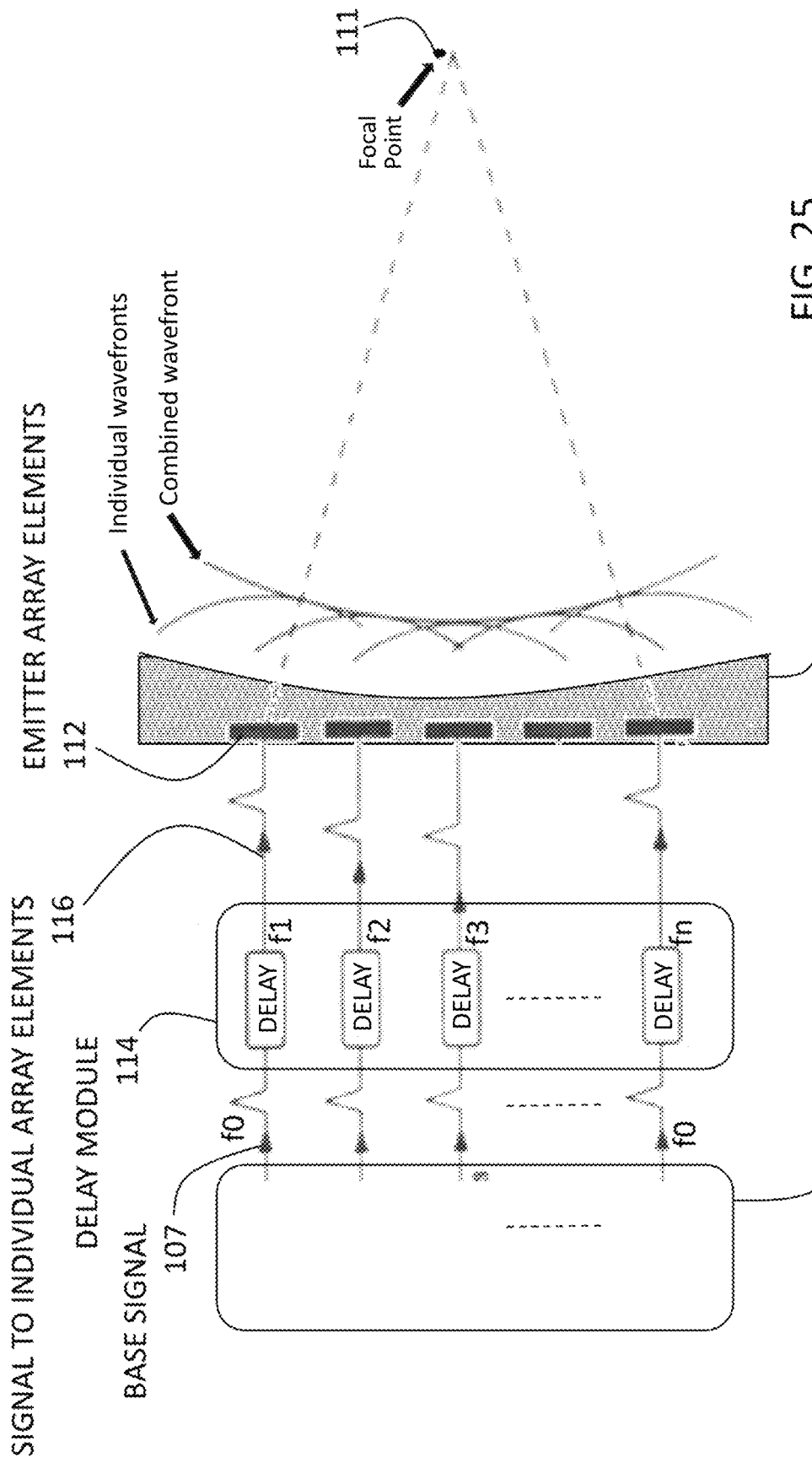
FIG. 25 illustrates selected functional components of the invention transducer array.

FIG. 25 highlights additional features of an embodiment of the invention system. As is typical in the art of transducer phased array, a base-signal generator 115 produces base signal f0 107. The base-signal f0 is input to and manipulated by a delay-module 114. The delay-module 114 generates a set {F(n)} of time shifted signals 116 each shifted by a time delay F(n) with respect to the input base-signal f0. Optionally, also and amplitude modification of the base-signal amplitude may be generated for each time shifter signal {f(n)}. Optimal focusing is obtained when all signals of the set {f(n)} arrive in-phase to a particular focus peak point 111 at which they have maximum constructive interference.

FIGS. 26A, 26B, 26C illustrate a principal problem and goal of the present invention. FIG. 26A illustrates the focus of ultrasound created by transducer 110 when driven by signal delay set {FT0(n)}, where the ultrasound waves propagate in uniform medium 99 throughout the path from the transducer surface to the focus peak 111 with focus zone area 119.

The calibration emitters array (CEA) has a characteristic size CS(CEA). To achieve good focus at depth of about 26 Cm, the calibration array needs to be of about the same size. Hence the CEA characteristic size is at least 5 cm, preferably between 26 Cm to 10 cm. For completeness, since stray elements are of little effect, we shall define the characteristic size CS(CEA) as a diameter of the smallest sphere which includes a 80% of the emitters calibrations emitters array.

Each member CE(j) of the calibration emitters array is displaced from the skull by DISPL[CE(j)]. For good calibration, the calibration emitters (hence, the calibration array) should be in proximity of the skull.

Preferably the majority of calibration emitters are within 23 Cm of the skull skin surface, better within 22 Cm of the skull skin surface, better within 1 cm of the skull skin surface. i.e., for a majority of the calibration emitters of the calibration emitters array, a ratio between DISPL(CE(j)) and CE(CEA) is at most ½, preferably at most ⅓, preferably at most ¼.

As illustrated in FIGS. 26B and 26C, the uniform medium 99 is the matching medium between the transducer 110 and the skull. In contrast, the intracranial skull medium 98 is typically non-uniform. It is preferred, and common in the art, to select a matching medium 99 which is of uniform ultrasound properties and which is characterized by speed of sound which the same (e.g., within less than 10% difference of) as or close to (e.g., within less than 10% difference of) the average speed of sound of the intracranial brain tissue 98.

FIG. 26B illustrates the focus of ultrasound created by transducer 110 when driven by the same signal delay set {FT0(n)} as in FIG. 26A, but where the ultrasound wave paths pass through an intervening skull-tissue intermediate-layer bounded by first 151 and second 152 boundary surfaces within otherwise same uniform medium 99 in the path from the transducer surface to the focus peak 121 with focal zone area 129. Due to the intervening layer, a non-optimal interference is creating the focus peak 129 with focal zone area 129 larger than the uniform medium focal zone 119 and in many cases both shifted focus peak location 121 and more than one focus peak location. i.e., among its configurations, the delay set electronic control facility is configured to set relative phases of the signal between the focus-emitters {FE(n)} transducer elements according to delay set {F(n)}; the delay module capable of producing a base-delay set {FT0(n)} used for a uniform-space focusing of said ultrasound array on a target location in hypothetical uniform target tissue As illustrated in FIG. 26C, a principal goal of the present invention is to drive the focusing transducer 110 with an calibrated focusing signal delay set {FPS(n)}={FT0(n)+CT(n)/2}, such that where the ultrasound waves path pass through an intervening skull-tissue intermediate-layer bounded by first and second boundary surfaces within otherwise same uniform medium 99 in the path from the transducer surface to the focus peak 131 with focal zone area 139. Due to the calibrated focusing signal delay set {FPS(n)}, an improved interference is creating the focus peak 139 with focal zone area 139 smaller than the focal zone 129 created when the focusing transducer 110 with an uncalibrated focusing signal delay set {FT0(n)}.

The key problem is how to determine the calibration set {CT(n)}. The present invention provides a method and system for determine the calibration set {CT(n)} and thereby creating an improved focus when the focused ultrasound waves path pass through an intervening skull-tissue intermediate-layer bounded by first and second boundary surfaces within otherwise approximately uniform medium 99 in the path from the transducer surface to the focus peak.

We conceptualize the method as a procedure composed of two major stages: (i) Measurement procedure "PROC-1", and (ii) calibrated focusing irradiation application procedure "PROC-2".

The measurement procedure PROC-1 can be sub-divided into two prominent sub-tasks: (a) physical measurement procedure "MEASURE", and (b) computational analysis "ANALYSIS" from which the key outcome is the determination of a time-set {TD(n)} from which is determined the calibration set {CT(n)}, where each element CT(n) is a function of corresponding TD(n).

The calibrated focusing irradiation application procedure "PROC-2" can be sub-divided into two prominent sub-tasks: (a) Input parameters set-up, and (b) irradiation application process.

In the calibrated focusing irradiation application procedure "PROC-2", the calibration set {CT(n)} from PROC-1, the system is activating the emitters array with the corrected set {FPS(n)} of input parameters phases. The irradiation application process itself is determined by clinical goals (e.g., nerve stimulation, tissue ablation, etc. . . . ).

The innovation is primarily contained in the preparatory measurement process PROC-1 method and apparatus and from it the core outcome is the values of the calibration set {CT(n)} of input parameters that is used to define the corrected set {FPS(n)} of phases.

FIG. 27 illustrates an embodiment of the present invention. When a test signal is emitted from an individual emitter 141m as calibration emitter CE(m) as calibration emitter CE(m) selected from the transducer emitters array {CE(m)}, there is partial reflection from the first and second boundary surface 151 & 152 of the intermediate tissue layer 150. These reflections can be detected in any one of possible receiver sensors of the receiver array 116. For example, we consider two possible receiver sensors 161p as paired calibration receiver CR(p) as paired calibration receiver CR(p), or 162p, to be paired with emitter 141m as calibration emitter CE(m). In each of the receiver sensors, there will be a time difference "TD(n)" between the signal reflection from boundary surface 151 and surface 152. The specific time difference TD(n) is due primarily to the extra path travel within the intermediate skull layer 150 for the signal reflection from boundary surface 152.

As illustrated in FIG. 27, the reflected signal path 172 arriving to receiver sensor 161p as paired calibration receiver CR(p) is different from the path of the reflected signal path 174 arriving to receiver sensor 162p. In particular, there is a difference in the length of the partial path through the intermediate skull layer 150. Consequently, there would be a different value of TD(n) if the refection is measured with paired receiver 161p as paired calibration receiver CR(p) or with paired receiver 162p.

In the path to the focus peak 111 from the emitter 141m as calibration emitter CE(m), the sound wave passes once through the intermediate skull layer 150 width. In contrast, the reflected test signals, 172 and 174, from boundary 152, each passes twice through the intermediate skull layer 150 width (corresponding to the incident and reflected portions of the path within the layer 150). Therefore, half of the reflected test signals time difference TD(n), i.e., (TD(n)/2), is a good approximation to the time shift contribution of the intermediate skull layer 150 to the total travel time of the focused beam from the particular emitter 141m as calibration emitter CE(m) to the focus peak location 111. Therefore, in embodiments of the present invention, adjusting the relative time shift by subtracting (TD(n)/2) from FT0(n) substantially eliminates the phase shift contribution of the intermediate skull layer 150 to the total travel path from the emitter 141m as calibration emitter CE(m) to the focus peak 111. Hence, in embodiments the calibrated focusing delay set {FPS(n)}={(FT0(n)+CT(n))} is then use for irradiating the target tissue using the ultrasound transducer array emitter elements {E(n)} having a corrected-delay {F(n)}={FPS(n)} to create a focus peak 131 with an calibrated focusing focal zone 139 of smaller cross section area than if irradiated with uncalibrated focusing delay set {FT0(n)}.

It remains to be decided which receiver sensor measurement to use for the determination of TD(n). Ideally, one would like to have a reflected path which is exactly twice the length of the focused beam path within the intermediate skull layer 150.

One preferred approximation, as illustrated for the path 172, is a test signal path for which at least the incident portion of the test signal path to be the same as the focused beam path 170 to the focus peak 111. For such an embodiment, fast switching needs to be operated to switch the emitter transducer to receiver mode of operation within the duration of the reflection time. To a good approximation, for ray 370, defined to be the ultrasound propagation "ray" from emitter 341m as would be in the selected uniform medium 99 traversing the focus peak 111, the path of ray 370 through the intermediate skull layer 150 is very close to the real path of ultrasound ray from emitter 141m as calibration emitter CE(m) to the focus peak 111.

Another preferred embodiment approximation is one for which the same physical transducer array element is used for both test signal emitter and as receiver sensor. Another preferred embodiment approximation is one for which, as illustrated for the path 171, for a given emitter 141m as calibration emitter CE(m) the associated receiver sensor 161p as paired calibration receiver CR(p) is a neighboring (e.g., nearest neighbor) transducer sensor element 161p as paired calibration receiver CR(p). A question in such embodiments is which direction of neighbor to choose as sensor placement relative to the emitter element. For example, should it be one to the left or to the right of the emitter element. The better approximation depends on the relative curvature of the entry boundary 151 of the intermediate skull layer 150 compared with the curvature of the focus beam at that boundary surface. For example, as illustrated in FIG. 27, if the boundary surface 151 is flatter than the better approximation is to have for emitter element 141m as calibration emitter CE(m) the associated test receiver sensor 161p as paired calibration receiver CR(p) to the right of it. The opposite choice, of a receiver sensor to the left would be preferred if the boundary surface 151 would be of higher curvature than the focused beam. For most practical purpose applications, the difference between left and right sensors are minuscule, and an embodiment is to have a fixed pre-determined association of a given emitter sensor 141m as calibration emitter CE(m) to s fixed receiver sensor 161p as paired calibration receiver CR(p).

There is no need for unique exclusive one-to-one association of a sensor to an emitter. In some embodiments, the number of receiver sensors is smaller than the number of emitter elements in {E(n)}. For example, as illustrated in FIG. 8, in an embodiment of 2D array transducer exemplified by the array 212, receiver element 261n can serve for test signal from several nearest neighboring emitter elements marked by the dashed circle, such as 241n and 241m.

In some embodiments, the emitter and receiver sets are physically distinct. In some other embodiments, the emitter and receiver sets are overlapping. For example, referring to FIG. 8, the array of receiver element marked by shaded fill cells may be distinct from the array of emitter elements marked by white fill cells. Alternatively, the shaded fill cells can mark a sub-set of the transducer elements which may be switched between acting as emitter and receiver functionality.

It is preferred to be able to selectively activate individual emitter and/or receiver elements from the physical arrays sets. For example, for test signal and calibration procedures, one is preferably activating the array emitter elements serially or in sub-sections (i.e., not all together as for focus creation), and respectively receiving and/or analyzing the echo received signals only of the associated receiver sensors. That is relevant both for embodiments where the emitter and receiver sets are physically distinct and for embodiments where they are overlapping. In embodiments, the switching control and activation of the emitter 112 and/or receiver 116 arrays are managed by a controller module 255.

FIG. 29 illustrates an embodiment the invention system for focusing ultrasound into a target tissue when having an intervening skull-tissue intermediate-layer 150 bounded by first 151 and second 152 boundary surfaces, using ultrasound sensing, the system comprising:

A focusing transducer 110 comprising an emitter phased array {E(n)} 112 of ultrasound transducer elements for generating an ultrasound focus in the target tissue. At least most transducer elements having means connected thereto for variably setting a delay for that emitter transducer E(n), including a delay module for setting delay set {F(n)} of signals delay to associated emitter elements {E(n)}.

A receiver array 116 comprising a plurality of ultrasound receiver elements {R(n)} associated with emitter elements {E(n)}; The receiver array 116 is connected to and controlled by a receiver control module 170.

A transmit/receive controller "T/R controller" module 255 for directing the activation and switching of individual elements of the emitter and receiver arrays. The T/R module 255 comprising connections to the emitters array 112, to the receiver array 116, to the signal generator module 140 and to the control & computation module 160.

An emitter mux module 145 receives input signal from the signal generator 140, the associated activation delay set {TD(n)} from control module 160, and the array elements activation directed by T/R module 255. The emitter mux 145 transmit the activation signals to the emitter array 112 elements {E(n)}.

For focusing-mode all, or at least the majority, of the emitter array 112 elements {E(n)} are activated simultaneously, with associated delay set {F(n)} of a common action-signal, to generate a focus peak at a certain location.

For calibration-mode a minority, preferably one, of the emitter elements E(n) is activated at a time, preferably with a distinct "test-signal", which may be preferably different from the action-signal. The test signal reflected echo-signal is received at an associated "paired" receiver element of the receiver set 116 and transmitted for analysis to receiver control module 170. It is expected that the received reflected signal would include multiple reflections from various material boundaries such as skin surface, fatty tissue, and the intermediate skull bone layer 150. As highlighted by the table of FIG. 30C, since the biggest difference of speed of sound is cranial ultrasound is between bone tissue and its neighboring tissue, we expect that the reflection from intermediate skull tissue layer 150 boundaries 151 and 152 can be singled out by having the biggest reflection amplitudes compared with other parts of the echo signal. The receiver control module extracts the from the received signal the echo component associated with reflections from the first and second boundary surfaces 151 and 152 of the intermediate skull layer 150. The time difference between these reflection signals is determined by the time-shift determiner module 172 to create the reflection time difference TD(n). Repeating the process serially for multiple, preferably most or preferably all, of the emitter elements, lead to obtaining a reflection time difference {TD(n)}.

After calibration mode procedure, the focusing mode is activated with the emitter array 112 driven with an calibrated focusing time-delay set {FPS(n)}={FT0(n)+CT(n)} to create an calibrated focusing focus peak.

For effective focus improvement by the invention calibration procedure. The positioning module 165 maintains the transducer module 110 at a fixed orientation relative to the target tissue for both the calibration procedure and the focusing mode activation.

FIG. 30A and FIG. 30B highlight some aspects of the extraction of the reflected signals and calculation of the reflection delay time TD(n). FIG. 30A highlights the multiple layers of tissue on the path from the transducer emitter outside of the head to the focus peak within the skull. FIG. 30B illustrates schematically the reflection of emitted test-signal 155, first reflected signal 156 from boundary surface 151 is received at the receiver sensor, and later the reflected signal 157 from the boundary surface 152 of the intermediate skull layer 150 is received at the receiver sensor. The arrival time difference between signal 156 and 157 corresponds to the detected test-signal delay TD(n).

Figure 32:
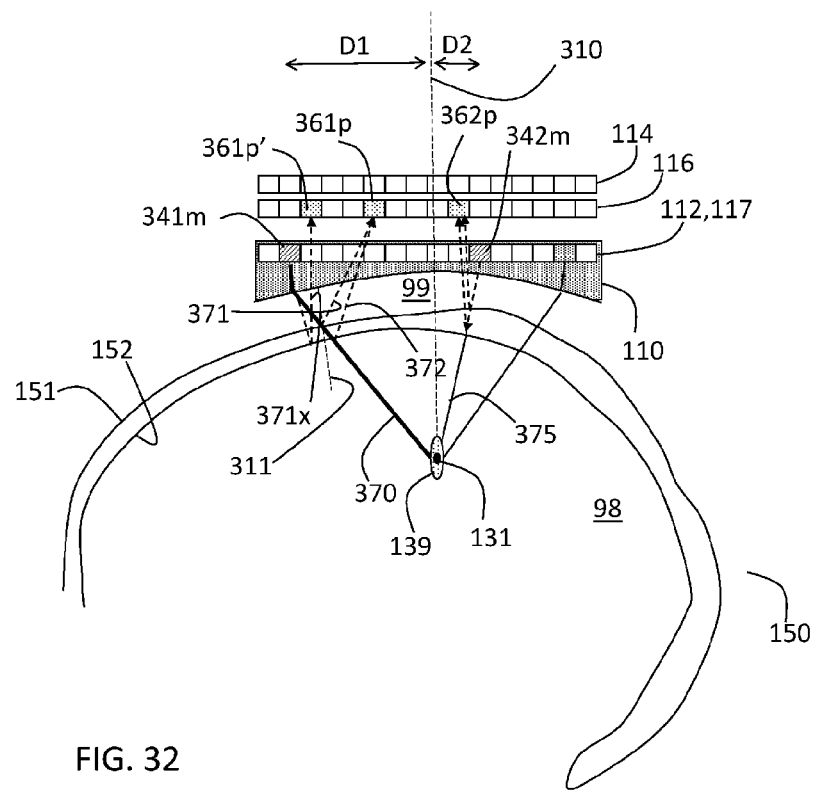
FIG. 32 illustrates an embodiment of selection of receiver sensors association with emitter sensors.

As previously discussed, better focusing calibration would be obtained if the test signals path through the intermediate tissue layer is better matching (i.e., closer) to the path through the intermediate skull layer of focusing beam to the focus peak location. As illustrated in FIG. 32, the focusing-axis 310 is defined as the line from the focus peak to geometrical center of the transducer array in uniform medium. For a peripheral-emitter 341m that is further from the focusing-axis 310 than the distance for central-emitter 342m that is closer to the focusing-axis, a better matching of is obtained if the distance D1 between the emitter 341m and associated calibration-receiver 361p is larger than the distance D2 between the emitter 342m and associated calibration-receiver 362p. For some embodiments, for optimal matching, the difference between D1 and D2 can be a factor of two or more. To a good approximation, for ray 370, defined to be the ultrasound propagation "ray" from emitter 341m as would be in the selected uniform medium 99 traversing the focus peak 111, the path of ray 370 through the intermediate skull layer 150 is very close to the real path of ultrasound ray from emitter 141m as calibration emitter CE(m) to the focus peak 111. Reflected ultrasound propagation "ray" 371 is reflected from outer surface of the intermediate skull layer (e.g., skull bone) of incident ultrasound ray 370. Reflected ultrasound propagation "ray" 372 is reflected from inner surface of the intermediate skull layer (e.g., skull bone) of incident ultrasound ray 370. In FIG. 32 it is illustrated that both reflected rays 371 and 372 signals are measured at the same receiver sensor 361p, but this is not meant to be limiting, as will be further elaborated below.

Figure 33:
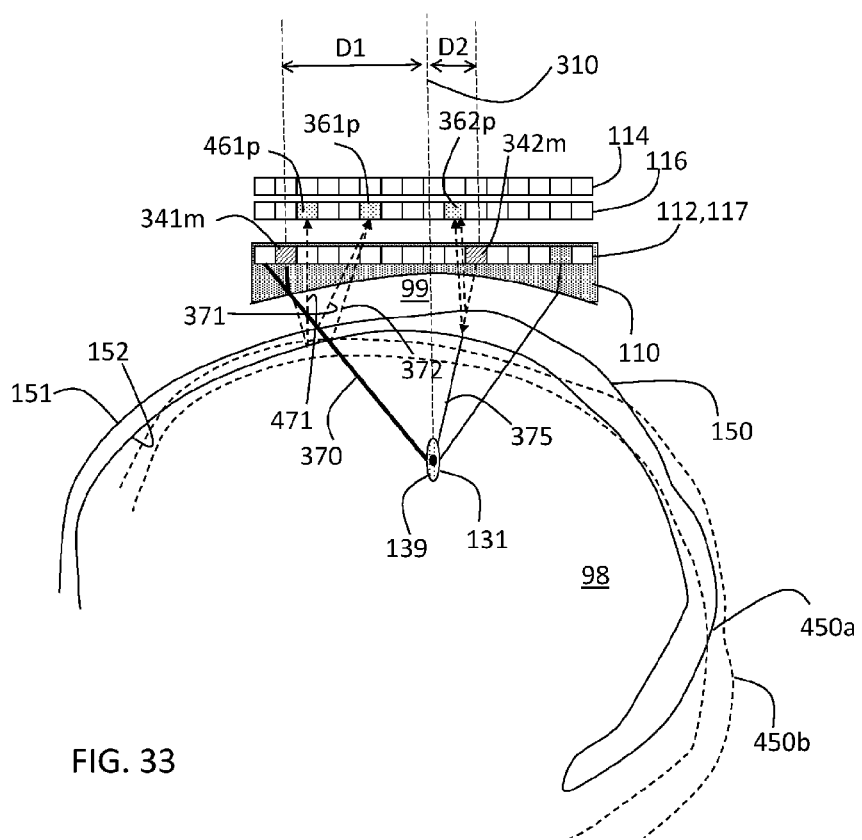
FIG. 33 illustrates an embodiment of selection of receiver sensors association with emitter sensors.

In embodiments, the preferred associated calibration-receiver for optimal path matching is not fixed for all intermediate skull layers, but is dependent on the orientation of the intermediate tissue boundary layers relative to the transducer focusing-axis 310. For example, as illustrated in FIG. 33, for a given emitter 341m, the preferred associated calibration-receiver for optimal path matching may depend on the skull orientation with respect to the transducer array focusing-axis 310. For example, for layer orientation 450a the better optimal receiver is 361p, while for layer orientation 450b the better optimal receiver is 461p. The reason is that the skull orientation changes the intermediate boundary surfaces orientation and hence the ultrasound reflection angles from them. The sensing of the skull orientation with respect to the transducer can also be detected using the ultrasound emitter array 112 and the receiver array 116. i.e., in embodiments of the method of the present invention, prior to the test signal procedure there is a calibration procedure for determining the orientation of the intermediate tissue boundary layers with respect to focusing-axis 310.

Figure 34:
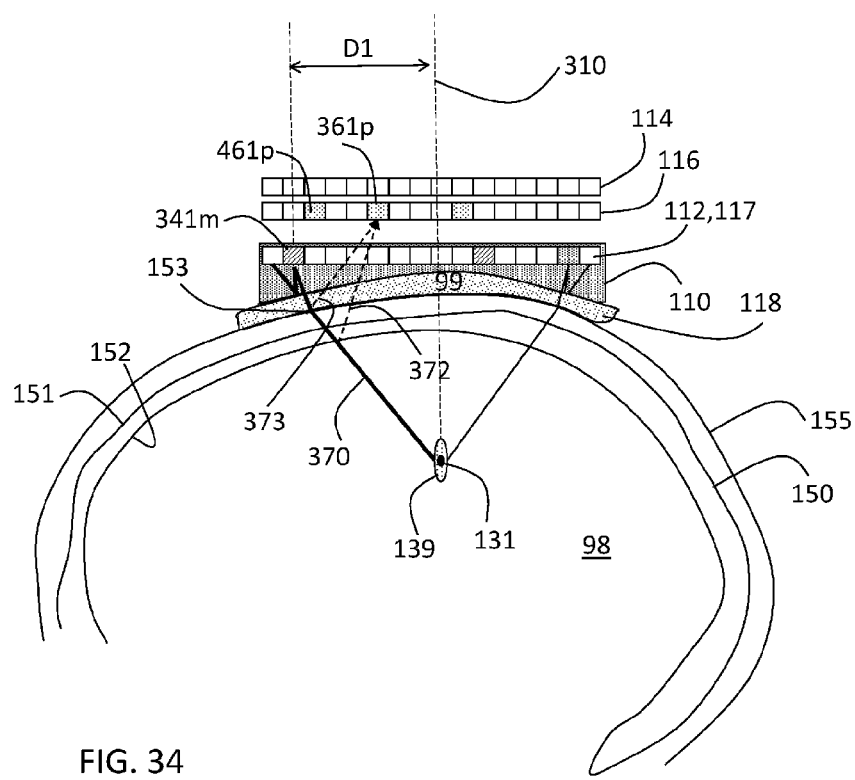
FIG. 34 illustrates an embodiment of selection of receiver sensors association with emitter sensors.
Figure 35A:
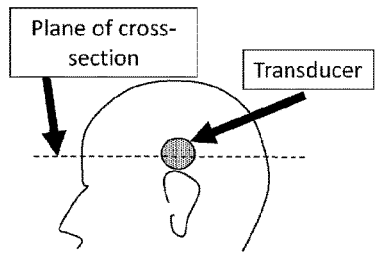
FIG. 35 illustrates basic principles of signal detection from selected surface boundaries.
Figure 35B:
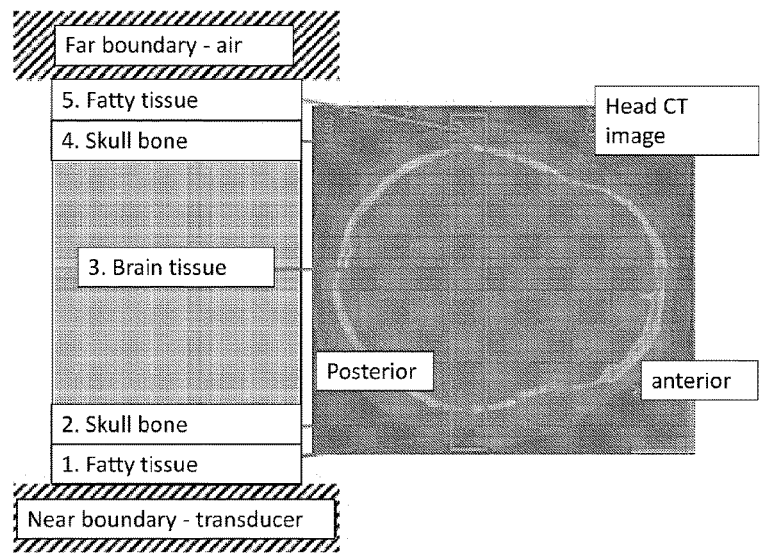
Figure 35C:
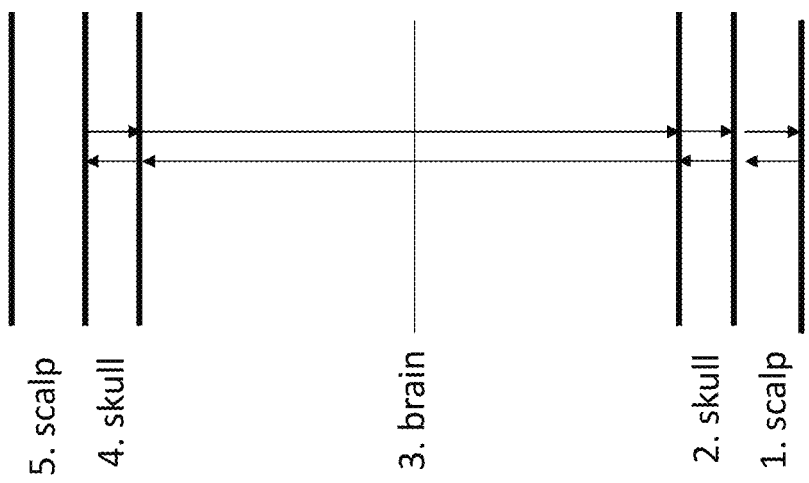

As illustrated in FIG. 34, the aberration effect of the scalp layer (i.e., between the skin surface and the first skull boundary surface 151) is small compared with just the skull bone layer, because (a) the speed of sound in the scalp is very close to the speed of sound in brain tissue and/or the coupling medium 118, and (b) the scalp is relatively uniform in thickness across the surface area of the scalp contact with the device. Hence, the focus of our discussion is on detection and correction of reflections between the first skull boundary entry surface 151 and the second skull bone boundary exit surface 152. Yet, this is not meant to be limiting. The inclusion of the scalp layer 155 is a simple extension of the entry reference to the skin surface 153 entry instead of the bone entry surface 151. Hence, the first reflection delay count would be from the path 173, which is identifiable as known in the art to select among the series of echo received signals.

At different receiver sensor the reflection times may be different. Therefore, the selection of receiver sensors at which time of reflected beams is measured is affecting the time delay correction calibration. i.e., for each calibration-emitter CE(m) there is an associated "paired" calibration-receiver CR(p) at which the echo signal is measured, thus defining the pair [CE(j),CR(k1),CR(k2)]. Different pairing may lead to different measurement and hence different calibration outcome. Some of the difference between various embodiments relates to the method or protocol of selecting the pairing of the calibration-emitter CE(m) there is an associated "paired" calibration-receiver CR(p) at which the echo signal is measured for the calibration ANALYSIS.

Figure 36:
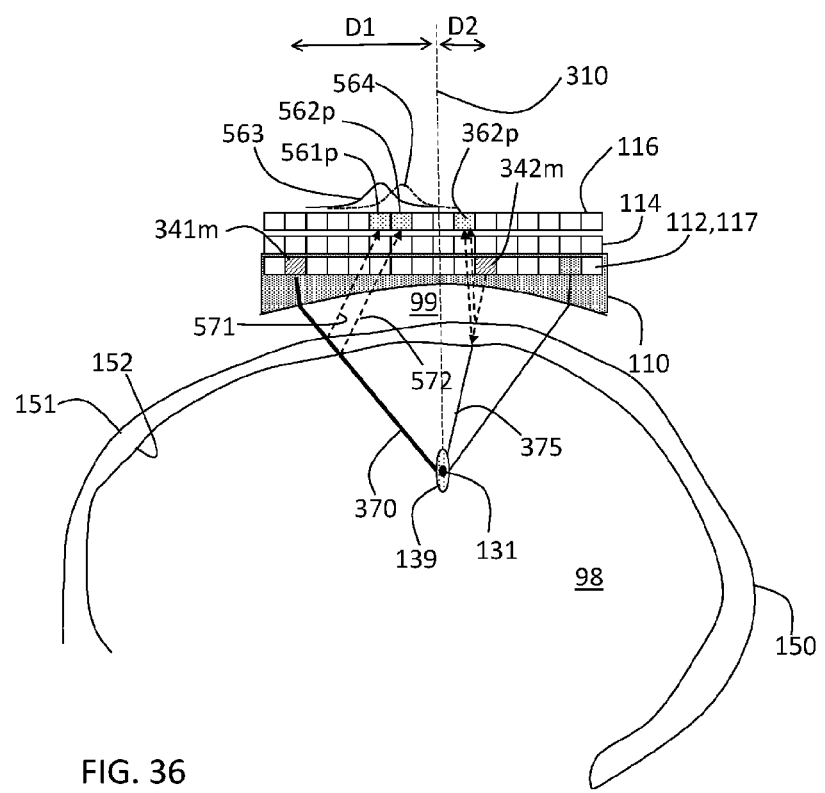
FIG. 36 illustrates an embodiment of selection of receiver sensors association with emitter sensors.
Figure 37B:
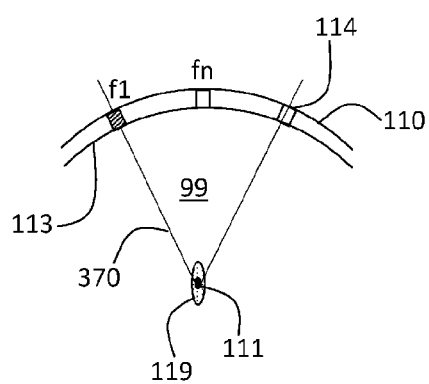
FIG. 37 illustrates schematic representations of the emitter transducer array.
Figure 37A:
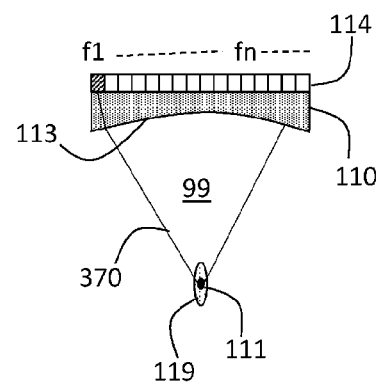

FIG. 36 illustrates a preferred method of receiver sensor selection. As previously discussed, better focusing calibration would be obtained if the test signals path through the intermediate tissue layer is better matching (i.e., closer) to the path through the intermediate skull layer of focusing beam to the focus peak location. When a test pulse is emitted from an individual emitter 341$m$, there is a sufficient time gap to distinguish between arrival at the receiver array 116 of the reflection beam signal 571 from first surface (outer surface) 151 and of reflection beam signal 572 from second surface (inner surface) 152 of the intermediate skull layer 150. The reflected beam signal 571 may be arriving at each receiver of the receiver array 116 at a different time and also at a different intensity with a spatial distribution 563 of intensity which is measured by the receivers array. The reflected beam signal 572 may be arriving at each receiver of the receiver array 116 at a different time and also at a different intensity with a spatial distribution 564 of intensity which is measured by the receivers array. In embodiments, the sensor for timing T1 of the arrival of reflection 571 is timed at receiver 561$p$ at which reflected beam 571 is detected at peak intensity. In embodiments, the sensor for timing T2 the arrival of reflection 572 is timed at receiver 562$p$ at which reflected beam 572 is detected at peak intensity. Repeating the test process for each emitter E(n) we obtain the reflected signals arrival times T1(n) and T2(n).

The time difference between these reflection signals T2(n)−T1(n) is determined by the time-shift determiner module 172 to create the reflection time difference TD(n)= T2(n)−T1(n). Repeating the process serially for multiple, preferably most or preferably all, of the emitter elements, lead to obtaining a reflection time difference set {TD(n)}.

After calibration mode procedure, the focusing mode is activated with the emitter array 112 driven with a calibrated focusing time-delay set {FPS(n)}={FT0(n)+CT(n)} to create an calibrated focusing focus peak.

Figure 38:
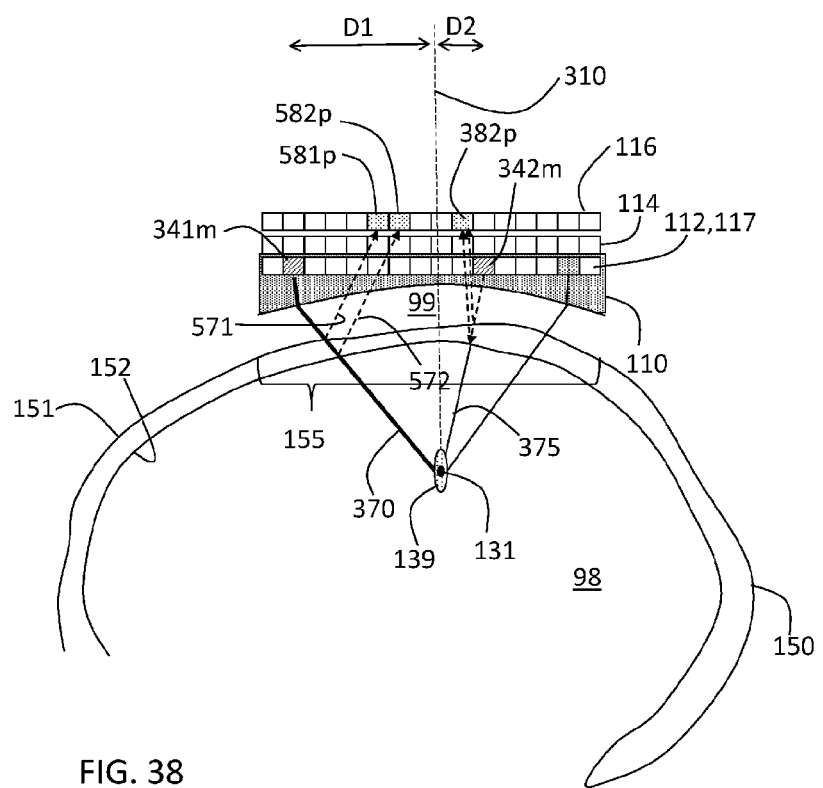
FIG. 38 illustrates an embodiment of selection of receiver sensors association with emitter sensors.

FIG. 38 illustrates a preferred method of receiver sensor selection. As previously discussed, better focusing calibration would be obtained if the test signals path through the intermediate tissue layer is better matching (i.e., closer) to the path through the intermediate skull layer of focusing beam to the focus peak location. When a test pulse is emitted from an individual emitter 341$m$, there is a sufficient time gap to distinguish between arrival at the receiver array 116 of the reflection beam signal 571 from first surface (outer surface) 151 and of reflection beam signal 572 from second surface (inner surface) 152 of the intermediate skull layer 150. The reflected beam signal 571 may be arriving at each receiver of the receiver array 116 at a different time and also at a different intensity with a spatial distribution 563 of intensity which is measured by the receivers array. The reflected beam signal 572 may be arriving at each receiver of the receiver array 116 at a different time and also at a different intensity with a spatial distribution 564 of intensity which is measured by the receivers array.

The previously discussed embodiment, with reference to FIG. 36, had the sensor selection based on the reflected intensity. This has a deficit that the test reflection intensity is not changing if the focus location is moved (e.g., by relative phases shifting it left/right of the transducer axis). Hence, there may be some degradation of the level of aberration fixing for different intended focus locations. In contrast, the intended depiction in FIG. 38 is that the selection of receiver sensor at which reflection time is measured is based on a geometrical determination method. First, the skull section 155 of intermediate skull layer 150 external surface 151 geometry and orientation at the section 155 facing the transducer is assumed to be given or measure by some known method. Generally, the external shape of the skull boundary surface 151 is easy to determine with a variety of well known methods. It is the inner boundary surface 152 which is mostly unknown. Given the surface section 155, the geometrical ray 370 from each emitter element 341$m$ to the intended focus peak 111 is traced. The ray is taken as reflected following classical law of reflection that the incident ray, the reflected ray, and the normal to the surface of the mirror all lie in the same plane. Furthermore, the angle of reflection is equal to the angle of incidence. Thereby, for a target focus location 111, the associated paired receiver for each emitter is selected.

In embodiments, the sensor for timing T1 of the arrival of reflection 571 is timed at receiver 561$p$ at which reflected beam 571 is detected at peak intensity. In embodiments, the sensor for timing T2 the arrival of reflection 572 is timed at receiver 562$p$ at which reflected beam 572 is detected at peak intensity. Repeating the test process for each emitter E(n) we obtain the reflected signals arrival times T1(n) and T2(n).

The time difference between these reflection signals T2(n)−T1(n) is determined by the time-shift determiner module 172 to create the reflection time difference TD(n)= T2(n)−T1(n). Repeating the process serially for multiple, preferably most or preferably all, of the emitter elements, lead to obtaining a reflection time difference set {TD(n)}.

After calibration mode procedure, the focusing mode is activated with the emitter array 112 driven with an calibrated focusing time-delay set {FPS(n)}={FT0(n)+CT(n)} to create an calibrated focusing focus peak.

In addition to phase corrections (i.e., time delays) for individual emitters En, also amplitude corrections are determined in embodiments. For example, for a given emitter test signal, the fractional intensity which is collected at the receiver peak (and optionally including the intensity of the nearest neighbors receivers also) for both the first boundary reflection and second boundary layer reflected echo signal is indicative of the remaining transmitted intensity that reaches the focus peak. Higher reflected fraction RI(n) means lower transmitted intensity fraction "TI(n)" contributing to the focus peak. Hence, in embodiments, the amplitude correction A(n) for each emitter En of the set {En} is a function of TI(n), e.g., proportional to 1/TI(n). For example, in embodiments, in order to obtain more uniform contribution to the focus peak from each emitter En, the intensity emitted from emitter En is set to be [1/TI(n)]*A0, where A0 is the intended average intensity of the transducer emitters array. In addition, to maximize the transmitted intensity, a step of frequency-test scan is performed prior to treatment application. Typical skull bone thickness ranges between 4 mm to 12 mm. Typical ultrasound treatment frequency ranges between 0.25 MHz to 2 MHz, which at average speed of sound in bone of 3000 m/s translates to a range of wavelength between 1.5 mm to 12 mm. Hence, ¼ wavelengths range in size between 0.375 mm to 3 mm. Due to the ¼ wavelength maximum transmission effect, for a given skull bone sample, for any given desired central frequency W0 for treatment (e.g., 1 MHz, with associated wavelength of 3 mm for bone speed of sound of 3000 m/s) there will be a particular optimal frequency W1 in the neighborhood of W0 for which the transmitted ultrasound total beam intensity across the skull bone layer is maximized. This can respectively be detected as a minimum in the reflected intensity.

Figure 39:
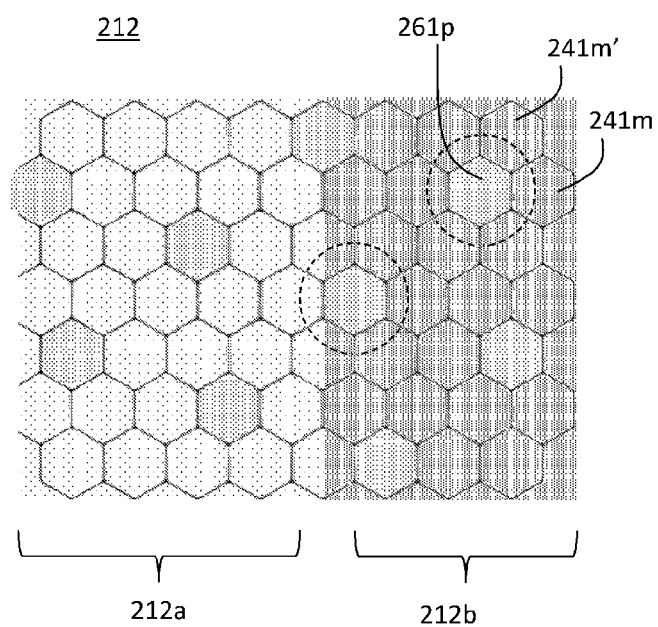
FIG. 39 illustrates a 2D array arrangement.

Since the intermediate skull layer (e.g., skull bone) thickness is non-uniform, it is possible and even likely that, the optimal frequency W1 of maximum transmitted intensity is different for different sub-regions of the surface area 155 under the full transducer area. Therefore, in embodiments, as illustrated in FIG. 39, the 2D surface area of the transducer emitter array 212 is subdivided into a set of two or more sub-sections {21 FIG. 22A, 2122B, etc . . . }.

The optimal frequency W1 is determined independently for each sub-section. Then, the treatment is delivered with each sub-section driven at its own local optimal frequency, in parallel or serially with other sub-sections of the transducer array.

Figure 40A:
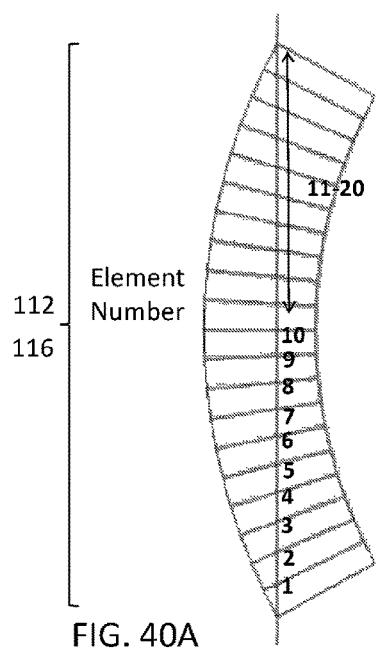
Figure 40B:
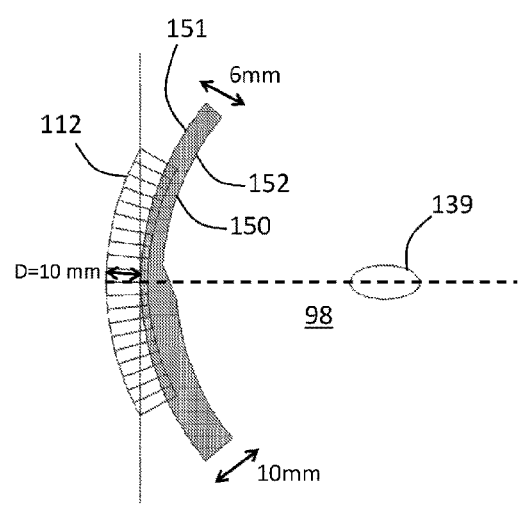

In all of the above examples, the key in the preparatory MEASURE process is to get separate measurements of individual emitters En (or small local group of emitters). In practice, the signals from sufficiently distant emitters do not mix or interfere at the small distance of the MEASURE reflection measurements. Therefore, in embodiments, the MEASURE process can be performed simultaneously on multiple emitters sub-set of the full array set {En} such that the distance between the array elements is larger than the distance between each array element and the intermediate skull layer 151. FIGS. 40-43 describe a computer simulation which illustrates the method and elements of the apparatus according to embodiments. While the simulation was conducted in 2D, its extension to 3D is straight forward to experts of the art. As illustrated in FIG. 40A, the emitters array 112 consists of 20 identical elements emitting ultrasound at frequency of 500 KHz. Each element width is 4 mm, the elements are ordered tightly along an arc of radius of curvature 80 mm. The array elements perform both as emitter and receiver sensors at the same location and thus it is representing also the receivers array 116. As illustrated in FIG. 40B, the intermediate curved layer 150, representing a skull bone element, is bounded by a front/outer boundary surface curve 151 in the shape of a smooth arc and back/inner boundary surface 152 in the shape of a curved step. Thereby, the intermediate payer 150 has asymmetric thickness going from 10 mm width on one side to 6 mm with on the other side. The speed of sound V1 in the uniform medium 98 outside of the intermediate skull layer 150 is chosen to be V1=1500 m/s. The speed of sound V2 in the inside of the intermediate skull layer 150 is chosen to be V2=4000 m/s. Hence a difference of 4 mm in passage length through the intermediate skull layer would cause a relative phase shift of 32 wavelength and result with destructive interference at the intended focus peak location instead of the intended constructive interference needed to create the peak as would be in uniform media 98. Because the curvature of the emitters array 112 and the intermediate skull layer outer surface 151 are not concentric, the distance between elements En of the array 112 and the intermediate skull layer surface 151 is not uniform, but it is roughly around 10 mm.

Figure 41:
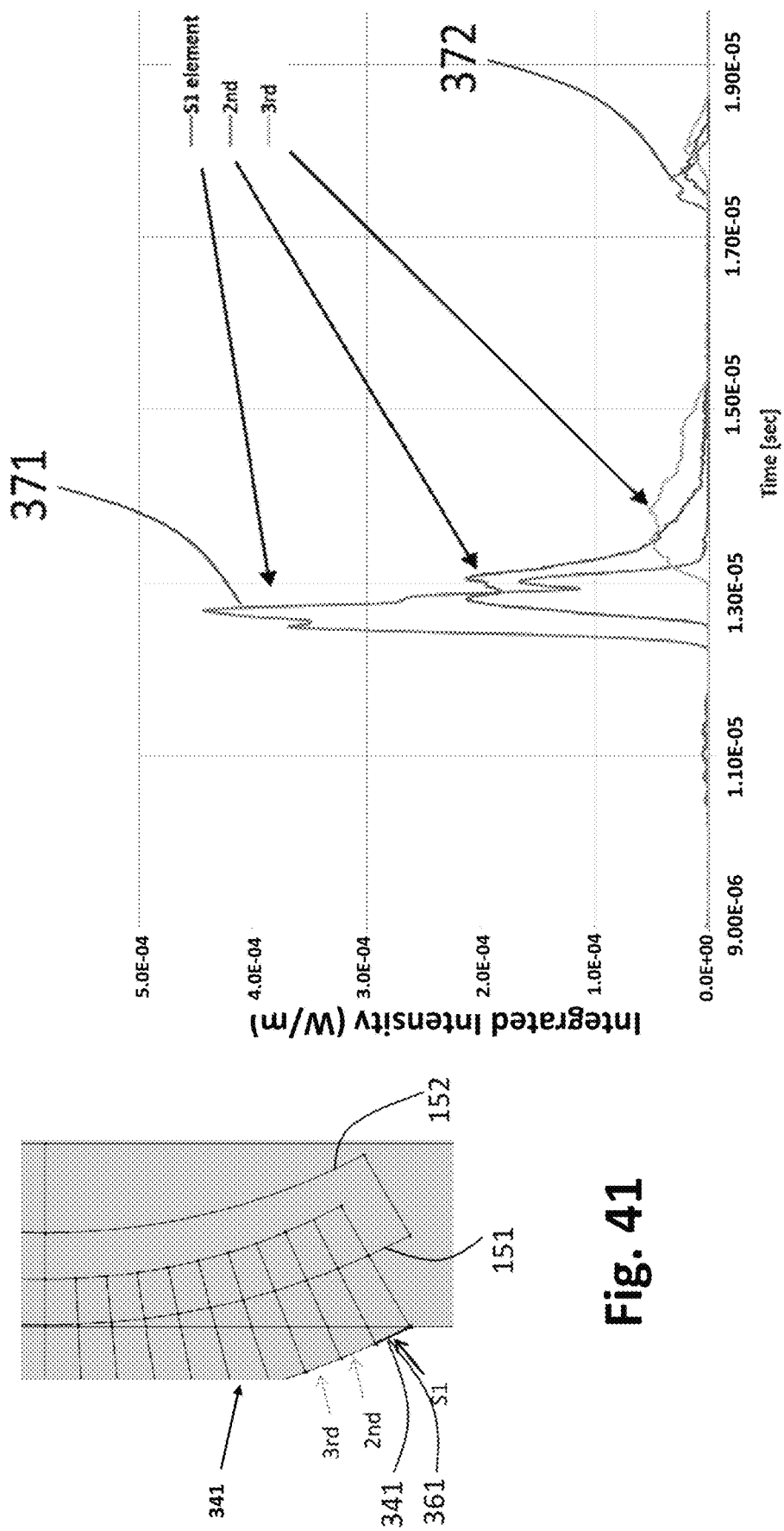

FIG. 41 illustrates the MEASURE step performed on one emitter element, labeled "s1". The signal is excited on S1 element, and measured on the same S1 element and two adjacent neighbors. The first peak at ~12 micro-sec corresponds to the front reflection 371 from the intermediate skull layer outer boundary surface. The second peak at ~17.5 micro-sec corresponds to the back layer reflection 272 from the inner boundary surface. We note that, as expected, there are received echo reflected signals on multiple neighboring receiver elements (such as the nearby ones labeled "2nd" and "3rd" on FIG. 41). Thus, the measurement is a signal-selection process, which in the this simulation is decided by the sensor on which the first reflected echo signal 171 was the strongest intensity. Then the measurement of the second echo reflected signal 172 was chosen to be measured on the same receiver sensor irrespective of its strength. For the emitter element S1 illustrated in FIG. 41, the reflected signals were also measured on the same element E1. This happens to be the case since the array 112 is positioned close to the layer surface 151 and also because the curvature of the array is very close to concentric with the curvature of the intermediate skull layer.

In embodiments, of the MEASURE procedure the array 112 is positioned close to the skull, hence close to the skull boundary surface 151. In embodiments, the curvature of the array is very close to concentric with the generic curvature of the human skull layer, typically between 26 Cm and 122 Cm radius of curvature. Yet, different areas of the skull have some difference in curvature, and also there is a range of curvature differences between human individuals. Therefore, in some preferred embodiments, instead of fixed array curvature, the array curvature used in a particular instance can be modifiable to better match to the area of the skull that is irradiated in practice. i.e., prior to the start of PROC-1 as discussed above, there is an initial "curvature adjustment" step.

The MEASURE procedure in the simulation consisted of serially performing the same MEASURE step on all the 20 emitters forming the emitters array 112 set {En}.

FIG. 42 illustrates the ANALYSIS procedure portion of PROC-1. The first column (#1) numbers the emitters {En} where "n" goes from 1 to 20. Column #2 indicates the emitter on which the first reflected signal from the intermediate skull layer outer (front) boundary surface 151 surface (which was emitted from that line "n"th emitter) was the largest intensity. Column #3 indicates the emitter on which the reflected signal from the intermediate skull layer inner (back) boundary surface 152 surface (which was emitted from that line "n"th emitter) was the largest intensity. Column #4 lists the Front-Reflection-Time set {TFRn} of measured time period which took the first reflected signal from the intermediate skull layer outer (front) boundary surface 151 surface counted from when it was emitted from that line "n"th emitter. Column #5 lists the Back-Reflection-Time set {TBRn} of measured time period which took the first reflected signal from the intermediate skull layer inner (back) boundary surface 152 surface counted from when it was emitted from that line "n"th emitter. Column #6 lists the resulting set {TD(n)} of time difference TD(n) between the two reflected times. This is the main component of the ANALYSIS procedure, from which all else it derived by various estimation approximations. Column #7 lists the resulting estimated layer passage time TD(n)/2 between the two reflected times. The next column lists the resulting calibration set {CT(n)} of correction factors CT(n) as function of TD(n)/2. The function used in the present simulation the estimation equation is $CT(n)=(V2/V1-1)*TD(n)/2$, which for the simulation case with V1=1500 and V2=4000 results in $CT(n)=1.66*TD(n)/2$.

FIGS. 223A, 223B, 223C illustrates the PROC-2 process simulation outcome of performing the calibrated focusing irradiation application procedure. Using the calibration set {CT(n)} from PROC-1, the system is activating the emitters array with the corrected set {FPS(n)} of input parameters phases.

FIG. 423A shows a train of several wave crests, a short time after being emitter from the emitters array {En} of 20 emitters and before arriving at the front boundary surface 151 of the intermediate skull layer 150. There is a visible time delay between the two sides of the array—one facing the narrow side of the intermediate skull layer 150 and the other side facing the wider side of the intermediate skull layer 150—creating creates a non-circular wave-front.

FIG. 423B shows a train of several wave crests, a short time after emerging off the back-boundary surface 152 of the intermediate skull layer 150. The wave-front is emerging with a well-coordinated circular wave-front between the two sides of the array—one facing the narrow side of the intermediate skull layer 150 and the other side facing the wider side of the intermediate skull layer 150, apart from a small and weak misalignment at the central area.

Finally, FIG. 423C shows the waves converging properly to a concentrated peak with the intended peak width 139 and at the intended peak location 131 within few millimeters deviation.

Importantly, we note that throughout the process (i.e., MEASURE, ANALYSIS, and irradiation), as demonstrated in the simulation, there was no need to recourse to a geometrical reconstruction of the macro shape of the intermediate skull layer 150. Instead, local measurements where directly translated to local time shifts and calibration factors.

In the above embodiments examples the PROC-1 MEASURE process and the PROC-2 irradiation process where both performed with the emitters array 112 at the same relative position with respect to the intermediate skull layer 150. But this is not necessarily the case.

FIG. 44 illustrates a flow chart of an embodiment of the method of invention.

Figure 44A:
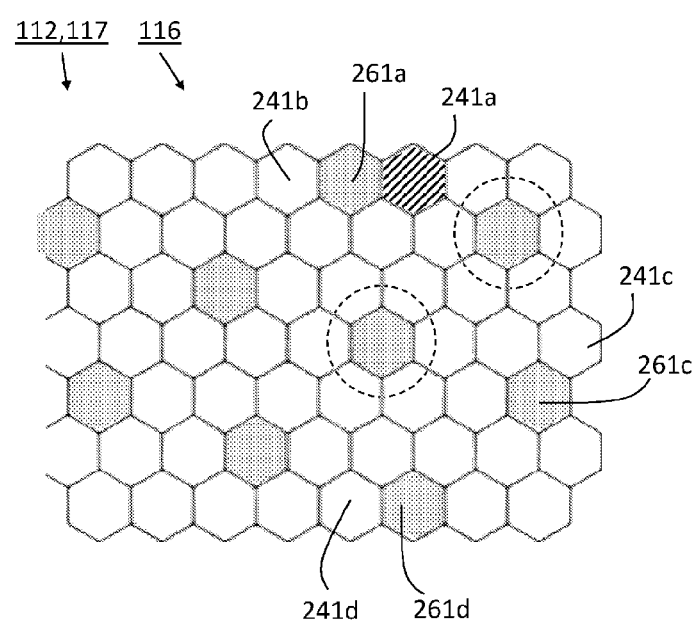
FIGS. 44A-44D illustrate embodiments of activation patterns of the calibration emitters array.
Figure 44B:
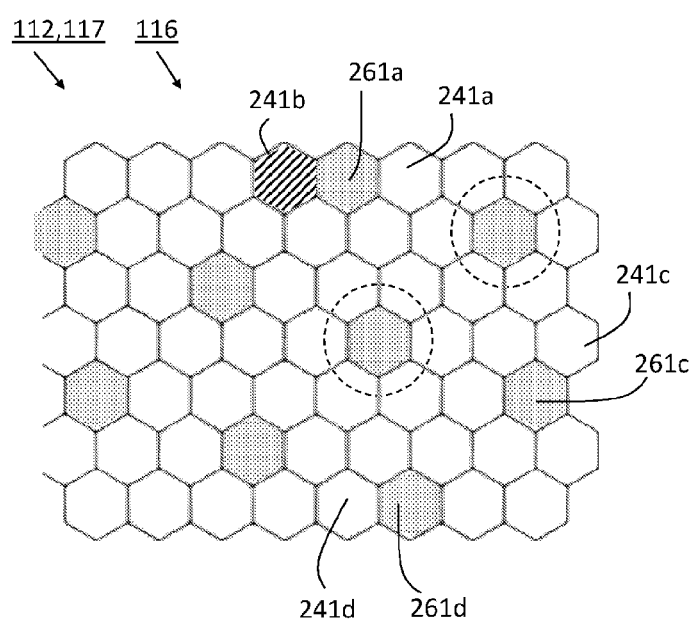
Figure 44C:
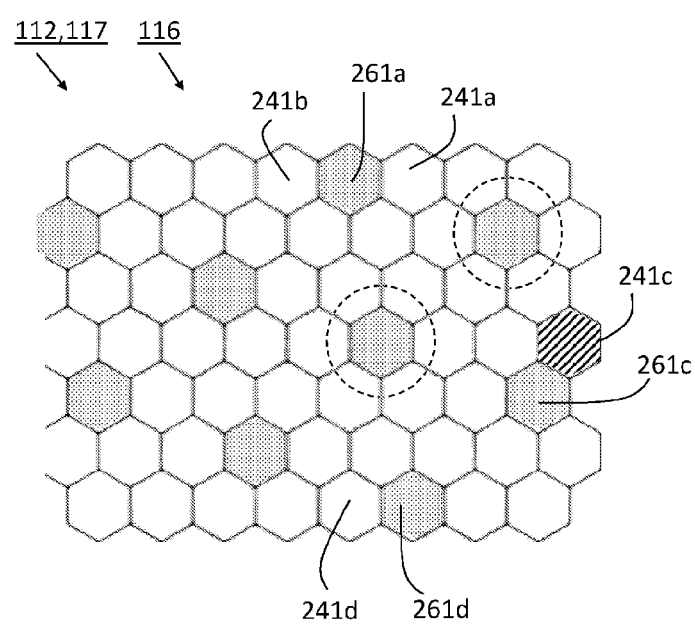
Figure 44D:
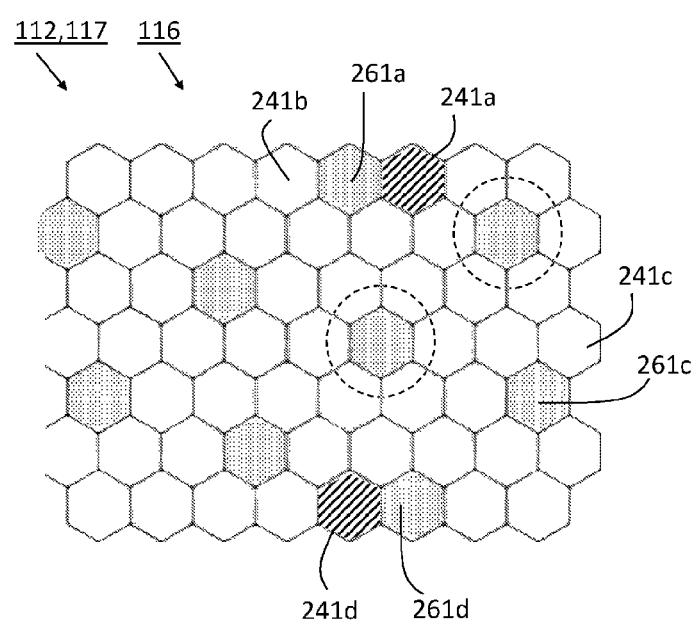
Figure 45C:
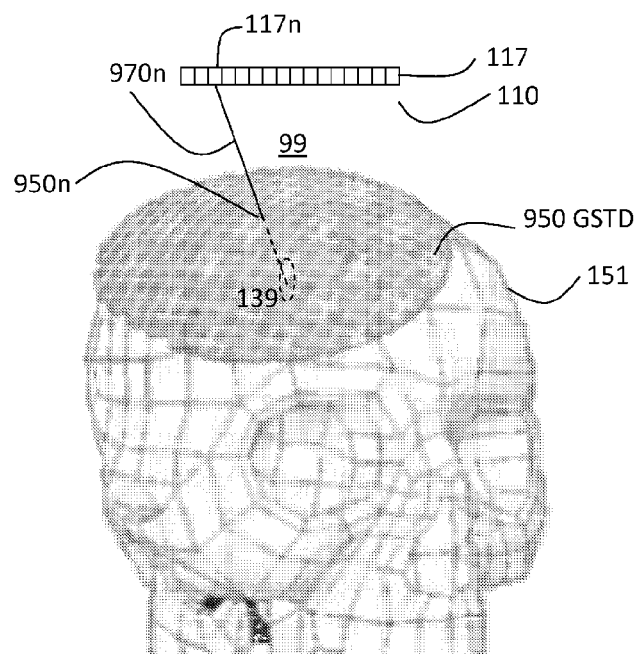

FIGS. 44A-44D illustrate embodiments of activation patterns of the calibration emitters array 112. Elements of the receivers array 116 are marked by dotted hexagons, and the remaining elements are emitters. In this embodiment, the same physical emitters serve for both the calibration emitters array 112 and the focusing emitters array 117. Activated emitter elements are marked by line-filled hexagon (as element 241a in FIG. 44A) and dormant emitters are marked by white filled hexagons. Thus, the activation state illustrated in FIG. 44A is one wherein only emitter element 241a is activated and all other emitters are dormant. FIG. 44B is one wherein only emitter element 241b is activated and all other emitters are dormant. FIG. 44C is one wherein only emitter element 241c is activated and all other emitters are dormant. FIG. 44D is one wherein both emitter elements 241a and 241d are activated and all other emitters are dormant. During the calibration measurement process, the system serially activates configurations of the calibration emitters. In order to prevent interference of test signals from different emitters, in some configurations only a single calibration emitter is activated while all other emitters are dormant. Yet, if emitters are sufficiently distant from one another that interference is minimal enough to not disturb the test signal proper detection then it may be possible in some embodiments to simultaneously activate more than one calibration emitter (e.g., as illustrated in FIG. 44D) during the calibration process.

The method and system of the present invention can be employed either
  (i) when the PROC-1 MEASURE process and the PROC-2 irradiation process are performed with the array 112 of ultrasound calibration-emitters {CE(m)}= {CE(1), CE(2) . . . CE(M)}, and an array 117 of ultrasound focus-emitters {FE(n)}={FE(1), FE(2) . . . FE(N)} are at the same relative position with respect to the intermediate skull layer 150; or
  (ii) when the PROC-1 MEASURE process and the PROC-2 irradiation process are performed with the array 112 of ultrasound calibration-emitters {CE(m)}= {CE(1), CE(2) . . . CE(M)}, and an array 117 of ultrasound focus-emitters {FE(n)}={FE(1), FE(2) . . . FE(N)} are at different relative positions with respect to the intermediate skull layer 150.

In the following discussion, we elaborate the case when the PROC-1 MEASURE process and the PROC-2 irradiation process are performed with the array 112 of ultrasound calibration-emitters {CE(m)}={CE(1), CE(2) . . . CE(M)}, and an array 117 of ultrasound focus-emitters {FE(n)}={FE(1), FE(2) . . . FE(N)} are at different relative positions with respect to the intermediate skull layer 150.

The key outcome, of this modified embodiment of the calibration ANALYSIS procedure, is the construction of a fictitious-skull geometry and associated phase shifts distribution. The PROC-2 irradiation focusing process is then performed as if the irradiated intermediate skull layer object is of the properties of the fictitious-skull rather than the real patient skull.

For removal of any doubt, the array 112, of the emitters used for calibration-emitters function, can be both geometrically and physically different from the array 117 of the emitters used for the focus-emitters function. From the calibration procedure outcome, it is the data of the fictitious-skull geometry and phase shifts which is the input in to the focusing procedure. Hence, the focusing array configuration can in principle be independent of the configuration of the calibration array used for producing the phase shifts input data.

For the sake of simplicity of the drawings and discussion, we shall make the presentation in terms of an engineering embodiment where there is one physical system of emitters that serves for both the calibration-emitters {CE(m)} and the focus-emitters {FE(n)}. This is in reality the simplest to construct from an engineering realization point of view. Yet, functionally we continue to designate the array as 112 when the emitters are used as calibration-emitters function, and designate the array as 117 when the emitters are used as focus-emitters function.

In order to distinguish this more particular embodiment of the PROC-1 MEASURE process, we shall refer to is as a MEASURE-Trace process. The PROC-1 MEASURE-Trace process implements serial activation of an array of ultrasound probes, each placed at an associated probing-location relative to the skull. The PROC-1 MEASURE-Trace process implements the serial activation of an array of ultrasound probes to trace, at discrete locations, the shape of the external skull and measure an effective local ultrasound time delay phase shift directly. An effective fictitious skull model shape and thickness model is produced as an outcome of the PROC-1 MEASURE-Trace process. Subsequently, for the PROC-2 irradiation focus process, the focus-emitters array 117, which can be placed at any geometrical position and orientation relative to the traced external skull geometry, is activated for focusing at any location within the skull, while computing the focusing phase shifts with respect to the effective fictitious skull model, taking the effective fictitious skull model external surface as coinciding with the human subject skull, using known in the art methods for focusing through a known layer geometry. An assumed speed of sound properties of the skull layer is also taken into consideration as is known in the art.

FIGS. 45A, 45B illustrate an embodiment where the PROC-1 MEASURE process and the PROC-2 irradiation process where performed with the emitters array 112 at the different relative position with respect to the intermediate skull layer 150. In particular, as illustrated in FIG. 45B, due to the location of the intended focus relative to the layer 150, it may be preferable to perform the PROC-2 irradiation process with the emitters array 112 relatively at bigger distance from the intermediate skull layer 150. Yet, as illustrated in FIG. 45A, there may be precision advantages to still perform the PROC-1 MEASURE process with the array 112 closer to the intermediate skull layer 150. The problem is that the path of emitted wave from a given emitter to the intended focus location 131 is not passing through the same intermediate skull layer section (e.g., skull bone section) in both cases. For example, as illustrated for the emitter E1, the path 370 in FIG. 45A from emitter E1 to the intended focus 131 is passing through a different location in the intermediate skull layer 150 from the path 970 in FIG. 45B from emitter E1 to the intended focus 131.

In embodiments, in order to enable preferred embodiment where the PROC-1 MEASURE process and the PROC-2 irradiation process where performed with the emitters array 112 at the different relative position with respect to the intermediate skull layer 150, we introduce in PROC-1 an optional supplemental ANALYSIS step—labeled VIRTUAL LAYER CONSTRUCTION—and introduce in PROC-2 a supplemental irradiation preparation optional step—labeled PATH ANALYSIS. The key additional step is the VIRTUAL LAYER CONSTRUCTION sub-process at the end of the ANALYSIS process.

The VIRTUAL LAYER CONSTRUCTION outcome is a geometrical construction which overlap a portion of the intermediate skull layer which is facing the emitters array 112 during the MEASURE process. The virtual layer construction comprises of at least two properties: (A) a geometrical surface shape $z=B1(x,y)$, and (B) an associated effective geometrical-surface-time-difference value function $GSTD(x,y,z)$ as a function of the measured echo time difference set $\{METD(j,k1,k2)\}$.

The time delays set $\{TD(n)\}$ is generated as a function of the geometrical-surface-time-difference value function $GSTD(x,y,z)$. In preferred embodiments, as illustrated in FIGS. 45B and 25C, the value of an element $TD(n)$ associated with a focus emitter $117n$ is primarily determined by the values of geometrical-surface-time-difference value function $GSTD(x,y,z)$ in proximity to the traversal area $TA(n)$ $950n$ location on the surface 950 $z=B1(x,y)$ traversed by the ray tracing $970n$ from the location of focus emitter $117n$ to the intended focused beam peak 139.

Generating a corrected focusing phase-shifts set $\{FPS(n)\}$ from the measured time delays set $\{TD(n)\}$ is following the same procedure as previously discussed.

In some embodiments the coordinate system $(x,y,z)$ axis are fixed relative to the geometry of the emitters array $\{CE(j)\}$. Thereby, positioning of the focusing emitters array $\{FE(n)\}$ can be determined by knowledge of the relative positioning of the focusing emitters array to the emitters array $\{CE(j)\}$.

In some embodiments the coordinate system $(x,y,z)$ axis are fixed relative to the geometry of the skull first boundary layer 151. Thereby, positioning of the focusing emitters array $\{FE(n)\}$ can be determined by knowledge of the relative positioning of the focusing emitters array to the skull first boundary layer 151.

In some embodiments, the value of $GSTD(x,y,z)$ is a function of the measured echo-difference set $\{METD(j,k1,k2)\}$ such that contributions from $METD(j,k1,k2)\}$ values are weighed higher where $CE(j)$ is a nearer calibration-emitter to the location to the geometrical point $(x,y,z)$.

In some embodiments, the value of $GSTD(x,y,z)$ is a function of the measured echo-difference set $\{METD(j,k1,k2)\}$ such that contributions from $METD(j,k1,k2)\}$ is weighed highest where $CE(j)$ is a nearest calibration-emitter to the location to the geometrical point $(x,y,z)$. For example, the value of $GSTD(x,y,z)$ is set equal to $METD(j,k1,k2)\}$ is weighed highest where $CE(j)$ is a nearest calibration-emitter to the location to the geometrical point $(x,y,z)$.

In some embodiments, the value of $GSTD(x,y,z)$ is a weighted sum of the elements of the measured echo-difference set $\{METD(j,k1,k2)\}$ such that contributions from $METD(j,k1,k2)\}$ is weighed highest where $CE(j)$ is a nearest calibration-emitter to the location to the geometrical point $(x,y,z)$. For example, the value of $GSTD(x,y,z)$ is set equal to the weighted average of two $METD(j,k1,k2)\}$associated with the two nearest calibration-emitters to the location to the geometrical point $(x,y,z)$, with the weight proportional to their distance from the geometrical point $(x,y,z)$.

For better outcome, it is advantageous if the geometrical-surface-time-difference value function $GSTD(x,y,z)$ geometry, specified by a shape function $z=B1(x,y)$, is an approximation of the outer boundary surface 151 of the skull. For example in some embodiments $z=B1(x,y))$ is a curved surface with a curvature of a typical human skull facing the location of the calibration emitters array.

In some embodiments, the geometrical shape function $z=B1(x,y)$ construction is derived from the set of parameters obtained in the invention SCAN process and ANALYSIS as deduced from the echoes reflection from the skull surface. For example, the timing of first echo from a calibration emitter $CE(j)$ serves to determine the geometrical distance of the outer skull surface from the geometrical location of the emitter $CE(j)$.

Generation of a measured time delays set $\{TD(n)\}$ as a function of the geometrical-surface-time-difference value function $GSTD(x,y,z)$ is performed by the following procedure: Since $\{TD(n)\}$ is associated with the focus-emitters array {FE(n)}, the pre-determined intended positioning of the focus-emitters array {FE(n)} with respect to the geometrical shape function z=B1(x,y) of the geometrical-surface-time-difference value function GSTD(x,y,z) needs to be assumed as given (even if the physical array of focusing emitters is not yet placed there).

As indicated in FIG. 45A, the MEASURE process ANALYSIS provides in formation only on a limited section of the intermediate skull layer (e.g., skull bone) and therefore only for sub-section 950, smaller than the full skull surface area, there is a constructed shape function z=B1(x, y).

The fictitious skull layer thickness at various locations, i.e., the local distance between Z1(x,y) surface and Z2(x,y) surface can be set in principle from the measured echo time difference S125 METD(j,k1,k2)=T2-T1, between detecting S123 at receiver CR(k1) and measure time T1 of first echo from the skull first boundary surface and detecting S124 at receiver CR(k2) and measure time T2 of second echo from the skull second boundary surface, of an unfocused ultrasound test signal that is emitted S122 from the calibration emitter CE(j).

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

The present invention has been described using detailed descriptions of embodiments thereof that are provided byway of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art.

What is claimed is:

1. A method for generating an ultrasound intensity-peak within a human subject brain around a target-peak-location, by delivering ultrasound through a skull of the human subject, the skull having an outer-facing surface, the method comprising:
   a. providing an array of ultrasound transducers (AUT);
   b. operating at least some transducers of the AUT to subject the skull to at least L ultrasound skull-probe (USP) events {USP-event$_i$, USP-event$_2$ ... USP-event$_L$} (L is a positive integer; L≥5) such that:
      (i) during each USP-event$_i$, a respective ultrasound test signal UTS$_i$ emitted by one or more transducer(s) of the AUT probes the skull to produce a maximum intensity at a different respective event-specific skull-surface location max_intensity_SOS_LOC (USP-event$_i$) that is on the outer-facing surface of the skull, said respective event-being specific for each USP-event$_i$;
      (ii) each USP-event$_i$ is defined by a different respective dominant emission-locale DEL(USP-event$_i$) such that during each USP-event$_i$ at least 50% of power of the respective ultrasound test signal UTS$_i$ received at the respective skull-surface location max_intensity_SOS_LOC (USP-event$_i$) on the skull is supplied by transmitter(s) of the AUT whose center(s) is(are) disposed within the dominant emission-locale DEL (USP-event$_i$), the dominant emission-locale DEL (USP-event$_i$) being spherical in shape with a radius of at most 0.5 cm;
      (iii) the dominant emission locales are distributed in space so that no two dominant emission locales [(DEL(USP-event$_j$), DEL(USP-event$_k$)](j≠k) (both j and k are positive integers equal to at most L) are displaced from each other to have a center-center distance of less than 2 cm;
   c. for each USP-event$_i$ having its respective ultrasound test signal UTS$_i$ and its respective dominant emission-locale DEL(USP-event$_i$), respectively receiving ultrasound reflected from the skull during the USP-event$_i$ into a respective one or more of the transducer(s) of the AUT;
   d. electronically processing output of the transducer(s) which receive the reflected ultrasound from each USP-event$_i$; and
   e. operating at least some transducers of the AUT in relative phases determined from results of the electronic processing of step (d) so as to generate the ultrasound intensity-peak within the human subject brain around the target-peak-location.

2. A method for generating an ultrasound intensity-peak within a human subject brain around a target-peak-location, by delivering ultrasound through a skull of the human subject, the skull having an outer-facing surface, the method comprising:
   a. providing an array of ultrasound transducers (AUT);
   b. operating at least some transducers of the AUT to subject the skull to at least L ultrasound skull-probe (USP) events {USP-event$_1$, USP-event$_2$ ... USP-event$_L$} (L is a positive integer; L≥5) such that:
      (i) during each USP-event$_i$, a respective ultrasound test signal UTS$_i$ emitted by one or more transducer(s) of the AUT probes the skull to produce a maximum intensity at a different respective event-specific skull-surface location max_intensity_SOS_LOC (USP-event$_i$) that is on the outer-facing surface of the skull, said respective event-specific skull-surface location max_intensity_SOS_LOC(USP-even) being specific for USP-event$_i$;
      (ii) each USP-event$_i$ is defined by a different respective dominant emission-locale DEL(USP-event$_i$) such that during each USP-event$_i$ at least 50% of power of the respective ultrasound test signal UTS$_i$ received at the respective skull-surface location max_intensity_SOS_LOC(USP-event$_i$) on the skull is supplied by transmitter(s) of the AUT whose center(s) is(are) disposed within the dominant emission-locale DEL (USP-event$_i$), the dominant emission-locale DEL (USP-event$_i$) being spherical in shape with a radius of at most 0.5 cm;
      (iii) the dominant emission locales are distributed in space so that no two dominant emission locales [(DEL(USP-event$_j$), DEL(USP-event$_k$)](j≠k) (both j and k are positive integers equal to at most L) are displaced from each other to have a center-center distance of less than 2 cm;
   c. for each USP-event$_i$ having its respective ultrasound test signal UTS$_i$ and its respective dominant emission-locale DEL(USP-event$_i$), measuring a respective echo time-difference ETD(USP-event$_i$) between:
      (i) a first measured time T$_1$(USP-event$_i$) at which the respective ultrasound test signal UTS$_i$ received into one of the transducers of the array;

(ii) a second measured time $T_2$(USP-event$_i$) at which the respective ultrasound test signal UTS$_i$ received into the same one or a different one of the transducers of the array; and d. operating at least some transducers of the AUT in focus-around-target-peak-location (FATPL) mode to simultaneously irradiate the skull, wherein step (d) is performed such that:

A. the at least some transducers deliver ultrasound at relative phases computed from the echo time-differences measured in step (c); and B. the delivering of ultrasound from the at least some transducers generates the ultrasound intensity-peak within the human subject brain around the target-peak-location-9%.

3. The method of claim 2 wherein the respective skull-surface locations max_intensity_SOS_LOC(USP-event$_i$) on the skull outer-facing surface form a location set SOS_LOC_SET {max_intensity_SOS_LOC((USP-event$_1$), max_intensity_SOS_LOC((USP-event$_2$) . . . max_intensity_SOS_LOC((USP-event$_L$)}, and wherein the skull-surface locations of the location set SOS_LOC_SET are distributed in space so that no two skull-surface locations (max_intensity_SOS_LOC(USP-event$_j$), max_intensity_SOS_LOC(USP-event$_j$)) on the skull outer-facing surface are displaced from each other by less than disp_numb cm, wherein disp_numb is a positive number whose value is at least 1.

4. The method of claim 2 wherein for each event USP-event$_i$ of the L events of {USP-event$_1$, USP-event$_2$ . . . USP-event$_L$}, a center of the respective dominant emission-locale DEL(USP-event$_i$) thereof is displaced from the skull by at most 2.5 cm.

5. The method of claim 2 wherein for each event USP-event$_i$ of the L events of {USP-event$_1$, USP-event$_2$ . . . USP-event$_L$}, a center of the respective dominant emission-locale DEL(USP-event$_i$) thereof is displaced from the skull by at most 2 cm or at most 1.5 cm.

6. The method of claim 2 wherein brain tissue of the subject is disposed within the skull of the subject, and wherein a nearest distance between (i) the target-peak-location in the brain tissue and (ii) the skull of the subject is at least 2 cm.

7. The method of claim 2, wherein each USP-event$_i$ is defined by a different respective dominant emission-locale DEL(USP-event$_i$) such that during each USP-event$_i$ the at least 50% of power of the respective ultrasound test signal UTS$_i$ received at the respective skull-surface location max_intensity_SOS_LOC (USP-event$_i$) on the skull is supplied by the transmitter(s) of the AUT (i) whose center(s) is(are) each disposed within a dominant emission-locale DEL (USP-event$_i$) that is spherical in shape with a radius of at most 0.5 cm; and (ii) which each have a width of at most ww cm, wherein 0≤ww≤1.

8. The method of claim 2 wherein for each event USP-event$_i$ of the L events of {USP-event$_1$, USP-event$_2$ . . . USP-event$_L$}, the respective one of more transducer(s) which:

(i) receive ultrasound reflect by the skull and (ii) whose output is electronically processed to determine the relative phase used to generate the ultrasound intensity peak, are each disposed in the respective dominant emission-locale DEL(USP-event$_i$) for the event USP-event$_i$.

9. The method of claim 2 wherein the dominant emission locales are distributed in space so that a center-center distance between a first DEL(USP-event$_j$) and a second DEL(USP-event$_k$) of the dominant emission locales (j≠k) is at least 5 cm.

10. The method of claim 2 wherein at least 30% of ultrasound power of the intensity peak are supplied by transducer(s) disposed with any of the dominant emission-locales {DEL(USP-event$_1$), DEL(USP-event$_2$) . . . DEL (USP-event$_L$)} defined by the at least L ultrasound skull-probe (USP) events {USP-event$_1$, USP-event$_2$ . . . USP-event$_L$}.

11. The method of claim 2 wherein at least 50% (or at least 75%) of ultrasound power of the intensity peak are supplied by transducer(s) disposed with any of the dominant emission-locales {DEL(USP-event$_1$), DEL(USP-event$_2$) . . . DEL(USP-event$_L$)} defined by the at least L ultrasound skull-probe (USP) events {USP-event$_1$, USP-event$_2$ . . . USP-event$_L$}.

12. The method of claim 2 wherein the ultrasound intensity-peak produced by operating the at least some transducers in the relative phases produces the intensity-peak so that a FWHM full width half maximum thereof in a widest dimension is at most 5 cm.

\* \* \* \* \*